United States Patent
Muthuppalniappan et al.

(10) Patent No.: US 7,951,814 B2
(45) Date of Patent: May 31, 2011

(54) QUINAZOLINEDIONE DERIVATIVES AS TRPA1 MODULATORS

(75) Inventors: Meyyappan Muthuppalniappan, Hyderabad (IN); Abraham Thomas, Navi Mumbai (IN); Sukeerthi Kumar, Navi Mumbai (IN); Sanjay Margal, Navi Mumbai (IN); Neelima Khairatkar-Joshi, Thane (IN); Indranil Mukhopadhyay, Navi Mumbai (IN); Srinivas Gullapalli, Navi Mumbai (IN)

(73) Assignee: Glenmark Pharmaceuticals, S.A., La Chaux-De-Fonds (CH)

( * ) Notice: Subject to any disclaimer, the term of this patent is extended or adjusted under 35 U.S.C. 154(b) by 0 days.

(21) Appl. No.: 12/485,600

(22) Filed: Jun. 16, 2009

(65) Prior Publication Data

US 2009/0325987 A1 Dec. 31, 2009

Related U.S. Application Data

(60) Provisional application No. 61/081,120, filed on Jul. 16, 2008, provisional application No. 61/092,592, filed on Aug. 28, 2008, provisional application No. 61/099,961, filed on Sep. 25, 2008, provisional application No. 61/119,446, filed on Dec. 3, 2008, provisional application No. 61/150,234, filed on Feb. 5, 2009.

(30) Foreign Application Priority Data

| Jun. 17, 2008 | (IN) | 1275/MUM/2008 |
| Aug. 5, 2008 | (IN) | 1666/MUM/2008 |
| Sep. 9, 2008 | (IN) | 1906/MUM/2008 |
| Nov. 5, 2008 | (IN) | 2358/MUM/2008 |
| Jan. 23, 2009 | (IN) | 156/MUM/2009 |

(51) Int. Cl.
*A61K 31/517* (2006.01)
(52) U.S. Cl. .................... 514/266.3; 544/285
(58) Field of Classification Search ............ 544/285
See application file for complete search history.

(56) References Cited

U.S. PATENT DOCUMENTS

2009/0176883 A1 * 7/2009 Perner et al. .......... 514/570

FOREIGN PATENT DOCUMENTS

| WO | WO 2004/055054 | 7/2004 |
| WO | WO 2005/089206 | 9/2005 |
| WO | WO-2007073505 A2 | 6/2007 |
| WO | WO 2008/094909 | 8/2008 |
| WO | WO 2009/002933 | 12/2008 |

OTHER PUBLICATIONS

MacPherson LJ et al, Nature, 2007, 445; 541-545.

* cited by examiner

*Primary Examiner* — James O Wilson
*Assistant Examiner* — Brian McDowell
(74) *Attorney, Agent, or Firm* — Blank Rome LLP

(57) ABSTRACT

The present invention provides Quinazolinedione derivatives as TRPA (Transient Receptor Potential subfamily A) modulators. In particular, compounds described herein are useful for treating or preventing diseases, conditions and/or disorders modulated by TRPA1 (Transient Receptor Potential subfamily A, member 1). Also provided herein are processes for preparing compounds described herein, intermediates used in their synthesis, pharmaceutical compositions thereof, and methods for treating or preventing diseases, conditions and/or disorders modulated by TRPA1.

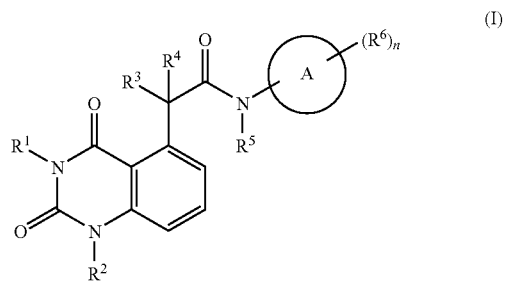

(I)

23 Claims, 3 Drawing Sheets

Effect of Compounds 10 & 37 in formalin (2.5%)
induced nocifensive pain model in SD rats Effect of Compound 10 on FCA induced mechanical
hyperalgesia in male SD rats

* $p < 0.05$,  $p < 0.01$, * $p < 0.001$ vs Vehicle by One-way ANOVA (Tukey's test)

QUINAZOLINEDIONE DERIVATIVES AS TRPA1 MODULATORS

RELATED APPLICATIONS

This application claims the benefit of Indian Patent Application Nos. 1275/MUM/2008 filed on Jun. 17, 2008; 1666/MUM/2008 filed on Aug. 5, 2008; 1906/MUM/2008 filed on Sep. 9, 2008; 2358/MUM/2008 filed on Nov. 5, 2008 and 156/MUM/2009 filed on Jan. 23, 2009 and U.S. Provisional Application No. 61/081,120 filed on Jul. 16, 2008; 61/092,592 filed on Aug. 28, 2008; 61/099,961 filed on Sep. 25, 2008; 61/119,446 filed on Dec. 3, 2008 and 61/150,234 filed on Feb. 5, 2009 all of which are hereby incorporated by reference.

TECHNICAL FIELD

The present patent application relates to quinazolinedione derivatives with Transient Receptor Potential Ankyrin1 (TRPA1) activity.

BACKGROUND

The Transient Receptor Potential (TRP) channels or receptors are pain receptors. They have been classified into seven subfamilies: TRPC (canonical), TRPV (vanilloid), TRPM (melastatin), TRPP (polycystin), TRPML (mucolipin), TRPA (ankyrin, ANKTM1) and TRPN (NOMPC) families. The TRPC family can be divided into 4 subfamilies (i) TRPC1 (ii) TRPC2 (iii) TRPC3, TRPC6, and TRPC7 and (iv) TRPC4 and TRPC5 based on sequence functional similarities. Currently the TRPV family has 6 members. TRPV5 and TRPV6 are more closely related to each other than to TRPV1, TRPV2, TRPV3, or TRPV4. TRPA1 is most closely related to TRPV3, and is more closely related to TRPV1 and TRPV2 than to TRPV5 and TRPV6. The TRPM family has 8 members. Constituents include the following: the founding member TRPM1 (melastatin or LTRPC1), TRPM3 (KIAA1616 or LTRPC3), TRPM7 (TRP-PLIK, ChaK(1), or LTRPC7), TRPM6 (ChaK2), TRPM2 (TRPC7 or LTRPC2), TRPM8 (TRP-p8 or CMR1), TRPM5 (MTR1 or LTRPC5), and TRPM4 (FLJ20041 or LTRPC4). The TRPML family consists of the mucolipins, which include TRPML1 (mucolipin 1), TRPML2 (mucolipin 2), and TRPML3 (mucolipin 3). The TRPP family consists of two groups of channels: those predicted to have six transmembrane domains and those that have eleven. TRPP2 (PKD2), TRPP3 (PKD2L1), and TRPP5 (PKD2L2) are all predicted to have six transmembrane domains. TRPP1 (PKD1, PC1), PKD-REJ and PKD-1L1 are all thought to have eleven transmembrane domains. The sole mammalian member of the TRPA family is ANKTM1.

It is believed TRPA1 is expressed in nociceptive neurons. Nociceptive neurons of the nervous system sense the peripheral damage and transmit pain signals. TRPA1 is membrane bound and most likely acts as a heterodimeric voltage gated channel. It is believed to have a particular secondary structure, its N-terminus is lined with a large number of ankyrin repeats which are believed to form a spring-like edifice. TRPA1 is activated by a variety of noxious stimuli, including cold temperatures (activated at 17° C.), pungent natural compounds (e.g., mustard, cinnamon and garlic), and environmental irritants (MacPherson L J et al, *Nature*, (2007), 445, 541-545). Noxious compounds activate TRPA1 ion channels through covalent modification of cysteines to form covalently linked adducts. A variety of endogenous molecules produced during tissue inflammation/injury have been identified as pathological activators of TRPA1 receptor. These include hydrogen peroxide which is produced due to oxidative stress generated during inflammation, alkenyl aldehyde 4-HNE—an intracellular lipid peroxidation product and cyclopentenone prostaglandin 15dPGJ2 which is produced from PGD2 during inflammation/allergic response. TRPA1 is also activated in receptor dependant fashion by Bradykinin (BK) which is released during tissue injury at peripheral terminals.

The difference between TRPA1 and other TRP receptors is that TRPA1 ligand binding persists for hours due to which the physiological response (e.g., pain) is greatly prolonged. Hence to dissociate the electrophile, an effective antagonist is required.

WO 2009/002933, WO 2008/0949099, WO 2007/073505, WO 2004/055054, and WO 2005/089206 describe the TRP channels as the targets for the treatment of pain and related conditions.

In efforts to discover better analgesics for the treatment of both acute and chronic pain and to develop treatments for various neuropathic and nociceptive pain states, there exists a need for a more effective and safe therapeutic treatment of diseases, conditions and/or disorders modulated by TRPA1.

SUMMARY

The present invention relates to compounds of the formula (I):

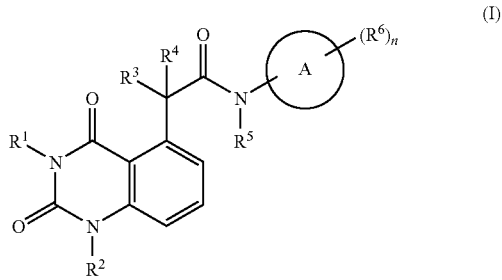

or esters thereof, tautomers thereof, stereoisomers thereof, and pharmaceutically acceptable salts thereof, wherein, ring A is aryl, heteroaryl, heterocyclyl or cycloalkyl;

at each occurrence $R^1$ and $R^2$ is independently selected from hydrogen, hydroxyl, substituted or unsubstituted alkyl, substituted or unsubstituted alkenyl, substituted or unsubstituted alkynyl, substituted or unsubstituted cycloalkyl, substituted or unsubstituted cycloalkylalkyl, $(CR^xR^y)_nOR^x$, $COR^x$, $COOR^x$, $CONR^xR^y$, $SO_2NR^xR^y$, $NR^xR^y$, $NR^x(CR^xR^y)_nOR^x$, $NR^x(CR^xR^y)_nCN(CH_2)_nNR^xR^y$, $(CH_2)_nCHR^xR^y$, $(CR^xR^y)NR^xR^y$, $NR^x(CR^xR^y)_nCONR^xR^y$, $(CH_2)_nNHCOR^x$ and $(CH_2)_nNH(CH_2)_nSO_2R^x$, and $(CH_2)_nNHSO_2R^x$;

each occurrence of $R^x$ and $R^y$ is independently selected from hydrogen, hydroxyl, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, or when directly attached to a common atom, $R^x$ and $R^y$ together with the atom to which they are attached may form an optionally substituted 3 to 7 membered saturated, unsaturated or partially saturated cyclic ring, which may optionally include at least two heteroatoms selected from O, $NR^a$ or S;

each occurrence of $R^a$ is independently hydrogen or substituted or unsubstituted alkyl;

$R^3$ and $R^4$ are independently selected from hydrogen, hydroxyl, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, or $R^3$ and $R^4$ may be joined together to form an optionally substituted 3 to 7 membered saturated or unsaturated cyclic ring, which may optionally include at least one heteroatom or group selected from O, $NR^a$, S, C(O) and $S(O)C_{0-2}$; and $R^5$ is selected from hydrogen, hydroxyl, substituted or unsubstituted alkyl, substituted or unsubstituted alkenyl, substituted or unsubstituted alkynyl, $(CR^xR^y)_nOR^x$, $COR^x$, $COOR^x$, $CONR^xR^y$, $S(O)_{0-2}NR^xR^y$, $NR^xR^y$, $NR^x(CR^xR^y)_nOR^x$, $NR^x(CR^xR^y)_nCN$ $(CH_2)_nNR^xR^y$, $(CH_2)_nCHR^xR^y$, $(CR^xR^y)NR^xR^y$, $NR^x(CR^xR^y)_nCONR^xR^y$, $(CH_2)_nNHCOR^x$ and $(CH_2)_nNH(CH_2)_nSO_2R^x$, and $(CH_2)_nNHSO_2R^x$;

each occurrence of $R^6$ is independently selected from hydrogen, cyano, nitro, —$NR^xR^y$, halogen, hydroxyl, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, haloalkyl, haloalkoxy, cycloalkylalkoxy, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, $C(O)OR^x$, $OR^x$, $C(O)NR^xR^y$, $C(O)R^x$, and $SO_2NR^xR^y$;

each occurrence of 'n' is selected from 0 to 5.

The compounds of formula (I) may involve one or more embodiments. It is to be understood that the embodiments below are illustrative of the present invention and are not intended to limit the claims to the specific embodiments exemplified.

According to one embodiment, specifically provided are compounds of the formula (Ia)

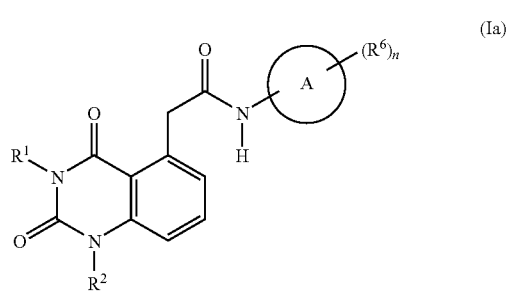

(Ia)

or esters thereof, tautomers thereof stereoisomers thereof, and pharmaceutically acceptable salts thereof,
wherein,
$R^1$ and $R^2$ are as defined above;
ring A is selected from phenyl, pyridinyl, pyrazolyl, thiazolyl and thiadiazolyl;
each occurrence of $R^6$ is independently hydrogen, cyano, nitro, $NR^xR^y$, halogen, hydroxyl, haloalkyl, haloalkoxy, cycloalkylalkoxy, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, $R^x$ and $R^y$ are independently selected from hydrogen, hydroxyl, halogen, substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, and substituted or unsubstituted heteroarylalkyl;

each occurrence of 'n' is independently selected from 0 to 5.

According to one embodiment, specifically provided are compounds of the formula (Ia) in which ring A is phenyl.

According to one embodiment, specifically provided are compounds of the formula (Ia) in which ring A is pyridine.

According to one embodiment, specifically provided are compounds of the formula (Ia) in which ring A is pyrazole.

According to one embodiment, specifically provided are compounds of the formula (Ia) in which ring A is thiazole.

According to one embodiment, specifically provided are compounds of the formula (Ia) in which ring A is thiadiazole.

According to one embodiment, specifically provided are compounds of the formula (Ia) in which $R^1$ and $R^2$ are independently hydrogen or, substituted or unsubstituted alkyl, preferably methyl.

According to one embodiment, specifically provided are compounds of the formula (Ia) in which $R^6$ is substituted or unsubstituted phenyl, wherein one or more substituents on the phenyl (substituent may be at any carbon) may be the same or different and are independently selected from halogens (e.g., fluorine, chlorine, bromine or iodine) or haloalkyl (e.g., trifluoromethyl).

According to one embodiment, specifically provided are compounds of the formula (Ia) in which $R^6$ is substituted or unsubstituted phenoxy, wherein the substituent on the phenoxy is alkyl, preferably methyl.

According to one embodiment, specifically provided are compounds of the formula (Ib)

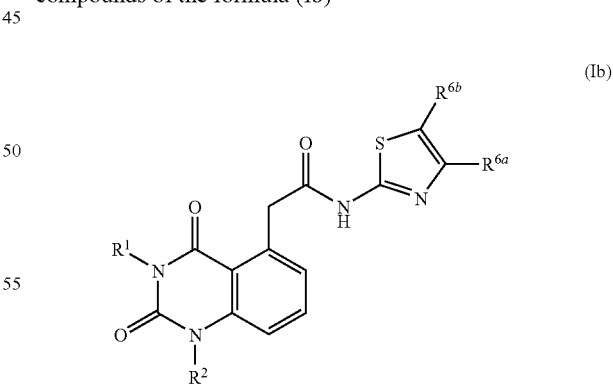

(Ib)

or esters thereof, tautomers thereof, stereoisomers thereof, and pharmaceutically acceptable salts thereof,
wherein,
$R^1$ and $R^2$ are as defined above;
$R^{6a}$ and $R^{6b}$ are independently selected from hydrogen, cyano, nitro, $NR^xR^y$, halogen, hydroxyl, haloalkyl, haloalkoxy, cycloalkylalkoxy, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, C(O)OR$^x$, OR$^x$, C(O)NR$^x$R$^y$, C(O)R$^x$, SO$_2$R$^x$, and SO$_2$—NR$^x$R$^y$, or R$^{6a}$ and R$^{6b}$ together with the carbon to which they are attached may form an optionally substituted 4 to 14 membered saturated, unsaturated or partially saturated ring system, which may optionally include one or more heteroatoms selected from O, N or S;

R$^x$ and R$^y$ are as defined above (e.g., as in Formula Ia).

According to one embodiment, specifically provided are compounds of the formula (Ib) in which R$^1$ and R$^2$ are independently hydrogen or substituted or unsubstituted alkyl, preferably methyl, ethyl or propyl.

According to one embodiment, specifically provided are compounds of the formula (Ib) in which R$^1$ is substituted or unsubstituted cycloalkylalkyl, preferably cyclopropylmethyl, and R$^2$ is alkyl, preferably methyl.

According to one embodiment, specifically provided are compounds of the formula (Ib) in which R$^1$ is COOR$^x$, wherein R$^x$ is alkyl, preferably ethyl, and R$^2$ is hydrogen.

According to one embodiment, specifically provided are compounds of the formula (Ib) in which R$^{6a}$ is substituted or unsubstituted phenyl, wherein one or more substituents on the phenyl (the substituent may be at any carbon) may be the same or different and are independently selected from halogen (e.g., fluorine, chlorine, bromine or iodine), alkyl (e.g., methyl, ethyl, isopropyl, iso-butyl, tert.-butyl), cycloalkyl (e.g.; cyclohexyl), haloalkyl (e.g. difluoromethyl, trifluoromethyl, dichloromethyl, trichloromethyl), alkoxy (e.g. methoxy, ethoxy), haloalkoxy (e.g., difluoromethoxy, trifluoromethoxy, trifluoroethoxy) or cycloalkylalkoxy (e.g., cyclopropylmethoxy); and R$^{6b}$ is hydrogen.

According to one embodiment, specifically provided are compounds of the formula (Ib) in which R$^{6a}$ is substituted or unsubstituted phenyl, wherein one or more substituents on the phenyl (the substituent may be at any carbon) are independently selected from halogens (e.g., fluorine, chlorine, bromine or iodine); and R$^{6b}$ is alkyl (e.g., methyl).

According to one embodiment, specifically provided are compounds of the formula (Ib) in which R$^{6a}$ is substituted or unsubstituted cycloalkyl (e.g., cyclohexyl); and R$^{6b}$ is hydrogen.

According to one embodiment, specifically provided are compounds or the formula (Ib) in which R$^{6a}$ is substituted or unsubstituted indolyl, wherein the substituent on the substituted indolyl is alkyl (e.g., methyl); and R$^{6b}$ is hydrogen.

According to one embodiment, specifically provided are compounds of the formula (Ib) in which R$^{6a}$ and R$^{6b}$ together with the carbon to which they are attached form a substituted or unsubstituted phenyl or dihydronaphthyl, wherein the substituent on the phenyl or dihydronaphthyl is selected from one or more halogen (e.g., F or Cl) or alkyl (e.g., methyl).

Below are representative compounds, which are illustrative in nature only and are not intended to limit to the scope of the invention.

N1-[4-(4-Bromophenyl)phenyl]-2-(1,3-dimethyl-2,4-dioxo-1,2,3,4-tetrahydro-5-quinazolinyl)acetamide, N1-[4-(4-Bromophenyl)phenyl]-2-(1,3-dimethyl-2,4-dioxo-1,2,3,4-tetrahydro-5-quinazolinyl)acetamide, N1-[4-(4-Methylphenoxy)phenyl]-2-(1,3-dimethyl-2,4-dioxo-1,2,3,4-tetrahydro-5-quinazolinyl)acetamide, N1-[6-(4-Chlorophenyl)-2-pyridyl]-2-(1,3-dimethyl-2,4-dioxo-1,2,3,4-tetrahydro-5-quinazolinyl)acetamide, N1-[5-(4-Chlorophenyl)-2-pyridyl]-2-(1,3-dimethyl-2,4-dioxo-1,2,3,4-tetrahydro-5-quinazolinyl)acetamide, N1-[6-(4-Trifluoromethylphenyl)-2-pyridyl]-2-(1,3-dimethyl-2,4-dioxo-1,2,3,4-tetrahydro-5-quinazolinyl)acetamide, N1-[4-(4-Cyclohexyl)-1,3-thiazol-2yl]-2-(1,3-dimethyl-2,4-dioxo-1,2,3,4-tetrahydro-5-quinazolinyl)acetamide, N1-[4-Phenyl-1,3-thiazol-2-yl]-2-(1,3-dimethyl-2,4-dioxo-1,2,3,4-tetrahydro-5-quinazolinyl)acetamide, N1-[4-(4-Fluorophenyl)-1,3-thiazol-2yl]-2-(1,3-dimethyl-2,4-dioxo-1,2,3,4-tetrahydro-5-quinazolinyl)acetamide, N1-[4-(4-Chlorophenyl-1,3-thiazol-2yl]-2-(1,3-dimethyl-2,4-dioxo-1,2,3,4-tetrahydro-5-quinazolinyl)acetamide, N1-[4-(3-Chlorophenyl)-1,3-thiazol-2yl]-2-(1,3-dimethyl-2,4-dioxo-1,2,3,4-tetrahydro-5-quinazolinyl)acetamide, N1-[4-(4-Bromophenyl-1,3-thiazol-2yl]-2-(1,3-dimethyl-2,4-dioxo-1,2,3,4-tetrahydro-5-quinazolinyl)acetamide, N1-[4-(4-Iodophenyl)-1,3-thiazol-2yl]-2-(1,3-dimethyl-2,4-dioxo-1,2,3,4-tetrahydro-5-quinazolinyl)acetamide, N1-[4-(4-Trifuromethylphenyl)-1,3-thiazol-2yl]-2-(1,3-dimethyl-2,4-dioxo-1,2,3,4-tetrahydro-5-quinazolinyl)acetamide, N1-[4-(3-Trifluoromethylphenyl)-1,3-thiazol-2yl]-2-(1,3-dimethyl-2,4-dioxo-1,2,3,4-tetrahydro-5-quinazolinyl)acetamide, N1-[4-(3-Trifluoromethoxyphenyl)-1,3-thiazol-2-yl]-2-(1,3-dimethyl-2,4-dioxo-1,2,3,4-tetrahydro-5-quinazolinyl)acetamide, N1-[4-(4-Methoxyphenyl)-1,3-thiazol-2-yl]-2-(1,3-dimethyl-2,4-dioxo-1,2,3,4-tetrahydro-5-quinazolinyl)acetamide, N1-[4-(4-Cyclohexylphenyl)-1,3-thiazol-2-yl]-2-(1,3-dimethyl-2,4-dioxo-1,2,3,4-tetrahydro-5-quinazolinyl)acetamide, N1-[4-(4-(3-Methylbutoxy)phenyl)-1,3-thiazol-2-yl]-2-(1,3-dimethyl-2,4-dioxo-1,2,3,4-tetrahydro-5-quinazolinyl)acetamide, N1-[4-(4-tert-Butylphenyl)-1,3-thiazol-2-yl]-2-(1,3-dimethyl-2,4-dioxo-1,2,3,4-tetrahydro-5-quinazolinyl)acetamide, N1-[4-(2-Isobutylphenyl)-1,3-thiazol-2-yl]-2-(1,3-dimethyl-2,4-dioxo-1,2,3,4-tetrahydro-5-quinazolinyl)acetamide, N1-[4-(4-Isopropylphenyl)-1,3-thiazol-2-yl]-2-(1,3-dimethyl-2,4-dioxo-1,2,3,4-tetrahydro-5-quinazolinyl)acetamide, N1-[4-(2-Ethylphenyl)-1,3-thiazol-2-yl]-2-(1,3-dimethyl-2,4-dioxo-1,2,3,4-tetrahydro-5-quinazolinyl)acetamide, N1-[4-(4-Methylphenyl)-1,3-thiazol-2-yl]-2-(1,3-dimethyl-2,4-dioxo-1,2,3,4-tetrahydro-5-quinazolinyl)acetamide, N1-[4-(4-Chlorophenyl)-1,3-thiazol-2-yl]-2-(1,3-diethyl-2,4-dioxo-1,2,3,4-tetrahydro-5-quinazolinyl)acetamide, N1-[4-(3-Trifluoromethylphenyl)-1,3-thiazol-2-yl]-2-(1,3-dipropyl-2,4-dioxo-1,2,3,4-tetrahydro-5-quinazolinyl)acetamide, N1-[4-(4-tert-Butylphenyl)-1,3-thiazol-2-yl]-2-(1-methyl-3-cyclopropylmethyl-2,4-dioxo-1,2,3,4-tetrahydro-5-quinazolinyl)acetamide, Ethyl-5-[2-(4-Chlorophenyl)-1,3-thiazol-5-ylcarboxymethyl]-2,4-dioxo-1,2,3,4-tetrahydro-3-quinazolinecarboxylate, N1-[4-(4-Chlorophenyl)-1,3-thiazol-2-yl]-2-(2,4-dioxo-1,2,3,4-tetrahydro-5-quinazolinyl)acetamide, N1-[4-(4-Chlorophenyl)-5-methyl-1,3-thiazolyl]-2-(1,3-dimethyl-2,4-dioxo-1,2,3,4-tetrahydro-5-quinazolinyl)acetamide, N1-[4-(2,4-Difluorophenyl)-1,3-thiazol-2-yl]-2-(1,3-dimethyl-2,4-dioxo-1,2,3,4-tetrahydro-5-quinazolinyl)acetamide, N1-[4-(3,4-Difluorophenyl)-1,3-thiazol-2-yl]-2-(1,3-dimethyl-2,4-dioxo-1,2,3,4-tetrahydro-5-quinazolinyl)acetamide, N1-[4-(2,6-Difluorophenyl)-1,3-thiazol-2-yl]-2-(1,3-dimethyl-2,4-dioxo-1,2,3,4-tetrahydro-5-quinazolinyl)acetamide, N1-[4-(3,5-Difluorophenyl)-1,3-thiazol-2-yl]-2-(1,3-dimethyl-2,4-dioxo-1,2,3,4-tetrahydro-5-quinazolinyl)acetamide, N1-[4-(2,3-Difluorophenyl)-1,3-thiazol-2-yl]-2-(1,3-dimethyl-2,4-dioxo-1,2,3,4-tetrahydro-5-quinazolinyl)acetamide, N1-[4-(2-Fluoro-4-trifluoromethylphenyl)-1,3-thiazol-2-yl]-2-(1,3-dimethyl-2,4-dioxo-1,2,3,4-tetrahydro-5-quinazolinyl)acetamide, N1-[4-(3-Fluoro-4-trifluoromethylphenyl)-1,3-thiazol-2-yl]-2-(1,3-dimethyl-2,4-dioxo-1,2,3,4-tetrahydro-5-quinazolinyl)acetamide, N1-[4-(4-Fluoro-3-trifluoromethylphenyl)-1,3-thiazol-2-yl]-2-(1,3-dimethyl-2,4-dioxo-1,2,3,4-tetrahydro-5-quinazolinyl)acetamide, N1-[4-(4-Fluoro-2-trifluoromethylphenyl)-1,3-thiazol-2-yl]-2-(1,3-dimethyl-2,4-dioxo-1,2,3,4-tetrahydro-5-quinazolinyl)acetamide, N1-[4-(2-Fluoro-5-trifluoromethylphenyl)-1,3-thiazol-2-yl]-2-(1,3-dimethyl-2,4-dioxo-1,2,3,4-tetrahydro-5-quinazolinyl)acetamide, N1-[4-(3-Fluoro-4-trifluoromethoxyphenyl)-1,3-thiazol-2-yl]-2-(1,3-dimethyl-2,4-dioxo-1,2,3,4-tetrahydro-5-quinazolinyl)propanamide, N1-[4-(4-Fluoro-3-trifluoromethoxyphenyl)-1,3-thiazol-2-yl]-2-(1,3-dimethyl-2,4-dioxo-1,2,3,4-tetrahydro-5-quinazolinyl)propanamide, N1-[4-(3-Fluoro-4-methoxyphenyl)-1,3-thiazol-2-yl]-2-(1,3-dimethyl-2,4-dioxo-1,2,3,4-tetrahydro-5-quinazolinyl)propanamide, N1-[4-(4-Difluoromethoxyl-3-fluorophenyl)-1,3-thiazol-2-yl]-2-(1,3-dimethyl-2,4-dioxo-1,2,3,4-tetrahydro-5-quinazolinyl)acetamide, N1-[4-(2,4-Dichlorophenyl)-1,3-thiazol-2yl]-2-(1,3-dimethyl-2,4-dioxo-1,2,3,4-tetrahydro-5-quinazolinyl)acetamide, N1-[4-(2,5-Dichlorophenyl)-1,3-thiazol-2-yl]-2-(1,3-dimethyl-2,4-dioxo-1,2,3,4-tetrahydro-5-quinazolinyl)acetamide, N1-[4-(3,4-Dichlorophenyl)-1,3-thiazol-2yl]-2-(1,3-dimethyl-2,4-dioxo-1,2,3,4-tetrahydro-5-quinazolinyl)acetamide, N1-[4-(3,5-Dichlorophenyl)-1,3-thiazol-2-yl]-2-(1,3-dimethyl-2,4-dioxo-1,2,3,4-tetrahydro-5-quinazolinyl)acetamide, N1-[4-(3-Chloro-4-fluorophenyl)-1,3-thiazol-2-yl]-2-(1,3-dimethyl-2,4-dioxo-1,2,3,4-tetrahydro-5-quinazolinyl)acetamide, N1-[4-(3-Chloro-2-fluorophenyl)-1,3-thiazol-2-yl]-2-(1,3-dimethyl-2,4-dioxo-1,2,3,4-tetrahydro-5-quinazolinyl)acetamide, N1-[4-(4-Chloro-2-fluorophenyl)-1,3-thiazol-2-yl]-2-(1,3-dimethyl-2,4-dioxo-1,2,3,4-tetrahydro-5-quinazolinyl)acetamide, N1-[4-(5-Chloro-2-fluorophenyl)-1,3-thiazol-2-yl]-2-(1,3-dimethyl-2,4-dioxo-1,2,3,4-tetrahydro-5-quinazolinyl)acetamide, N1-[4-(2-Chloro-6-fluorophenyl)-1,3-thiazol-2-yl]-2-(1,3-dimethyl-2,4-dioxo-1,2,3,4-tetrahydro-5-quinazolinyl)acetamide, N1-[4-(2-Chloro-4-fluorophenyl)-1,3-thiazol-2-yl]-2-(1,3-dimethyl-2,4-dioxo-1,2,3,4-tetrahydro-5-quinazolinyl)propanamide, N1-[4-(4-Chloro-3-trifluoromethylphenyl)-1,3-thiazol-2-yl]-2-(1,3-dimethyl-2,4-dioxo-1,2,3,4-tetrahydro-5-quinazolinyl)acetamide, N1-[4-(2-Chloro-5-trifuoromethylphenyl)-1,3-thiazol-2-yl]-2-(1,3-dimethyl-2,4-dioxo-1,2,3,4-tetrahydro-5-quinazolinyl)propanamide, N1-{4-[3-Chloro-4-(difluromethoxy)phenyl]-1,3-thiazol-2-yl}-2-(1,3-dimethyl-2,4-dioxo-1,2,3,4-tetrahydro-5-quinazolinyl)acetamide, N1-[4-(4-Chloro-3-methylphenyl)-1,3-thiazol-2yl]-2-(1,3-dimethyl-2,4-dioxo-1,2,3,4-tetrahydro-5-quinazolinyl)acetamide, N1-{4-[3-Fluoro-4-(2,2,2-trifluoroethoxy)phenyl]-1,3-thiazol-2yl}-2-(1,3-dimethyl-2,4-dioxo-1,2,3,4-tetrahydro-5-quinazolinyl)acetamide, N1-[4-(4-Cyclopropylmethoxy-3-fluorophenyl)-1,3-thiazol-2yl]-2-(1,3-dimethyl-2,4-dioxo-1,2,3,4-tetrahydro-5-quinazolinyl)acetamide, N1-[4-(3-Fluoro-4-trifluoromethylphenyl)-1,3-thiazol-2-yl]-2-(1-methyl-3-cyclopropylmethyl-2,4-dioxo-1,2,3,4-tetrahydro-5-quinazolinyl)acetamide, N1-[4-(4-(2,3,6-Trifluorophenyl)-1,3-thiazol-2-yl]-2-(1,3-dimethyl-2,4-dioxo-1,2,3,4-tetrahydro-5-quinazolinyl)acetamide, N1-[4-(2,4-Dichloro-5-fluorophenyl)-1,3-thiazol-2-yl]-2-(1,3-dimethyl-2,4-dioxo-1,2,3,4-tetrahydro-5-quinazolinyl)acetamide, N1-[4-(2,6-Dichloro-3-fluorophenyl)-1,3-thiazol-2-yl]-2-(1,3-dimethyl-2,4-dioxo-1,2,3,4-tetrahydro-5-quinazolinyl)acetamide, N1-[4-(2,3-Difluoro-4-trifluormethylphenyl)-1,3-thiazol-2-yl]-2-(1,3-dimethyl-2,4-dioxo-1,2,3,4-tetrahydro-5-quinazolinyl)acetamide, N1-{4-[3,5-Difluoro-4-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,4-Difluoro-3-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,6-Difluoro-3-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,6-Difluoro-4-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,5-Difluoro-4-trifluoromethylphenyl]-1,3-thiazol-2-yl}-2-(1,3-dimethyl-2,4-dioxo-1,2,3,4-tetrahydro-5-quinazolinyl)acetamide, N1-{4-[3,4-Difluoro-5-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,3-Difluoro-5-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,5-Difluoro-3-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,4-Difluoro-5-trifluoromethylphenyl]-1,3-thiazol-2-yl}-2-(1,3-dimethyl-2,4-dioxo-1,2,3,4-tetrahydro-5-quinazolinyl)acetamide;
N1-{4-[3,6-Difluoro-2-trifluoromethylphenyl]-1,3-thiazol-2-yl}-2-(1,3-dimethyl-2,4-dioxo-1,2,3,4-tetrahydro-5-quinazolinyl)acetamide,
N1-{4-[3,4-Difluoro-2-trifluoromethylphenyl]-1,3-thiazol-2-yl}-2-(1,3-dimethyl-2,4-dioxo-1,2,3,4-tetrahydro-5-quinazolinyl)acetamide,
N1-{4-[3,5-Difluoro-2-trifluoromethylphenyl]-1,3-thiazol-2-yl}-2-(1,3-dimethyl-2,4-dioxo-1,2,3,4-tetrahydro-5-quinazolinyl)acetamide,
N1-{4-[4,5-Difluoro-2-trifluoromethylphenyl]-1,3-thiazol-2-yl}-2-(1,3-dimethyl-2,4-dioxo-1,2,3,4-tetrahydro-5-quinazolinyl)acetamide,
N1-{4-[2,3-Difluoro-6-trifluoromethylphenyl]-1,3-thiazol-2-yl}-2-(1,3-dimethyl-2,4-dioxo-1,2,3,4-tetrahydro-5-quinazolinyl)acetamide,
N1-{4-[2,4-Difluoro-6-trifluoromethylphenyl]-1,3-thiazol-2-yl}-2-(1,3-dimethyl-2,4-dioxo-1,2,3,4-tetrahydro-5-quinazolinyl)acetamide,
N1-[4-(4-Difluoromethoxy-3,5-difluorophenyl)-1,3-thiazol-2-yl]-2-(1,3-dimethyl-2,4-dioxo-1,2,3,4-tetrahydro-5-quinazolinyl)propanamide,
N1-{4-[3,5-Difluoro-4-(2,2,2-trifluoroethoxy)phenyl]-1,3-thiazol-2-yl}-2-(1,3-dimethyl-2,4-dioxo-1,2,3,4-tetrahydro-5-quinazolinyl)acetamide,
N1-[4-(3,5-Difluoro-4-methoxyphenyl)-1,3-thiazol-2-yl]-2-(1,3-dimethyl-2,4-dioxo-1,2,3,4-tetrahydroquinazolin-5-yl)acetamide,
N1-[4-(4-Cyclopropylmethoxy-3,5-difluorophenyl)-1,3-thiazol-2-yl]-2-(1,3-dimethyl-2,4-dioxo-1,2,3,4-tetrahydroquinazolin-5-yl)acetamide,
N1-[4-(1H-3-Indolyl)-1,3-thiazol-2-yl]-2-(1,3-dimethyl-2,4-dioxo-1,2,3,4-tetrahydro-5-quinazolinyl)acetamide,
N1-[4-(4-(1-Methyl-3-indolyl)-1,3-thiazol-2-yl]-2-(1,3-dimethyl-2,4-dioxo-1,2,3,4-tetrahydro-5-quinazolinyl)acetamide,
N1-Benzo[d][1,3]thiazol-2-yl]-2-(1,3-dimethyl-2,4-dioxo-1,2,3,4-tetrahydro-5-quinazolinyl)acetamide,
N1-[6-Fluorobenzo[d][1,3]thiazol-2-yl)-2-(1,3-dimethyl-2,4-dioxo-1,2,3,4-tetrahydro-5-quinazolinyl)acetamide,
N1-(5,6-Dimethylbenzo[d][1,3]thiazol-2-yl)-2-(1,3-dimethyl-2,4-dioxo-1,2,3,4-tetrahydro-5-quinazolinyl)acetamide,
N1-[4-(7-chloro-4,5-dihydronaphtho[1,2-d][1,3]-thiazol-2-yl]-2-(1,3-dimethyl-2,4-dioxo-1,2,3,4-tetrahydro-5-quinazolinyl)acetamide,
N1-[3-(4-Chlorophenyl)-1H,5-pyrazolyl]-2-(1,3-dimethyl-2,4-dioxo-1,2,3,4-tetrahydro-5-quinazolinyl)acetamide,
N1-[1-(4-Chlorophenyl)-1H,3-pyrazolyl]-2-(1,3-dimethyl-2,4-dioxo-1,2,3,4-tetrahydro-5-quinazolinyl)acetamide,
N1-[1-(3-Trifluoromethylphenyl)-1H-3-pyrazolyl]-2-(1,3-dimethyl-2,4-dioxo-1,2,3,4-tetrahydro-5-quinazolinyl)acetamide.
N1-[1-(4-Chloro-2-fluorophenyl)-1H-3-pyrazolyl]-2-(1,3-dimethyl-2,4-dioxo-1,2,3,4-tetrahydro-5-quinazolinyl)acetamide,
N1-[5-(4-Bromophenyl)-1,3,4-thadiazol-2-yl]-2-(1,3-dimethyl-2,4-dioxo-1,2,3,4-tetrahydro-5-quinazolinyl)acetamide
and esters thereof, tautomer thereof, stereoisomer thereof, and pharmaceutically acceptable salt thereof.

The present invention also provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present patent application may be associated with a pharmaceutically acceptable excipient (such as a carrier or a diluent) or be diluted by a carrier, or enclosed within a carrier which can be in the form of a capsule, sachet, paper or other container.

The compounds and pharmaceutical compositions of the present invention are useful for modulating TRPA1 receptors, which is related to a variety of disease states.

The present patent application further provides a method of inhibiting TRPA1 receptors in a subject in need thereof by administering to the subject one or more compounds described herein in an amount effective to cause inhibition of such receptor.

DETAILED DESCRIPTION OF THE INVENTION

Definitions

Figure 1:
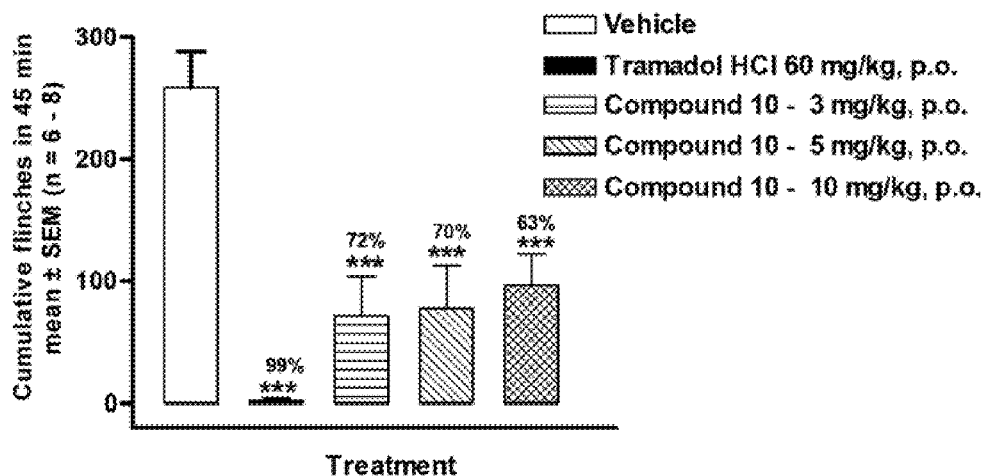
FIG. 1 is a bar graph the effect of Compound 10 on Allyl Isothiocyanate (AITC) induced flinches in rats.

The terms "halogen" or "halo" includes fluorine, chlorine, bromine, or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl(isopropyl), n-butyl, n-pentyl, and 1,1-dimethylethyl (tert-butyl). The term "$C_{1-6}$ alkyl" refers to an alkyl chain having 1 to 6 carbon atoms.

The term "alkenyl" refers to an aliphatic hydrocarbon group containing a carbon-carbon double bond and which may be a straight or branched chain having 2 to about 10 carbon atoms, e.g., ethenyl, 1-propenyl, 2-propenyl(allyl), iso-propenyl, 2-methyl-1-propenyl, 1-butenyl, and 2-butenyl.

The term "alkynyl" refers to a straight or branched chain hydrocarbyl radical having at least one carbon-carbon triple bond, and having 2 to about 12 carbon atoms (with radicals having 2 to about 10 carbon atoms being preferred), e.g., ethynyl, propynyl, and butynyl.

The term "alkoxy" refers to a straight or branched, saturated aliphatic hydrocarbon radical bonded to an oxygen atom that is attached to a core structure. Examples of alkoxy groups include but are not limited to methoxy, ethoxy, propoxy, isopropoxy, butoxy, isobutoxy, tert-butoxy, pentoxy, 3-methyl butoxy, and the like.

The term "haloalkyl" and "haloalkoxy" means alkyl or alkoxy, as the case may be, substituted with one or more halogen atoms, where alkyl and alkoxy groups are as defined above. The term "halo" is used herein interchangeably with the term "halogen" means F, Cl, Br, or I. Examples of "haloalkyl" include but are not limited to trifluoromethyl, difluoromethyl, 2,2,2-trifluoroethyl, pentafluoroethyl, pentachloroethyl 4,4,4-trifluorobutyl, 4,4-difluorocyclohexyl, chloromethyl, dichloromethyl, trichloromethyl, 1-bromoethyl, and the like. Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy, 1-bromoethoxy and the like.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronapththyl, adamantyl and norbornyl groups, bridged cyclic groups or sprirobicyclic groups, e.g., spiro(4,4) non-2-yl.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "cycloalkylalkoxy" is used to denote alkoxy substituted with cycloalkyl, wherein 'alkoxy' and 'cycloalkyl' are as defined above (either in the broadest aspect or a preferred aspect). Examples of cycloalkylalkoxy groups include cyclopropylmethoxy, 1- or or 2-cyclopropylethoxy, 1-, 2- or 3-cyclopropylpropoxy, 1-, 2-, 3- or 4-cyclopropylbutoxy, cyclobutylmethoxy, 1- or 2-cyclobutylethoxy, 1-, 2- or 3-cyclobutylpropoxy, 1-, 2-, 3- or 4-cyclobutylbutoxy, cyclopentylmethoxy, 1- or 2-cyclopentylethoxy, 1-, 2- or 3-cyclopentylpropoxy, 1-, 2-, 3- or 4-cyclopentylbutoxy, cyclohexylmethoxy, 1- or 2-cyclohexylethoxy and 1-, 2- or 3-cyclohexylpropoxy. Preferably, 'cycloalkylalkoxy' is $(C_{1-6})$cycloalkyl-$(C_{1-6})$alkoxy.

The term "cycloalkenyl" refers to a cyclic ring-containing radical having 3 to about 8 carbon atoms with at least one carbon-carbon double bond, such as cyclopropenyl, cyclobutenyl, and cyclopentenyl.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (ie, attached or formed) by having two adjacent atoms in common (i.e., shared) with the first ring. The term "fused" is equivalent to the term "condensed". The term "aryl" embraces aromatic radicals such as phenyl, naphthyl, tetrahydronaphthyl, indane and biphenyl.

The term "arylalkyl" refers to an aryl group as defined above directly bonded to an alkyl group as defined above, e.g., —$CH_2C_6H_5$ or —$C_2H_5C_6H_5$.

The term "heterocyclic ring" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoqinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heterocyclic ring radical may be attached to the main structure at any heteroatom or carbon atom that results in the creation of a stable structure.

The term "heterocyclyl" refers to a heterocyclic ring radical as defined above. The heterocyclyl ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —(=N—$N(R^x)R^y$), —$NR^xC(O)OR^y$, —$NR^xR^y$, —$NR^xC(O)R^y$, —$NR^xC(S)R^y$, —$NR^xC(S)NR^yR^z$, —$SONR^xR^y$, —$SO_2NR^xR^y$, —$OR^x$, —$OR^xC(O)NR^yR^z$, —$OR^xC(O)OR^y$, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^y$, —$R^xOC(O)R^y$, —$SR^x$, —$SOR^x$, —$SO_2R^x$, and —$ONO_2$, wherein $R^x$, $R^y$ and $R^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. According to one embodiment, the substituents in the aforementioned "substituted" groups cannot be further substituted. For example, when the substituent on "substituted alkyl" is "substituted aryl", the substituent on "substituted aryl" cannot be "substituted alkenyl".

The term "treating" or "treatment" of a state, disorder or condition includes: (a) preventing or delaying the appearance or clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof, or (c) relieving the disease, i.e., causing regression of the state, disorder or condition or at least one of its clinical or subclinical symptoms.

The benefit to a subject to be treated is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The compound described in the present patent application may form salts. Non-limiting examples of pharmaceutically acceptable salts forming part of this patent application include salts derived from inorganic bases, salts of organic bases, salts of chiral bases, salts of natural amino acids and salts of non-natural amino acids. Certain compounds of present patent application are capable of existing in stereoisomeric forms (e.g. diastereomers and enantiomers). With respect to the overall compounds described by the Formulas (I), (Ia) and (Ib), the present patent application extends to these stereoisomeric forms and to mixtures thereof To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated.

Pharmaceutical Compositions

The pharmaceutical composition of the present patent application includes at least one compound described herein and at least one pharmaceutically acceptable excipient (such as a pharmaceutically acceptable carrier or diluent). Preferably, the pharmaceutical composition includes the compound(s) described herein in an amount sufficient to inhibit TRPA1 in a subject (e.g., a human). The inhibitory activity of compounds falling within the formula (I) may be measured by an assay provided below.

The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmetic pressure, buffers, sweetening agents, flavoring agents, colorants, or any combination of the foregoing. The pharmaceutical composition may be formulated so as to provide quick, sustained, or delayed release of the active ingredient after administration to the subject by employing procedures known in the art.

The pharmaceutical compositions may be prepared by techniques known in the art, e.g., as described in Remington: The Science and Practice of Pharmacy, $20^{th}$ Ed., 2003 (Lippincott Williams & Wilkins). For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Non-limiting examples of carriers for tablets, dragees, or capsules include lactose, cornstarch, and/or potato starch. A syrup or elixir can be used in cases where a sweetened vehicle can be employed.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Treatment

The compounds and pharmaceutical compositions of the present invention can be administered to treat any disorder, condition, or disease treatable by inhibition of TRPA1. For instance, the compounds and pharmaceutical compositions of the present invention are suitable for treatment or prophylaxis of the following diseases, conditions, and disorders mediated or associated with the activity of TRPA1 receptors: pain, chronic pain, complex regional pain syndrome, neuropathic pain, postoperative pain, rheumatoid arthritic pain, osteoarthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, chronic obstructive pulmonary disease (COPD), inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, eczema, emesis, stomach duodenal ulcer and pruritus. The connection between therapeutic effect and inhibition of TRPA1 is illustrated, for example, in Story G M et al, *Cell*, (2003), 112, 819-829; McMahon S B and Wood J N, *Cell*, (2006), 124, 1123-1125; Voorhoeve P M et al, *Cell*, (2006), 124, 1169-1181; Wissenbach U, Niemeyer B A and Flockerzi V, *Biology of the Cell*, (2004), 96, 47-54; Dayne Y O, Albert Y H & Michael X, *Expert Opinion on Therapeutic Targets* (2007), 11(3), 391-401 and the references cited therein.

Pain can be acute or chronic. While acute pain is usually self-limiting, chronic pain persists for 3 months or longer and can lead to significant changes in a patient's personality; lifestyle, functional ability and overall quality of life (K. M. Foley, *Pain*, in Cecil Textbook of Medicine; J. C. Bennett & F. Plum (eds.), 20th ed. (1996) 100-107). The sensation of pain can be triggered by any number of physical or chemical stimuli and the sensory neurons which mediate the response to this harmful stimulus are termed as "nociceptors". Nociceptors are primary sensory afferent (C and Aδ fibers) neurons that are activated by a wide variety of noxious stimuli including chemical, mechanical, thermal, and proton (pH<6) modalities. Nociceptors are the nerves which sense and respond to parts of the body which suffer from damage. They signal tissue irritation, impending injury, or actual injury. When activated, they transmit pain signals (via the peripheral nerves as well as the spinal cord) to the brain.

Chronic pain can be classified as either nociceptive or neuropathic. Nociceptive pain includes tissue injury-induced pain and inflammatory pain such as that associated with arthritis. Neuropathic pain is caused by damage to the sensory nerves of the peripheral or central nervous system and is maintained by aberrant somatosensory processing. The pain is typically well localized, constant, and often with an aching or throbbing quality. Visceral pain is the subtype of nociceptive pain that involves the internal organs. It tends to be episodic and poorly localized. Nociceptive pain is usually time limited, meaning when the tissue damage heals, the pain typically resolves (arthritis is a notable exception in that it is not time limited).

General Method of Preparation

The compounds described herein, including compounds of general formula (I), (Ia) and (Ib), and specific examples are prepared using techniques known to one skilled in the art through the reaction sequences depicted in schemes 1-9 as well as by other methods. Furthermore, in the following schemes, where specific acids, bases, reagents, coupling agents, solvents, etc. are mentioned, it is understood that other suitable acids, bases, reagents, coupling agents etc. may be used and are included within the scope of the present invention. The compounds obtained by using the general reaction sequences may be of insufficient purity. These compounds can be purified by using any of the methods for purification of organic compounds known to persons skilled in the art, for example, crystallization or silica gel or alumina column chromatography using different solvents in suitable ratios. All possible stereoisomers are envisioned within the scope of this invention. The variable X in the schemes below refers to a leaving group unless otherwise indicated. All variables are defined as above unless otherwise indicated.

All the tetrahydroquinazolinedione acetic acids of the formula (9a) to (9d) were prepared according to the procedure described in schemes 1-6. However, these intermediates can be prepared by alternative methods and such methods are within the scope of the present invention.

Tetrahydroquinazolinedione acetic acids of the formula (9a) (wherein $R^1$ and $R^2$ are the same) used for the synthesis of compounds of the present invention were prepared as described in Scheme 1. 2-amino-6-nitrobenzoic acid of the formula (1) was treated with urea in acetic acid at elevated temperature to give 5-nitroquinazolinedione of the formula (2). The compound of the formula (2) is N-alkylated with an excess of alkyl halide (e.g., $R^1X$ or $R^2X$) in the presence of a suitable base to give the symmetrically dialkylated compound of the formula (3). The nitro group reduction of intermediate (3) with an appropriate reducing agent such as iron and ammonium chloride in aqueous ethanol or iron and acetic acid gives the amino derivative of the formula (4). Similar approaches have been described by: (a) Mahaood; Schaffner; P. V. L.; *Org. Synth.*, (1943), coll. vol. 2, 160 (b) Mahaood; Schaffner; P. V. L.; et al. in *Org. Synth* (1931), 11, 132 and (c) Banik, B. K.; Banik, I.; Becker, F. F. *Org. Synth.* (2005), 81,188. The amine (4) on diazotization followed by halide substitution with a metal halide (5) such as potassium iodide affords a halide derivative of the formula (6) where X is halogen. Similar references have been reported by Hannaford, A. J.; Smith, P. W. G.; Tatchell, A. R. in Vogel's Textbook of Practical Organic Chemistry, (2006), 5th Ed., 890-897. The aryl halide of formula (6) on reaction with an allylboronic acid pinacol ester of the formula (7) preferably in the presence of Pd(0) catalyst gives the allyl quinazolinedione of the formula (8). A similar Suzuki-Miyaura coupling procedure is described by Kotha, S. et al. in *Synlett*. (2005), 12, 1877-1890. Oxidative cleavage of the terminal olefinic bond of intermediate (8) using, for example, sodium metaperiodate in the presence of catalytic amounts of ruthenium (III) chloride (Sharpless, K. B. et al. in *J. Org. Chem.*, (1981), 3936-3938) gives the tetrahydroquinazolinedione acetic acid derivative of the formula (9a).

Scheme 1

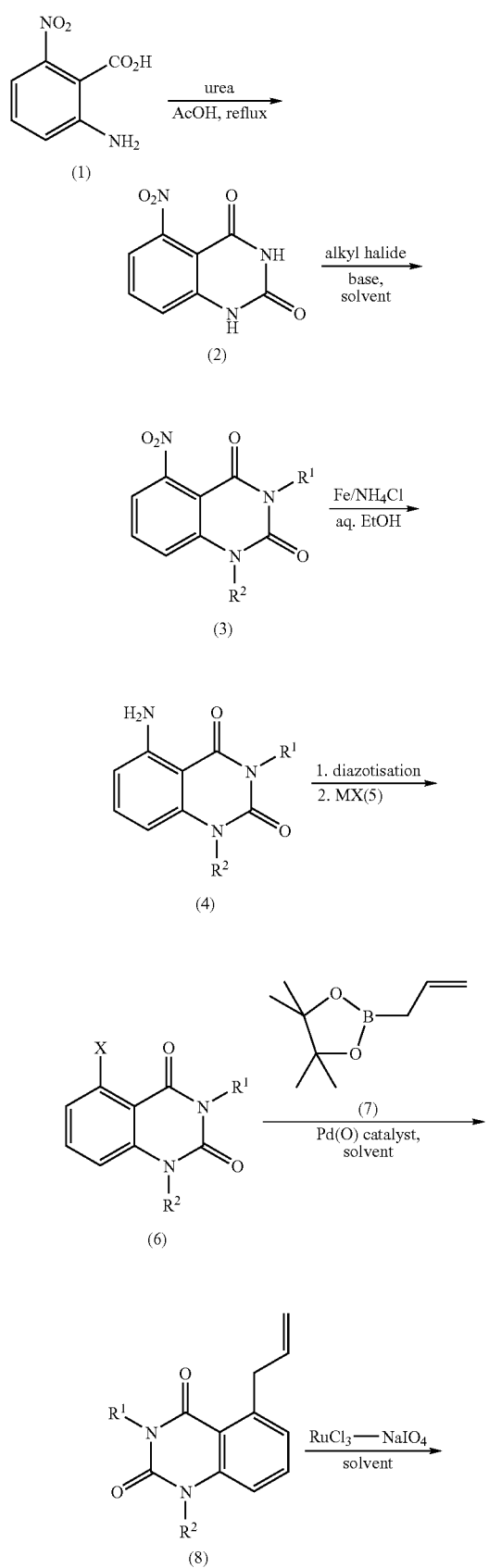

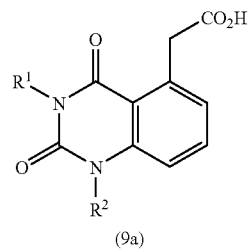

Unsymmetrically substituted tetrahydroquinazolinedione acetic acids of the formula (9b) (wherein $R^1$ and $R^2$ are different) were prepared as described in the Scheme 2. Thus, 2-amino-6-nitrobenzoic acid of the formula (1) is coupled with an amine of the formula (10) in the presence of a suitable coupling agent to give the amide of formula (11) (wherein $R^1$ is alkyl), which was then treated with triphosgene in a suitable solvent to afford the quinazolinedione of formula (12). The N-alkylation of the compound of formula (12) with an alkylating agent of the formula (13) gives the unsymmetrical nitro quinazolinedione of formula (14) (wherein $R^2$ is alkyl or cycloalkylalkyl). The nitro group reduction of compound of formula (14) followed by diazotization and halogen exchange affords the compound of the formula (6a) (wherein X is halogen). Palladium (0) catalyzed coupling of compound of the formula (6a) with the allylboronic acid ester of formula (7) followed by oxidative cleavage as described in Scheme 1 gives the unsymmetrically substituted tetrahydroquinazolinedione acetic acid derivative of the formula (9b).

Scheme 2

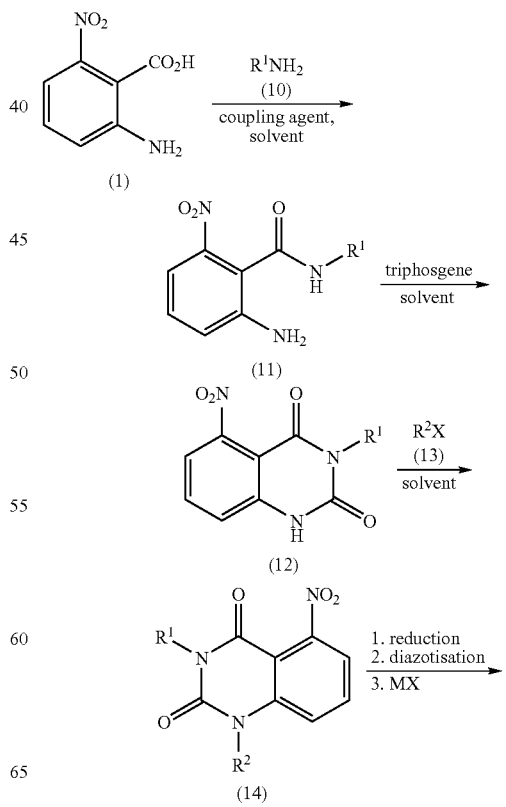

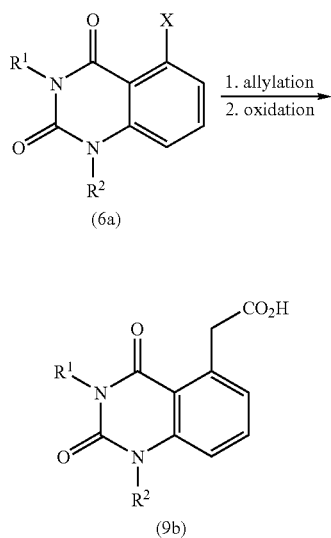

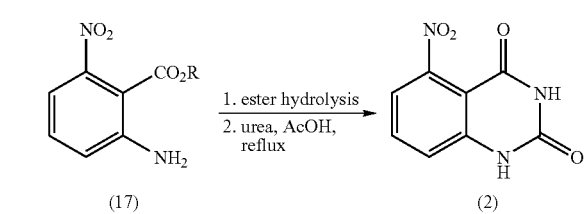

An approach for the synthesis of key intermediate (2) is shown below in Scheme 3. Thus, 3-nitro phthalic anhydride of formula (15) is treated with an alcohol to give the nitrophthalic acid ester of formula (16) (wherein R is alkyl). Conversion of the compound of formula (16) to the corresponding acid chloride followed by reaction with sodium azide in DMF gives the corresponding azido derivative, which on Curtius reaction gives the amino ester of formula (17). Hydrolysis of ester (17) followed by its reaction with urea in refluxing acetic acid gives 5-nitroquinazolinedione of formula (2) in good yield.

An alternative approach for the introduction of allyl substitution at the 5-position of quinazolinedione is shown in Scheme 4, In this approach, an amine of formula (18) is directly treated with allyl bromide and an alkyl nitrile such as tert-butyl nitrite to give the allyl derivative of formula (19) (Frejd, T. et al. in *J. Org. Chem.* (2003), 68, 1911-1918), which is finally cleaved to give the tetrahydroquinazolinedione acetic acid derivative of formula (9b).

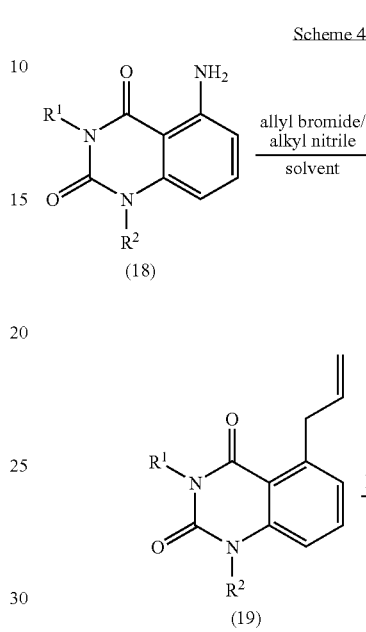

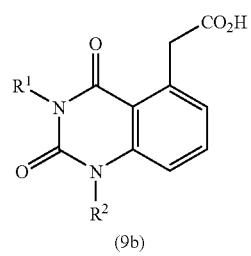

Scheme 5 shows yet another approach for the synthesis of tetrahydroquinazolinedione acetic acid derivatives. Thus, the amino ester of formula (17) is directly allylated using an alkyl nitrile in a suitable solvent such as acetonitrile to give the allyl derivate of formula (20) (Frejd, T. et al. in *J. Org. Chem.* (2003), 68, 1911-1918), which is then reduced by using an appropriate reducing agent such as iron and ammonium chloride in aqueous ethanol or iron and acetic acid to give the amino ester of formula (21). The compound of formula (21) is hydrolyzed and the resulting acid was treated with urea in refluxing acetic acid to give the allyl quinazolinedione of the formula (22). The allyl quinazolinedione of formula (22) can be oxidatively cleaved to the corresponding quinazolinedione acetic acid of the formula (9c) by a method as described in Scheme 1. Alternatively, the compound of formula (22) is first alkylated with an alkyl halide (e.g., $R^1X$ or $R^2X$) to give the compound of the formula (8), which was then oxidatively cleaved to the tetrahydroquinazolinedione acetic acid derivative of formula (9a).

Scheme 5

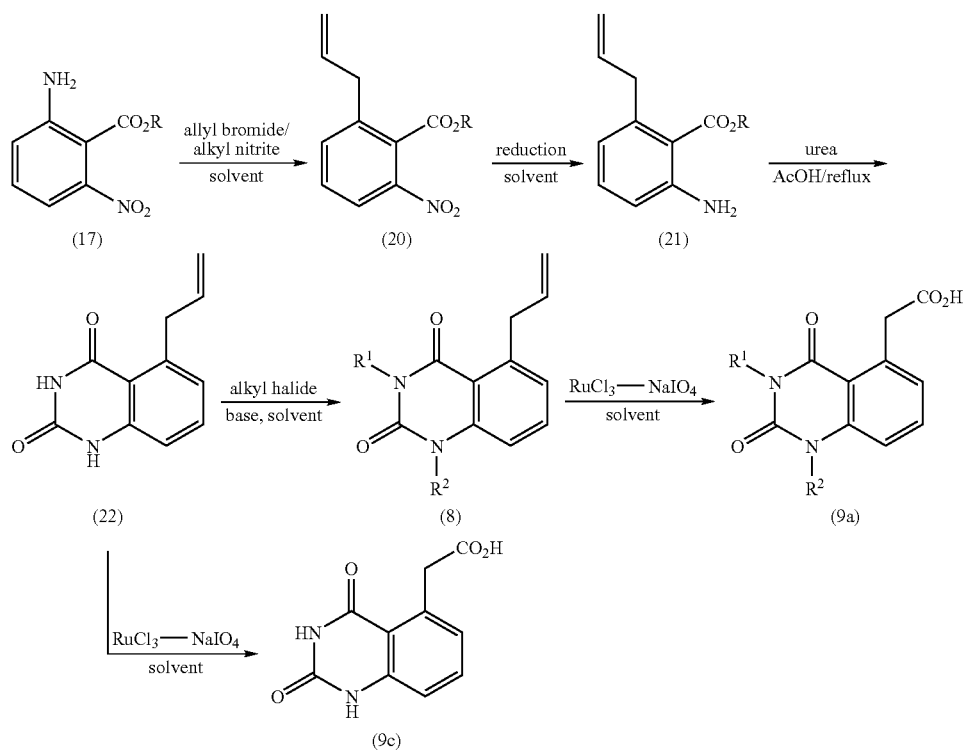

Synthesis of tetrahydroquinazolinedion acetic acid derivatives of formula (9d) bearing additional substituents $R^3$ and $R^4$ at the benzylic position is given in Scheme 6. Tetrahydroquinazolinedione acetic acid derivative of formula (9a) or (9b) on esterfication gives the compound of the formula (23), which on alkylation with an appropriate alkyl halide in the presence of a strong base such as sodium hydride gives the compound of the formula (24). The ester of formula (24) is then hydrolyzed back to tetrahydroquinazolinedion acetic acid of the formula (9d).

Scheme 6

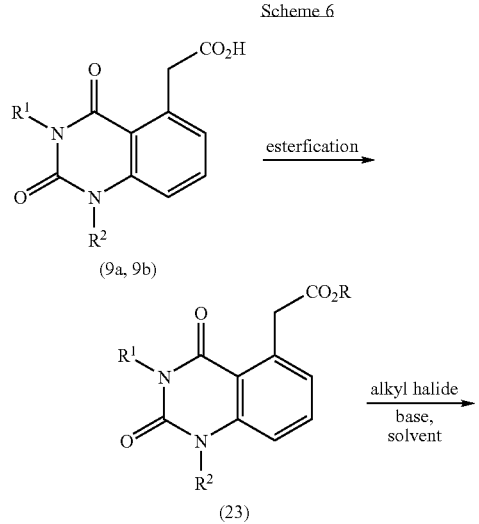

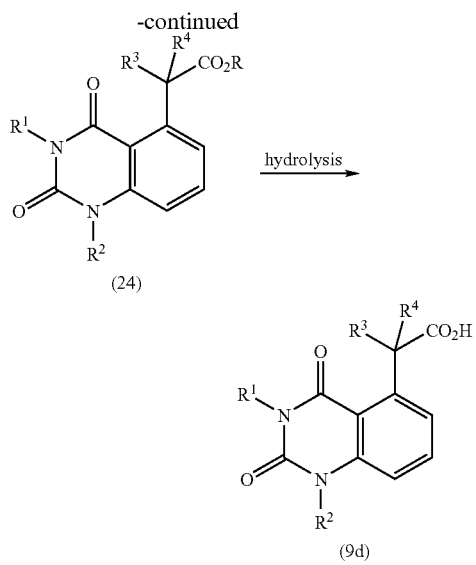

All the biaryl amine derivatives used for the synthesis of compounds of the invention were purchased from commercial sources. 2-aminobenzothiazoles were purchased from Aldrich Chemical Company. Most of the 2-amino-4-phenyl-1,3-thiadiazoles were also purchased from commercial sources.

Selected 2-amino-4-phenylbenzothiazoles of the formula (30a) were prepared from acetophenones of the formula (29) as shown in Scheme 7 using known approaches. Certain di- and tri-substituted acetophenones were not commercially available and they were prepared from the corresponding benzoic acid derivative of formula (25) in three steps. The acid of formula (25) was converted to the corresponding acid chloride of formula (26) using oxalyl chloride in the presence of catalytic amounts of DMF in dry dichloromethane. Alternatively, this transformation can be carried out using excess thionyl chloride. The acid chloride of formula (26) was converted to the corresponding Weinerb amide of formula (28) by treating with N,O-dimethylhydroxylamine hydrochloride of formula (27) in the presence of a suitable base such as triethylamine. The addition of methyl magnesium iodide to the Weinreb amide of formula (28) afforded the acetophenone derivative of formula (29).

Conversion of acetophenone derivative of formula (29) to 2-amino-4-substituted aryl thiazole of the formula (30a) can be effected by two complementary approaches as shown in Scheme 7. In the first case, the acetophenone was converted to the corresponding phenacyl bromide, which in turn was reacted with thiourea in refluxing tetrahydrofuran. Alternatively, the acetophenone derivative of formula (29) can be converted to 2-amino-4-phenyl thiazole in one step by its reaction with thiourea and iodine in refluxing ethanol (Carroll, K. et al. *J. Am. Chem. Soc.* (1950), 3722 and Naik, S. J.; Halkar, U. P., *ARKIVOC* (2005) xiii, 141-149).

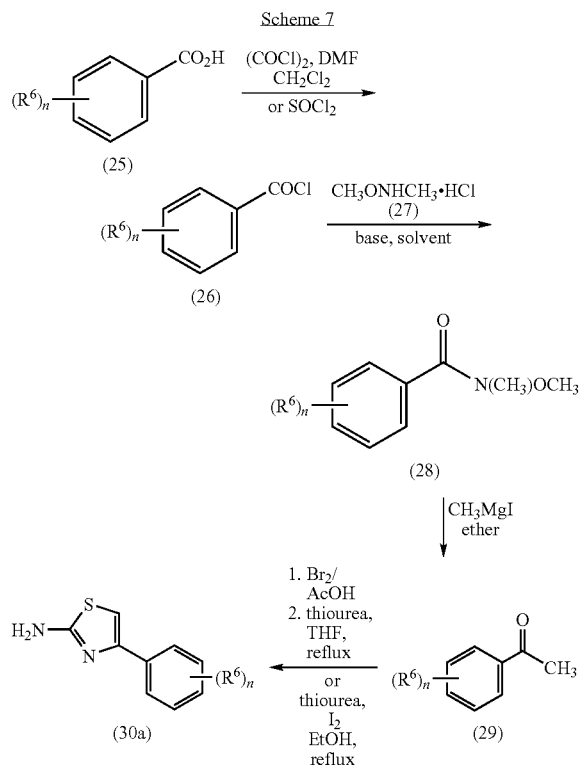

Some of the 5-amino-3-phenylpyrazoles used for the synthesis of compounds of the present invention were commercially available. Commercially unavailable 3-amino-1-arylpyrazoles were prepared as shown in Scheme 8. Reaction of the phenylhydrazine derivative of formula (31) with acrylonitrile in the presence of a suitable base such as sodium ethoxide in refluxing ethanol affords the dihydro derivative of formula (32). Intermediate (32) on oxidation with N-bromosuccinamide as described by Duflin, G. F. et al. *J. Chem. Soc.* (1954), 408-415, gives 3-amino-1-arylpyrazoles derivative of formula (30b).

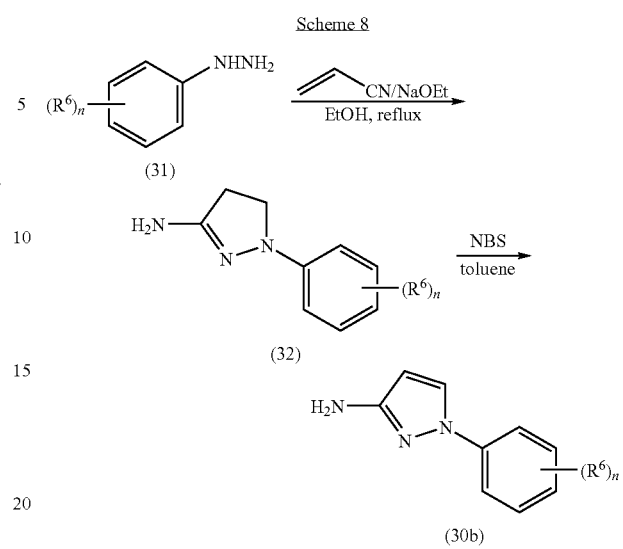

Compounds of the present invention were prepared by coupling tetrahydroquinazolinedione acetic acid derivatives of the formula (9a) to (9d) with various amines such as arylamines, diphenylamines, heteroarylamines, 2-amino-4-arylthiazoles, 2-aminobenzothiazoles, dihydronaphtho[1,2-d]thiazole-2-ylamines, 2-amino-4-indazolyl-thiazoles, 3-amino-1-arylpyrazoles, 5-amino-3-phenylpyrazoles, 2-amino-5-arylthiadia-zoles etc.

The coupling reaction of tetrahydroquinazolinedione acetic acid derivatives of the formula (9a) to (9d) with the various amines of formula (30), wherein $R^5$ is hydrogen can be effected as shown in Scheme 9. The coupling reaction can be mediated by a suitable coupling agent such as EDCI.HCl (1-(3-dimethylaminopropyl)-3-ethylcarbodiimide hydrochloride) in the presence of a suitable activating agent such as 1-hydroxybenzotriazole and a base in a suitable solvent or a mixture of solvents to afford compounds of the present invention (Formula (I)).

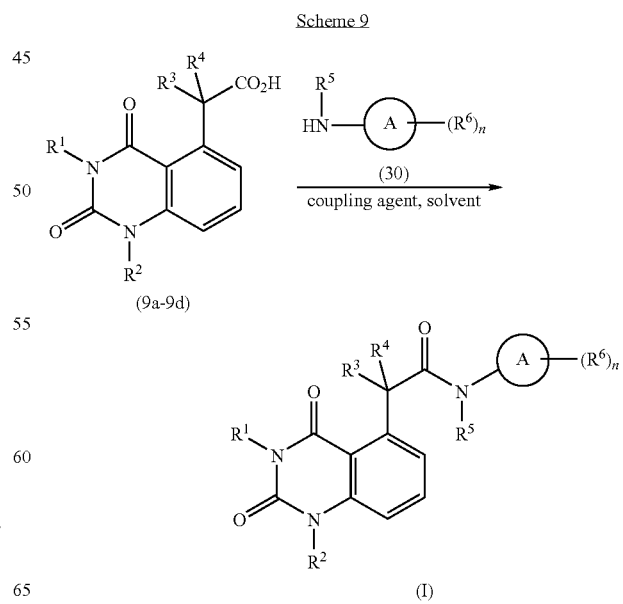

EXPERIMENTAL

Unless otherwise stated, work-tip implies the following operations: distribution of the reaction mixture between the organic and aqueous phase, separation of layers, drying the organic layer over sodium sulfate, filtration and evaporation of the organic solvent. Purification, unless otherwise mentioned, implies purification by silica gel chromatographic techniques, generally using ethyl acetate/petroleum ether mixture of a suitable polarity as the mobile phase. The following abbreviations are used in the text: DMSO-$d_6$: hexadeuterodimethyl sulfoxide; DMF: N,N-dimethylformamide, J: coupling constant in units of Hz, RT: room temperature (22-26° C.). aq.: aqueous AcOEt: ethyl acetate; equiv.: equivalents.

Intermediates

All 1,2,3,4-tetrahydroquinazolinedione acetic acid derivatives of the general formula (9a) to (9d), used for the preparation of compounds of the present invention, were prepared according to the synthetic schemes provided in 'General Methods of Preparation'. However, these intermediates may be prepared by alternative approaches reported in the literature or by methods known to people skilled in the art of organic synthesis. Detailed experimental procedures for the synthesis of intermediates are given below.

Some of aryl amines and heteroaryl amines used for the preparation of compounds of the present invention were purchased from commercial sources. All the 2-aminobenzothiazoles and 2-amino-5-phenylthiadiazole were purchased from Aldrich. The several of the 2-amino-4-aryl thiazoles were also commercial available. The commercially unavailable 2-amino-4-aryllthiazoles were prepared by known literature methods starting from either substituted acetophenone or substituted benzoic acid as shown in 'General Synthetic Methods'

Intermediate 1

2-(1,3-Dimethyl-2,4-dioxo-1,2,3,4-tetrahydro-quinazolinyl)acetic acid

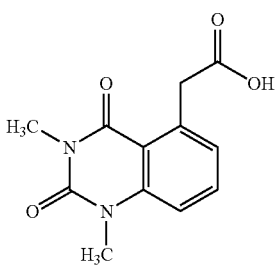

Step 1: 5-Nitro-1,2,3,4-tetrahydro-2,4-quinazolinedione: A mixture of 2-amino-6-nitro-benzoic acid (60 g, 329 mmol) and urea (257.3 g, 4285 mmol) in acetic acid (1.65 lit.) was heated to reflux for 24 h. The acetic acid was evaporated under reduced pressure and the residue obtained was diluted with water (2.5 lit). The solid product separated out was filtered and washed with water. The product was collected and dried in an air oven to give 44 g of the product as a yellow solid; $^1$H NMR (δ ppm, DMSO-$d_6$, 300 MHz): 11.58 (br. s, 1H); 11.55 (br.s, 1H); 7.76 (t, J=8.4, 1H); 7.41 (d, J=7.8, 1H); 7.32 (d, J=8.4, 1H).

Step 2: 5-Nitro-1,3-dimethyl-1,2,3,4-tetrahydro-2,4-quinazolinedione: A solution of Step 1 intermediate (40 g, 193 mmol) in dry DMF (386 ml) was added anhydrous $K_2CO_3$ (133.51 g, 966 mmol) and the mixture was stirred at room temperature for 30 min. Methyl iodide (40 ml, 636 mmol) was added slowly with stirring and further stirred at room temperature for 24 h. The reaction mixture was diluted with water (1.5 lit) and the solid precipitated out was filtered, washed with water and dried to give 41 g of the product as yellow solid; $^1$H NMR (δ ppm, DMSO-$d_6$, 300 MHz): 7.89 (t, J=8.4, 1H); 7.67 (d, J=8.7, 1H); 7.54 (d, J=7.8, 1H); 3.54 (s, 3H); 3.24 (s, 3H). MS (m/z): 236.20 ([M+H]$^+$).

Step 3: 5-Amino-1,3-dimethyl-1,2,3,4-tetrahydro-2,4-quinazolinedione: To a stirred suspension of Step 2 intermediate (40 g, 170 mmol) in 25% aqueous ethanol (1.3 lit) was added iron powder (47.5 g, 851 g atom) and ammonium chloride (910 mg, 17 mmol) and the mixture was refluxed for 6 h. The mixture was cooled to room temperature and filtered through a celite bed. The filtrate was collected and concentrated under reduced pressure to give 33 g of the amino compound as off-white solid; $^1$H NMR (δ ppm, DMSO-$d_6$, 300 MHz): 7.34-7.23 (m, 3H); 6.45 (d, J=8.1, 1H); 6.32 (d, J=8.4, 1H); 3.39 (s, 3H); 3.23 (s, 3H). MS (m/z): 206.40 ([M+H]$^+$).

Step 4: 5-Iodo-1,3-dimethyl-1,2,3,4-tetrahydro-2,4-quinazolinedione: To a stirred solution of Step 3 intermediate (30.3 g, 0.147 mol) in acetonitrile 720 ml) was added p-toluenesulfonic acid monohydrate (106.7 g, 560 mmol) and the mixture was stirred for 30 min to result a solid suspension. After 1 h at room temperature, the mixture was cooled (10° C.) and a solution of sodium nitrite (25.46 g 369 mmol) and potassium iodide (70.85 g, 442 mmol) in water (90 ml) were added drop-wise to result a brown solution. The mixture was further stirred for 1 h at room temperature and diluted with water (100 ml). The pH of the solution was adjusted to 7.0-8.0 by addition of saturated sodium bicarbonate solution. The solution was treated with aqueous sodium thiosulfate solution to remove free iodine. The solid product separated out was collected by filtration and dried to give the crude product. The product was further purified by silica gel column chromatography using 4% ethyl acetate in petroleum ether to give 41 g of the product as a white solid; $^1$H NMR (δ ppm, DMSO-$d_6$, 300 MHz): 7.88 (d, J=7.2, 1H); 7.45 (d, J=8.4, 1H); 7.34 (t, J=8.4, 1H); 3.48 (s, 3H); 3.26 (s, 3H). MS (m/z): 317.24 ([M+H]$^+$).

Step 5: 5-Allyl-1,3-dimethyl-1,2,3,4-tetrahydro-2,4-quinazolinedione

To a stirred solution of Step 4 intermediate (40 g, 126 mmol) in 1,4-dioxane (1.3 lit) was added cesium fluoride (38.3 g, 252 mmol) and allylboronic acid pinacol ester (42.5 ml, 225 mmol) under nitrogen atmosphere and the mixture was degassed for 10 min. Tetrakis(triphenylphosphine)palladium(0) (14.46 g, 12 mmol) catalyst was added and the mixture was stirred at 100° C. for 20 h under nitrogen atmosphere. The mixture was diluted with water (500 ml) and extracted with ethyl acetate (3×500 ml). The combined extracts were concentrated and the residue obtained was purified by silica gel column chromatography to give 26.5 g of the product as an off-white solid; $^1$H NMR (δ ppm, CDCl$_3$, 300 MHz): 7.54 (t, J=7.8, 1H); 7.08 (t, J=6.9, 2H); 6.18-6.00 (m, 1H); 5.06-4.95 (m, 2H); 4.04 (d, J=6.3, 2H); 3.60 (s, 3H); 3.45 (s, 3H). MS (m/z): 231.37 ([M+H]$^+$).

Step 6: 2-(1,3-Dimethyl-2,4-dioxo-1,2,3,4-tetrahydroquinazolinyl)acetic acid: To a stirred solution of Step 5 intermediate (26 g, 113 mmol) in a 1:3:3 mixture of water, acetonitrile and carbon tetrachloride (560 ml) at room temperature was added sodium metaperiodate (145 g, 678 mmol) and ruthenium(III) chloride trihydrate (468 mg, 2.6 mmol). The biphasic mixture was stirred vigorously at room temperature for 24 h. The mixture was cooled and filtered. The solid containing the product was refluxed in ethyl acetate and the hot mixture is filtered. The filtrate containing the product was evaporated to give 16.5 g of the product as an off-white solid; $^1$H NMR (δ ppm, DMSO-d$_6$, 300 MHz): 12.06 (br. s, 1H); 7.64 (t, J=8.4, 1H); 7.37 (d, J=8.4, 1H); 7.11 (d, 7.5, 1H); 4.04 (s, 2H); 3.51 (s, 3H); 3.25 (s, 3H). MS (m/z): 249.10 ([M+H]$^+$).

Intermediate 2

2-(1,3-Diethyl-2,4-dioxo-1,2,3,4-tetrahydro-quinazolinyl)acetic acid

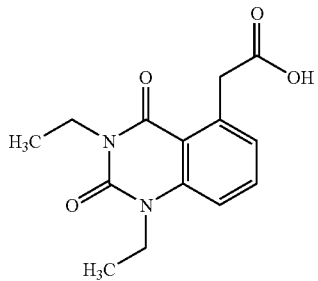

This compound was prepared in 6 steps by following the procedure described for the preparation of Intermediate 1, except for the use of ethyl bromide in the place of methyl iodide in the alkylation step. The compound was isolated as a white solid, $^1$H NMR (δ ppm, DMSO-d$_6$, 300 MHz): 12.06 (br. s, 1H); 7.64 (t, J=7.8, 1H); 7.43 (d, J=8.4, 1H); 7.10 (d, 7.2, 1H); 4.15 (q, J=6.9, 2H); 4.04 (s, 2H); 3.92 (q, J=6.9, 2H); 1.21 (t, J=6.9, 3H); 1.11 (t, J=6.9, 3H).

Intermediate 3

2-(1,3-Dipropyl-2,4-dioxo-1,2,3,4-tetrahydro-quinazolinyl)acetic acid

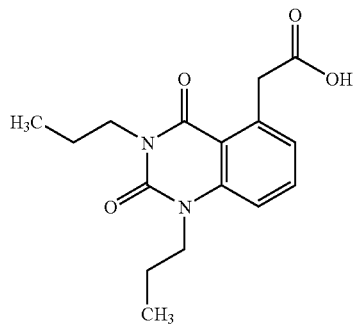

This compound was prepared in 6 steps by following the procedure described for the preparation of Intermediate 1, except for the use of propyl bromide in the place of methyl iodide in the alkylation step. The compound was isolated as a white solid, $^1$H NMR (δ ppm, DMSO-d$_6$, 300 MHz): 12.02 (br s, 1H); 7.64 (t, J=7.8, 1H); 7.43 (d, J=8.7, 1H); 7.12 (d, J=7.5, 1H); 4.10-4.00 (m, 4H); 3.85 (t, J=7.5, 2H); 1.66-1.50 (m, 4H); 0.94 (t, J=7.2, 3H); 0.86 (t, J=7.2, 3H).

Intermediate 4

2-(3-Cyclopropylmethyl-1-methyl-2,4-dioxo-1,2,3,4-tetrahydroquinazolinyl)acetic acid

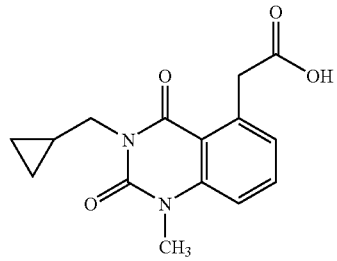

Step 1: N1-Cyclopropylmethyl-2-amino-6-(nitro-benzamide: To a stirred solution of 6-nitro anthranilic acid (10 g, 54 mmol) in dry DMF (100 ml), BOP (benzotriazole-1-yl-oxy-tris-(dimethylamino)-phosphonium hexafluorophosphate) reagent (25.49 g, 57 mmol), cyclopropylmethyl amine hydrochloride (5.91 g, 54 mmol) and triethylamine (19.30 ml, 137 mmol) were added and stirred at room temperature for overnight. The mixture was quenched with water, solid obtained was filtered, washed with water and dried to give 10.7 g of the product as off white solid, $^1$H NMR (δ ppm, DMSO-d$_6$, 300 MHz): 8.53 (br s, 1H); 7.23 (t, J=7.8, 1H); 7.15 (d, J=7.8, 1H); 7.00 (d, J=7.8, 1H); 5.49 (br s, 2H); 3.05 (t, J=6.3, 2H); 1.04-0.96 (br s, 1H); 0.46-0.38 (m, 2H); 0.19 (d, J=4.8, 2H).

Step 2: 5-Nitro-3-cyclopropylmethyl-1,2,3,4-tetrahydro-2,4-quinazolinedione: A solution of Step 1 intermediate (10.5 g, 95 mmol) in dry tetrahydrofuran was added triphosgene (14 g, 47 mmol) and the reaction mixture refluxed for overnight. The mixture was cooled to room temperature, poured into water and extracted with ethyl acetate. The combined organic extracts were washed with brine, dried over anhydrous sodium sulfate. The evaporation of solvent gave 9.5 g of product as off-white solid; $^1$H NMR (δ ppm, DMSO-d$_6$, 300 MHz): 11.88 (s, 1H); 7.79 (t, J=7.5, 1H); 7.46 (d, J=7.8, 1H); 7.35 (d, J=8.1, 1H); 3.71 (d, J=6.9, 2H); 1.23-1.04 (br s, 1H); 0.46-0.41 (m, 2H); 0.39-0.22 (m, 2H).

Step 3: 5-Nitro-3-cyclopropylmethyl-1-methyl-1,2,3,4-tetrahydro-2,4-quinazolinedione: A solution of Step 2 intermediate (5 g, 19.15 mmol) in dry DMF (56 ml) was added anhydrous K$_2$CO$_3$ (3.17 g, 22.98 mmol) and the mixture was stirred at room temperature for 30 min. Methyl iodide (1.43 ml, 22.98 mmol) was added drop-wise and the mixture was further stirred at room temperature for 24 h. The reaction mixture was diluted with water (100 ml) and the solid precipitated out was filtered and washed with water and dried to give 5.5 g of the product as off white solid; $^1$H NMR (δ ppm, DMSO-d$_6$, 300 MHz): 7.90 (t, J=7.8, 1H); 7.66 (d, J=8.7, 1H); 7.55 (d, J=7.8, 1H); 3.76 (d, J=7.2, 2H); 3.55 (s, 3H); 1.20-1.10 (m, 1H); 0.47-0.40 (m, 2H); 0.35-0.28 (m, 2H).

Step 4: 5-Amino-3-cyclopropylmethyl-1-methyl-1,2,3,4-tetrahydro-2,4-quinazolinedione: To a stirred suspension of Step 3 intermediate (5 g, 18.18 mmol) in 25% aqueous ethanol (140 ml) was added iron powder (5.07 g, 90.90 g atom) and ammonium chloride (97 mg, 1.81 mmol) and the mixture was refluxed for 6 h. The mixture was cooled to room temperature and filtered through a celite bed. The filtrate was collected and concentrated under reduced pressure to give 4.3 g of the amino compound as off-white solid; $^1$H NMR (δ ppm, DMSO-$d_6$, 300 MHz): 7.40-7.20 (m, 3H); 6.44 (d, J=8.4, 1H); 6.31 (d, J=7.8, 1H); 3.77 (d, J=6.9, 2H); 3.39 (s, 3H); 1.22-1.05 (m, 1H); 0.48-0.38 (m, 2H); 0.37-0.30 (m, 2H).

Step 5: 2-(3-Cyclopropylmethyl-1-methyl-2,4-dioxo-1,2,3,4-tetrahydroquinazolinyl)-acetic acid was prepared in 3 steps from 5-amino-3-cyclopropylmethyl-1-methyl-1,2,3,4-tetrahydro-2,4-quinazolinedione (Step 4 intermediate) by following the procedure (Steps 4, 5 and 6) described for the preparation of Intermediate 1. The compound was isolated as a white solid; $^1$H NMR (δ ppm, DMSO-$d_6$, 300 MHz): 12.06 (s, 1H); 7.64 (t, J=8.4, 1H); 7.37 (d, J=8.1, 1H); 7.11 (d, J=7.2, 1H); 4.04 (s, 2H); 3.79 (d, J=6.6, 2H); 3.52 (s, 3H); 1.20-1.11 (m, 1H); 0.44-0.30 (m, 4H).

Intermediate 5

2-(3-Ethyloxy carbonyl-2,4-dioxo-1,2,3,4-tetrahydro-5-quinazolinyl)acetic acid

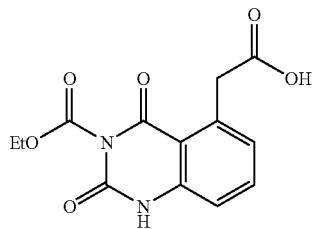

Step 1: Methyl 2-allyl-6-nitrobenzoate: To a stirred solution of allyl bromide (39.7 ml, 459.18 mmol) and tert-butylnitrite (5.5 ml, 45.91 mmol) in acetonitrile (30 ml) was added methyl 6-nitroanthranilic acid (6.0 g, 30.61 mmol) portionwise at room temperature and the mixture was further stirred for 1 h. The volatile components were evaporated under reduced pressure and the residue was diluted with water. The mixture was extracted with ethyl acetate (2×50 ml) and the combined organic extracts were washed with water and dried over anhydrous sodium sulfate. The residue obtained after evaporation of the solvent was purified by silica gel column chromatography using 5% ethyl acetate in petroleum ether as eluent to give 4.2 g of the product as a yellow oil; $^1$H NMR (δ ppm, CDCl$_3$, 300 MHz): 7.99 (d, J=7.8, 1H); 7.58-7.46 (m, 2H); 5.93-5.80 (m, 1H); 5.15-5.03 (m, 2H); 3.93 (s, 3H); 3.46 (d, J=6.0, 2H).

Step 2: Methyl 2-allyl-6-aminobenzoate: To a stirred suspension of Step 1 intermediate (4.2 g, 19.98 mmol) in a mixture of 50% aqueous acetic acid (100 ml) and ethanol (100 ml) was added iron powder (5.3 g, 99.9 g atom) and the mixture was refluxed for 3 h. The mixture was cooled to room temperature and filtered through a celite bed. The filtrate was concentrated and the residue obtained was diluted with ethyl acetate and washed with water (2×50 ml) and dried over anhydrous sodium sulfate. The solvent was evaporated to give 3.2 g of the product as a brown oil; $^1$H NMR (δ ppm, CDCl$_3$, 300 MHz): 7.15-7.07 (m, 1H); 6.62-6.55 (m, 2H); 5.99-5.82 (m, 1H); 5.05-4.95 (m, 2H); 3.86 (s, 3H); 3.53 (d, J=6.0, 2H).

Step 3: 2-Allyl-6-aminobenzoic acid: To a solution of Step 2 intermediate (3.0 g, 15.7 mmol) in ethanol (10 ml) was added 2.0 M potassium hydroxide (4.0 ml) and the mixture was refluxed for 3 h. The mixture was concentrated under reduced pressure and diluted with water. The basic aqueous solution containing the product was washed with diethyl ether (2×25 ml). The aqueous solution was acidified to pH 4.0 with 1N HCl. The solid separated out was filtered and washed with water and dried to give 550 mg of the product as an off-white solid; $^1$H NMR (δ ppm, CDCl$_3$, 300 MHz): 7.01 (t, J=9.0, 1H); 6.57 (d, J=9.0, 1H); 6.36 (d, J=9.0, 1H); 5.94-5.79 (m, 1H); 5.02-4.90 (m, 2H); 3.46 (d, J=6.0, 2H).

Step 4: 5-Allyl-1,2,3,4-tetrahydro-2,4-quinazolinedione: Prepared by the reaction of Step 3 intermediate (530 mg, 2.98 mmol) with urea (2.3 g, 39.0 mmol) in refluxing glacial acetic acid (15 ml) to give 195 mg of the product as a white solid; $^1$H NMR (δ ppm, DMSO-$d_6$, 300 MHz): 11.08 (br.s, 1H); 11.03 (br.s, 1H); 7.47 (t, J=9.0, 1H); 7.00 (d, J=7.8, 1H); 6.91 (d, J=9.0, 1H), 6.05-5.85 (m, 1H); 5.03-4.90 (m, 2H); 3.88 (d, J=6.0, 2H).

Step 5: Ethyl 5-allyl-2,4-dioxo-1,2,3,4-tetrahydro-3-quinazolinecarboxylate: To a solution of Step 4 intermediate (1.28 g, 6.33 mmol) in dry DMF (6.3 ml) was added triethylamine (4.38 ml, 31.35 mmol) and ethyl chloroformate (3.03 ml, 31.65 mmol). The reaction was stirred at room temperature for 24 h. The reaction was diluted with water, extracted with ethyl acetate, washed with brine and dried over Na$_2$SO$_4$. Purification of the crude product by silica gel column chromatography using 1% ethyl acetate in chloroform afforded 1.3 g of the title compound; $^1$H NMR (δ ppm, CDCl$_3$, 300 MHz): 9.56 (br.s, 1H); 7.49 (t, J=7.8, 1H); 7.05 (d, J=7.2, 1H); 6.93 (d, J=8.4, 1H); 6.11-5.90 (m, 1H), 5.07-4.98 (m, 2H); 4.53 (q, J=7.2, 2H); 3.96 (d, J=6.3, 2H); 1.46 (t, J=7.2, 3H).

Step 6: 2-(3-Ethyloxy carbonyl-2,4-dioxo-1,2,3,4-tetrahydro-5-quinazolinyl)acetic acid: Oxidative cleavage of Step 5 intermediate (1.25 g, 4.55 mmol) using sodium metaperiodate (5.85 g, 27.34 mmol) and ruthenium (III) chloride trihydrate (18.9 mg, 0.091 mmol) as described in Step 6 of intermediate 1 gave 650 mg of the product as an off-white solid; $^1$H NMR (δ ppm, DMSO-$d_6$, 300 MHz): 12.15 (br.s, 1H); 11.81 (br. s, 1H); 7.60 (t, J=7.8, 1H); 7.14 (d, J=7.8, 1H); 7.07 (d, J=6.9, 1H); 4.38 (q, J=6.9, 2H); 3.98 (s, 2H); 1.31 (t, J=6.9, 3H).

General Procedure for the Preparation of 2-amino-4-aryl thiazoles

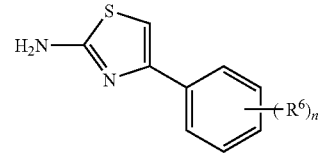

Method A

A solution of acetophenone derivative (1.0 eq) in glacial acetic acid (5 vol) was added in liquid bromine (1.0 eq) at 0° C. and reaction mixture was stirred at room temperature for 2 h. The reaction mixture was diluted with water and extracted with ethyl acetate, washed with brine and dried over Na$_2$SO$_4$. The crude product obtained upon concentration was dissolved in dry THF (10 vol) and thiourea (2.0 eq) was added and refluxed for overnight. The reaction mixture was diluted with ethyl acetate, washed with sodium thiosulfate solution and organic layer was treated with 1N HCl to result salt formation of the amine. The precipitated salt was collected by filtration. The salt was then treated with saturated solution of NaHCO$_3$ to re-generate the amine. The mixture was extracted with dichloromethane (2×50 ml) and the combined organic extracts were washed with water and brine. The solvent was evaporated under reduced pressure to afford the 2-amino-4-aryl-thiazole derivative.

Method B

A solution of acetophenone derivative (1.0 equiv.), thiourea (2.0 equiv.) and iodine (1.0 equiv.) in dry ethanol (5 vol) was refluxed for 24 h. The reaction mixture was diluted with ethyl acetate and the layers were separated. The organic layer was washed with sodium thiosulfate solution to remove iodine. The ethyl acetate solution was treated with 1N HCl and precipitated salt collected by filtration. The free amine was re-generated as described in Method A given above.

All the 2-amino-4-aryl-thiazole derivatives were prepared by either Method A or Method B starting from appropriate aryl alkyl ketones. Structure information and characterization data for selected intermediates are given in Table 1.

TABLE 1

Structure and $^1$H NMR data of selected 2-amino-4-arylthiazoles

| S No | Structure | Mol. Formula (Mol. Wt.) | $^1$H NMR (δ ppm, 300 MHz) |
|---|---|---|---|
| 1. | 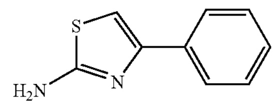 | $C_9H_8N_2S$ (176.24) | DMSO-$d_6$: 7.76 (d, J = 7.8, 2H); 7.33 (t, J = 7.8, 2H); 7.23 (d, J = 6.9, 1H); 7.04 (br. s, 2H); 6.98 (s, 1H). |
| 2. | 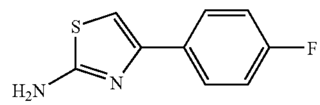 | $C_9H_7FN_2S$ (194.23) | CDCl$_3$: 7.76-7.70 (m, 2H); 7.03 (t, J = 8.1, 2H); 6.62 (s, 1H); 5.06 (br s, 2H). |
| 3 | 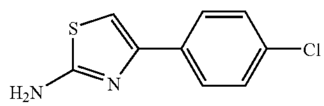 | $C_9H_7ClN_2S$ (210.68) | DMSO-$d_3$: 7.78 (d, J = 8.4, 2H); 7.39 (d, J = 7.8, 2H); 7.07 (br. s, 2H); 7.05 (s, 1H). |
| 4. | 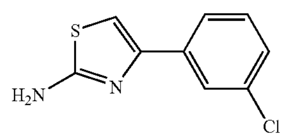 | $C_9H_7ClN_2S$ (210.68) | CDCl$_3$: 7.75 (s, 1H); 7.61 (d, J = 7.2, 1H); 7.30-7.20 (m, 2H), 6.72 (s, 1H); 5.04 (br s, 2H). |
| 5. | 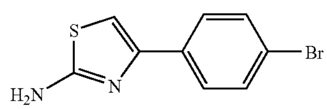 | $C_9H_7BrN_2S$ (255.14) | DMSO-$d_6$: 7.61 (d, J = 8.1, 2H); 7.46 (d, J = 7.8, 2H); 6.70 (s, 1H); 4.99 (br. s, 2H). |
| 6. | 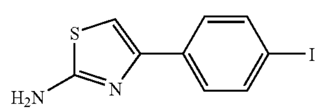 | $C_9H_7IN_2S$ (302.14) | CDCl$_3$: 7.67 (d, J = 8.7, 2H); 7.50 (d, J = 8.4, 2H); 6.72 (s, 1H); 4.97 (br s, 2H). |
| 7. | 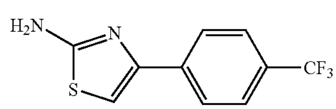 | $C_{10}H_7F_3N_2S$ (244.24) | DMSO-$d_6$: 7.97 (d. J = 7.8, 2H); 7.69 (d, J = 8.1, 2H); 7.24 (s, 1H); 7.16 (br. s, 2H). |
| 8. | 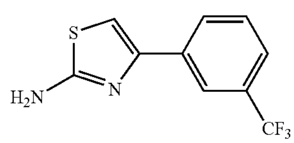 | $C_{10}H_7F_3N_2S$ (244.24) | CDCl$_3$: 8.12-8.06 (m, 1H); 7.91 (d, J = 6.9, 1H); 7.50-7.42 (m, 2H); 6.79 (s, 1H); 5.02 (br. s, 2H). |
| 9. | 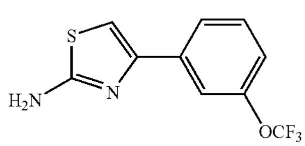 | $C_{10}H_6F_4N_2S$ (262.24) | CDCl$_3$: 7.68-7.61 (m, 2H); 7.36 (t, J = 7.8, 1H); 7.10 (d, J = 7.8, 1H), 6.75 (s, 1H); 5.08 (br s, 2H). |
| 10. | 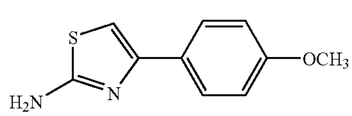 | $C_{10}H_{10}N_2OS$ (206.27) | CDCl$_3$: 7.69 (d, J = 8.7, 2H); 6.98 (br. s, 2H), 6.89 (d, J = 8.7, 2H); 6.80 (s, 1H); 3.75 (s, 3H). |
| 11. | 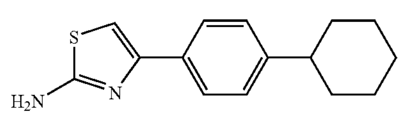 | $C_{15}H_{18}N_2S$ (258.38) | CDCl$_3$: 7.65 (d, J = 7.8, 2H); 7.18 (d, J = 7.8, 2H); 6.63 (s, 1H); 5.12 (br. s, 2H); 2.52-2.45 (m, 1H); 1.90-1.80 (m, 6H); 1.45-1.38 (m, 4H). |

TABLE 1-continued

Structure and $^1$H NMR data of selected 2-amino-4-arylthiazoles

| S No | Structure | Mol. Formula (Mol. Wt.) | $^1$H NMR (δ ppm, 300 MHz) |
|---|---|---|---|
| 12. | 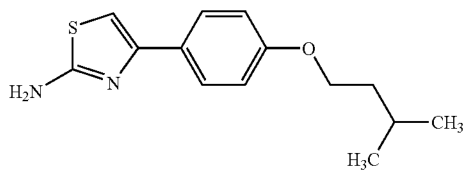 | $C_{14}H_{18}N_2OS$ (262.37) | CDCl$_3$: 7.35-7.27 (m, 3H); 6.93-6.85 (m, 2H); 4.09-4.01 (m, 2H); 2.76 (br s, 2H); 1.88-1.80 (m, 1H); 1.73-1.64 (m, 2H), 0.96 (d, J = 6.6, 6H). |
| 13. | 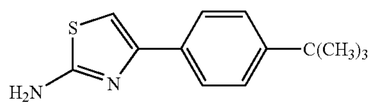 | $C_{13}H_{16}N_2S$ (232.35) | DMSO-d$_6$: 7.67 (d, J = 8.1, 2H); 7.34 (d, J = 9.0, 2H); 7.01 (br. s, 2H); 6.89 (s. 1H); 1.28 (s, 9H). |
| 14. | 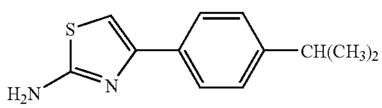 | $C_{12}H_{14}N_2S$ (218.32) | CDCl$_3$: 7.66 (d, J = 7.8, 2H); 7.26-7.20 (m, 2H); 6.64 (s, 1H); 5.08 (br. s, 2H); 2.94-2.87 (m, 1H), 1.25 (d, J = 6.9, 6H). |
| 15. | 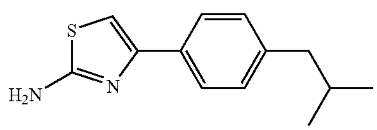 | $C_{13}H_{16}N_2S$ (232.25) | DMSO-d$_6$: 7.68 (d, J = 7.8, 2H); 7.13 (d, J = 8.1, 2H); 7.03 (br. s, 2H); 6.92 (s, 1H); 2.43 (d, J = 6.9, 2H); 1.86-1.76 (m, 1H); 0.86 (d, J = 6.6, 6H) |
| 16. | 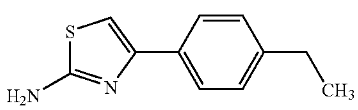 | $C_{11}H_{12}N_2S$ (220.07) | CDCl$_3$: 7.66 (d, J = 7.8, 2H); 7.20 (d, J = 7.5, 2H); 6.65 (s, 1H); 5.06 (br. s, 2H); 2.65 (d, J = 7.5, 2H); 1.24 (t, J = 7.2, 3H). |
| 17. | 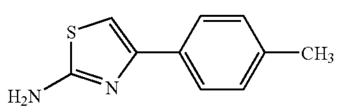 | $C_{10}H_{10}N_2S$ (190.27) | CDCl$_3$: 7.63 (d, J = 7.8, 2H); 7.15 (d, J = 8.4, 2H); 6.65 (s, 1H); 4.99 (br. s, 2H); 2.35 (s, 3H). |
| 18. | 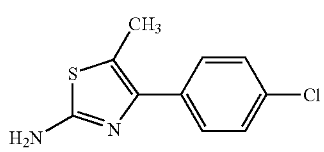 | $C_{10}H_9ClN_2S$ (224.71) | CDCl$_3$: 7.47 (d, J = 8.7, 2H); 7.33 (d, J = 8.4, 2H); 4.92 (br. s, 2H); 2.37 (s, 3H). |
| 19. | 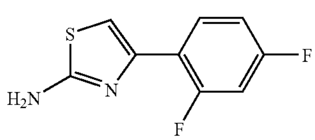 | $C_9H_6F_2N_2S$ (212.22) | CDCl$_3$: 8.04-7.95 (m, 1H); 6.93-6.80 (m, 3H); 5.04 (br. s, 2H). |
| 20. | 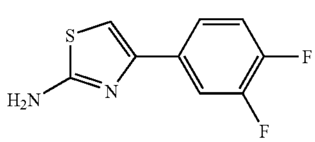 | $C_9H_6F_2N_2S$ (212.22) | CDCl$_3$: 7.60-7.53 (m, 1H); 7.48-7.43 (m, 1H); 7.18-7.07 (m, 1H); 6.66 (s, 1H); 4.98 (br. s, 2H). |
| 21. | 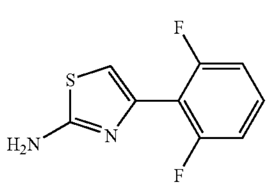 | $C_9H_6F_2N_2S$ (212.22) | CDCl$_3$: 7.29-7.17 (m, 1H); 6.92 (t, J = 7.8, 2H); 6.74 (s. 1H); 5.30 (br s, 2H). |

TABLE 1-continued

Structure and $^1$H NMR data of selected 2-amino-4-arylthiazoles

| S No | Structure | Mol. Formula (Mol. Wt.) | $^1$H NMR (δ ppm, 300 MHz) |
|---|---|---|---|
| 22. | (3,5-difluorophenyl) | $C_9H_6F_2N_2S$ (212.22) | CDCl$_3$: 7.30-7.20 (m, 2H); 6.80-6.74 (m, 1H); 6.68-6.60 (m, 1H), 5.06 (br s, 2H). |
| 23. | (2,3-difluorophenyl) | $C_9H_6F_2N_2S$ (212.22) | CDCl$_3$: 7.78-7.70 (m, 1H); 7.12-7.00 (m, 3H); 5.06 (br s, 2H). |
| 24. | (2-fluoro-4-trifluoromethylphenyl) | $C_{10}H_6F_4N_2S$ (262.23) | CDCl$_3$: 8.15 (t, J = 7.2, 1H); 7.42 (d, J = 7.8, 1H); 7.37-7.30 (m, 1H); 7.13 (s, 1H); 5.00 (br. s, 2H). |
| 25. | (3-fluoro-4-trifluoromethylphenyl) | $C_{10}H_6F_4N_2S$ (262.23) | DMSO-d$_6$: 7.85-7.70 (m, 3H); 7.37 (s, 1H); 7:22 (br. s, 2H). |
| 26. | (4-fluoro-3-trifluoromethylphenyl) | $C_{10}H_6F_4N_2S$ (262.23) | DMSO-d$_6$: 8.14 (d, J = 6.6, 2H); 7.52 (t, J = 8.7, 1H); 7.24 (s, 1H); 7.20 (br. s, 2H). |
| 27. | (4-fluoro-2-trifluoromethylphenyl) | $C_{10}H_6F_4N_2S$ (262.23) | CDCl$_3$: 7.61-7.55 (m, 1H); 7.45-7.38 (m, 1H); 7.28-7.18 (m, 1H); 6.54 (s, 1H); 5.02 (br s, 2H). |
| 28. | (2-fluoro-5-trifluoromethylphenyl) | $C_{10}H_6F_4N_2S$ (262.23) | CDCl$_3$: 8.36-8.29 (m, 1H); 7.73-7.65 (m, 1H); 7.58-7.50 (m, 1H); 7.26 (br.s, 2H); 7.13 (s, 1H). |
| 29. | (3-fluoro-4-trifluoromethoxyphenyl) | $C_{10}H_6F_4N_2OS$ (278.23) | DMSO-d$_6$: 7.87-7.80 (m, 1H); 7.73 (d, J = 8.7, 1H); 7.55 (d, = 8.1, 1H); 7.24 (s, 1H); 7.18 (br. s, 2H). |
| 30. | (4-fluoro-3-trifluoromethoxyphenyl) | $C_{10}H_6F_4N_2OS$ (278.23) | DMSO-d$_6$: 7.92-7.85 (m, 2H): 7.50 (t, J = 8.7, 1H); 7.18 (br. s, 3H). |
| 31. | (3-fluoro-4-methoxyphenyl) | $C_{10}H_9FN_2OS$ (224.26) | DMSO-d$_6$: 7.62-7.56 (m, 2H); 7.15 (t, J = 8.4, 1H); 7.07 (br. s, 2H); 6.95 (s, 1H); 3.85 (s, 3H). |

TABLE 1-continued

Structure and ¹H NMR data of selected 2-amino-4-arylthiazoles

| S No | Structure | Mol. Formula (Mol. Wt.) | ¹H NMR (δ ppm, 300 MHz) |
|---|---|---|---|
| 32. | (2-amino-4-[3-fluoro-4-(difluoromethoxy)phenyl]thiazole) | $C_{10}H_7F_3N_2OS$ (260.24) | DMSO-$d_6$: 7.75-7.62 (m, 2H); 7.33 (t, J = 8.1, 1H); 7.23 (t, J = 73.2, 1H); 7.12 (br. s, 3H). |
| 33. | (2-amino-4-(2,4-dichlorophenyl)thiazole) | $C_9H_6Cl_2N_2S$ (245.13) | CDCl$_3$: 7.72 (d, J = 8.1, 1H); 7.42 (s, 1H); 7.26 (s, 1H); 7.06 (s, 1H); 5.02 (br. s, 2H). |
| 34. | (2-amino-4-(2,5-dichlorophenyl)thiazole) | $C_9H_6Cl_2N_2S$ (245.13) | DMSO-$d_6$: 7.91 (s, 1H); 7.51 (d, J = 8.4, 1H); 7.35 (d, J = 7.8, 1H); 7.28 (s, 1H); 7.14 (br. s, 2H). |
| 35. | (2-amino-4-(3,4-dichlorophenyl)thiazole) | $C_9H_6Cl_2N_2S$ (245.13) | CDCl$_3$: 7.85 (s, 1H); 7.56 (dd, J = 8.4, 2.1, 1H); 7.39 (d, J = 8.4, 1H); 6.72 (s, 1H); 5.01 (br. s, 2H). |
| 36. | (2-amino-4-(3,5-dichlorophenyl)thiazole) | $C_9H_6Cl_2N_2S$ (245.13) | DMSO-$d_6$: 7.80 (s, 2H.); 7.46-740 (m, 1H); 7.31 (s, 1H); 7.17 (br. s, 2H). |
| 37. | (2-amino-4-(3-chloro-4-fluorophenyl)thiazole) | $C_9H_6ClFN_2S$ (228.67) | DMSO-$d_6$: 7.94 (d, J = 7.2, 1H); 7.80-7.74 (m, 1H); 7.39 (t, J = 9.0, 1H); 7.15-7.10 (m, 3H). |
| 38. | (2-amino-4-(3-chloro-2-fluorophenyl)thiazole) | $C_9H_6ClFN_2S$ (228.67) | DMSO-$d_6$: 7.89 (t, J = 7.8, IH); 7.46 (t, J = 7.8, 1H); 7.23 (t, J = 7.8, 1H); 7.15 (br. s, 2H); 7.03 (s, 1H). |
| 39. | (2-amino-4-(4-chloro-2-fluorophenyl)thiazole) | $C_9H_6ClFN_2S$ (228.67) | DMSO-$d_6$: 7.95 (t, J = 8.4, 1H); 7.49-7.42 (m, 1H); 7.35-7.28 (m, 1H); 7.13 (br. s, 2H); 6.95 (s, 1H). |
| 40. | (2-amino-4-(5-chloro-2-fluorophenyl)thiazole) | $C_9H_6ClFN_2S$ (228.67) | DMSO-$d_6$: 7.96-7.90 (m, 1H); 7.36-7.28 (m, 2H); 7.18 (br. s, 2H); 7.02 (s, 1H); |

TABLE 1-continued

Structure and ¹H NMR data of selected 2-amino-4-arylthiazoles

| S No | Structure | Mol. Formula (Mol. Wt.) | ¹H NMR (δ ppm, 300 MHz) |
|---|---|---|---|
| 41. | 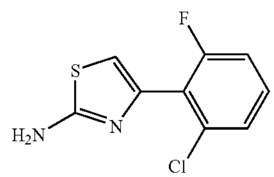 | $C_9H_6ClFN_2S$ (228.67) | CDCl$_3$: 7.30-7.17 (m, 2H); 7.06-6.98 (m, 1H); 6.61 (s, 1H); 5.15 (br s, 2H). |
| 42. | 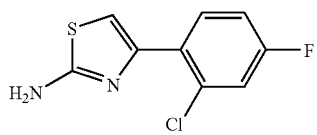 | $C_9H_6ClFN_2S$ (228.67) | DMSO-d$_6$: 7.87-7.80 (m, 1H); 7.47-7.42 (m, 1H); 7.27-7.18 (m, 1H); 7.06 (br. s, 2H); 6.98 (s, 1H). |
| 43. | 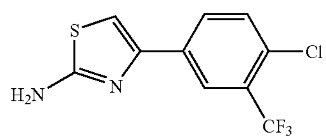 | $C_{10}H_6ClF_3N_2S$ (278.68) | CDCl$_3$: 8.08 (s, 1H); 7.82 (d, J = 7.8, 1H); 7.46 (d, J = 8.1, 1H); 6.78 (s, 1H); 5.05 (br. s, 2H). |
| 44. | 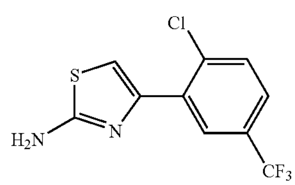 | $C_{10}H_6ClF_3N_2S$ (278.68) | CDCl$_3$: 8.22 (s, 1H); 7.72 (d, J = 8.1, 1H); 7.62 (d, J = 8.1, 1H); 7.29 (s, 1H); 7.21 (br. s, 2H). |
| 45. | 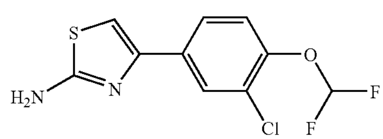 | $C_{10}H_7ClF_2N_2OS$ (275.99) | DMSO-d$_6$: 7.98 (s, 1H); 7.80 (d, J = 8.4, 1H); 7.29 (t, J = 73.5, 1H); 7.36 (d, J = 8.4, 1H); 7.17 (br. s, 3H). |
| 46. | 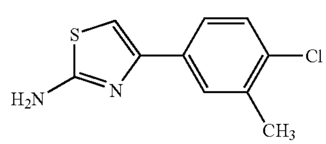 | $C_{10}H_9ClN_2S$ (224.71) | CDCl$_3$: 7.63 (s, 1H); 7.48 (d, J = 8.1, 1H); 7.30 (d, J = 8.1, 1H); 6.66 (s, 1H); 5.32 (br. s, 2H); 2.39 (s, 3H). |
| 47. | 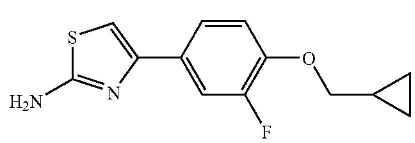 | $C_{13}H_{13}FN_2OS$ (264.32) | DMSO-d$_6$: 7.61-7.51 (m, 2H); 7.04-7.15 (m, 3H); 6.94 (s, 1H); 3.92-3.85 (m, 2H); 1.26-1.20 (m, 1H); 0.62-0.52 (m, 2H); 0.36-0.30 (m, 2H). |
| 48. | 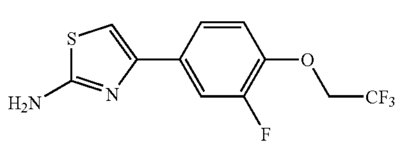 | $C_{11}H_8F_4N_2OS$ (292.25) | CDCl$_3$: 7.57-7.46 (m, 2H); 7.02 (t, J = 8.4, 1H); 6.66 (s, 1H); 5.08 (br. s, 2H); 4.43 (q, J = 8.4, 2H). |
| 49. | 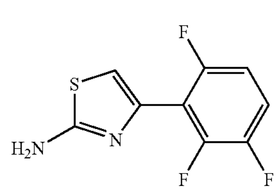 | $C_9H_5F_3N_2S$ (230.21) | CDCl$_3$: 7.11-7.00 (m, 1H); 6.91-6.84 (m, 1H); 6.80 (s, 1H); 5.06 (br s, 2H). |

TABLE 1-continued

Structure and ¹H NMR data of selected 2-amino-4-arylthiazoles

| S No | Structure | Mol. Formula (Mol. Wt.) | ¹H NMR (δ ppm, 300 MHz) |
|---|---|---|---|
| 50. | 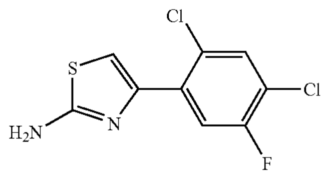 | $C_9H_5Cl_2FN_2S$ (263.12) | CDCl$_3$: 7.74 (d, J = 9.0, 1H); 7.44 (d, J = 6.9, 1H); 7.19 (s, 1H); 4.97 br s, 2H). |
| 51 | 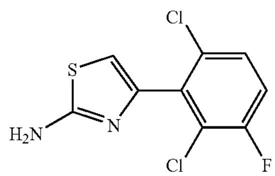 | $C_9H_5Cl_2FN_2S$ (263.12) | DMSO-d$_6$: 7.58-7.44 (m, 2H); 7.06 (br. s, 2H); 6.62 (s, 1H). |
| 52. | 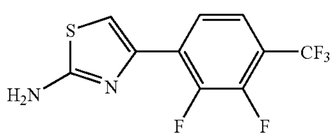 | $C_{10}H_5F_5N_2S$ (280.22) | CDCl$_3$: 7.94-7.82 (m, 1H); 7.42-7.32 (m, 1H); 7.18-7.10 (m, 1H); 5.09 (br s, 2H). |
| 53. | 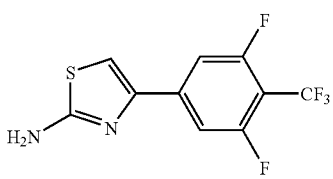 | $C_{10}H_5F_5N_2S$ (280.22) | DMSO-d$_6$: 7.72 (d, J = 11.7, 2H); 7.52 (s. 1H); 7.29 (br. s, 2H). |
| 54. | 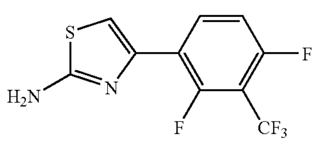 | $C_{10}H_5F_5N_2S$ (280.22) | DMSO-d$_6$: 8.35-8.23 (m, 1H); 7.48-7.35 (m, 1H); 7.21 (br. s, 2H); 7.05 (s, 1H). |
| 55. | 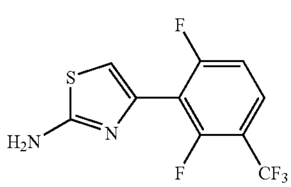 | $C_{10}H_5F_5N_2S$ (280.22) | CDCl$_3$: 7.89-7.80 (m, 1H); 7.39 (t, J = 8.7, 1H); 7.17 (br. s, 2H); 6.93 (s, 1H). |
| 56. | 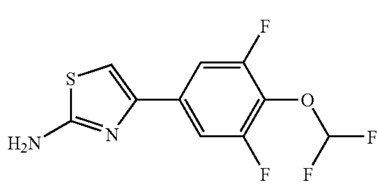 | $C_{10}H_6F_4N_2OS$ (278.23) | DMSO-d$_6$: 7.65 (d, J = 9.0, 2H); 7.48 (s, 1H); 7.24 (t, J = 72.3, 1H); 7.20 (br. s, 2H). |
| 57. | 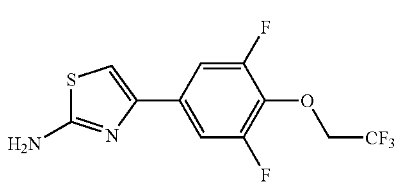 | $C_{11}H_7F_5N_2OS$ (310.24) | DMSO-d$_6$: 7.59 (s, 1H); 7.55 (s, 1H); 7.21 (s, 1H); 7.16 (br. s, 2H); 4.82 (q, J = 9.0, 2H). |

TABLE 1-continued

Structure and ¹H NMR data of selected 2-amino-4-arylthiazoles

| S No | Structure | Mol. Formula (Mol. Wt.) | ¹H NMR (δ ppm, 300 MHz) |
|---|---|---|---|
| 58. | (2-amino-thiazole linked to 3,5-difluoro-4-methoxyphenyl) | $C_{10}H_8F_2N_2OS$ (242.25) | CDCl₃: 7.53 (s, 1H); 7.50 (s, 1H); 7.18-7.12 (m, 3H); 3.92 (s, 3H). |
| 59. | (2-amino-thiazole linked to 3,5-difluoro-4-(cyclopropylmethoxy)phenyl) | $C_{13}H_{12}F_2N_2OS$ (282.31) | CDCl₃: 7.33 (s, 1H); 7.29 (s, 1H); 6.66 (s, 1H); 5.01 (br. s, 2H); 3.97 (d, J = 6.9, 2H); 1.28-1.22 (m, 1H) 0.61-0.56 (m, 2H); 0.31-0.25 (m, 2H). |

Preferably inventors of the presentation have found that quinazolinyl acetamide derivatives prepared from substituted 2-amino-4-aryl thiazoles showed improved potency towards TRPA1. Further it should also be noted that several fluoro substituted 2-amino-4-aryl thiazoles can be prepared using the approach described in Scheme 7 starting from appropriate fluorinated benzoic acid or fluroninated acetophenone. A few examples of such aminothiazole intermediates are given in Table 2.

TABLE 2

Structure of fluoro substituted 2-amino-4-arylthiazoles

| S No | Structure | Name | Mol. Formula | (Mol. Wt.) |
|---|---|---|---|---|
| 1. | (structure) | 4-[2,6-difluoro-4-(trifluoromethyl)phenyl]-1,3-thiazol-2-amine | $C_{10}H_5F_5N_2S$ | 280.22 |
| 2. | (structure) | 4-[2,5-difluoro-4-(trifluoromethyl)phenyl]-1,3-thiazol-2-amine | $C_{10}H_5F_5N_2S$ | 280.22 |
| 3. | (structure) | 4-[3,4-difluoro-5-(trifluoromethyl)phenyl]-1,3-thiazol-2-amine | $C_{10}H_5F_5N_2S$ | 280.22 |
| 4. | (structure) | 4-[2,3-difluoro-5-(trifluoromethyl)phenyl]-1,3-thiazol-2-amine | $C_{10}H_5F_5N_2S$ | 280.22 |

TABLE 2-continued

Structure of fluoro substituted 2-amino-4-arylthiazoles

| S No | Structure | Name | Mol. Formula | (Mol. Wt.) |
|---|---|---|---|---|
| 5. | 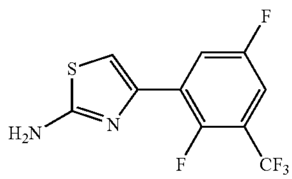 | 4-[2,5-difluoro-3-(trifluoromethyl)phenyl]-1,3-thiazol-2-amine | $C_{10}H_5F_5N_2S$ | 280.22 |
| 6. | 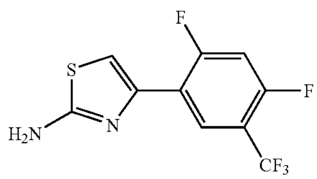 | 4-[2,4-difluoro-5-(trifluoromethyl)phenyl]-1,3-thiazol-2-amine | $C_{10}H_5F_5N_2S$ | 280.22 |
| 7. | 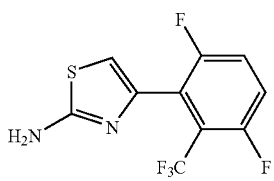 | 4-[3,6-difluoro-2-(trifluoromethyl)phenyl]-1,3-thiazol-2-amine | $C_{10}H_5F_5N_2S$ | 280.22 |
| 8. | 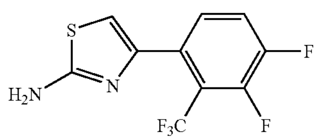 | 4-[3,4-difluoro-2-(trifluoromethyl)phenyl]-1,3-thiazol-2-amine | $C_{10}H_5F_5N_2S$ | 280.22 |
| 9. | 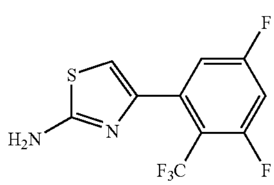 | 4-[3.5-difluoro-2-(trifluoromethyl)phenyl]-1,3-thiazol-2-amine | $C_{10}H_5F_5N_2S$ | 280.22 |
| 10. | 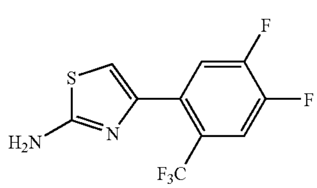 | 4-[4,5-difluoro-2-(trifluoromethyl)phenyl]-1,3-thiazol-2-amine | $C_{10}H_5F_5N_2S$ | 280.22 |
| 11. | 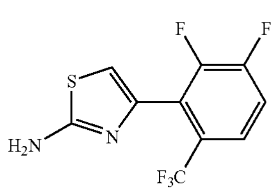 | 4-[2,3-difluoro-6-(trifluoromethyl)phenyl]-1,3-thiazol-2-amine | $C_{10}H_5F_5N_2S$ | 280.22 |
| 12. | 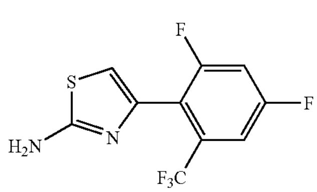 | 4-[2,4-difluoro-6-(trifluoromethyl)phenyl]-1,3-thiazol-2-amine | $C_{10}H_5F_5N_2S$ | 280.22 |

The 7-chloro-4,5-dihydronaphtho[1,2-d]thiazole-2-ylamine was prepared from 6-chloro-1-tetralone (similar procedure described by Norman L. Allinger and Edward S. Jones, (1962), 27, 70-76) and 2-amino-4-indolylthiazoles were prepared from commercially available 3-acetylindoles by its reaction with thiourea in presence of iodine (Method B). Structure and spectral data is given in Table 3.

TABLE 3

Structure and $^1$H NMR data of naphthothiazole amine and indolyl thiazole amines

| S No | Structure | Mol. Formula (Mol. Wt.) | $^1$H NMR (δ ppm, 300 MHz) |
|---|---|---|---|
| 1. | [structure] | $C_{11}H_9ClN_2S$ (236.72) | CDCl$_3$: 7.56 (d, J = 7.8, 1H); 7.17 (d, J = 8.4, 1H); 7.12 (s, 1H); 4.94 (br. s, 2H); 3.01-2.96 (m, 2H): 2.86-2.80 (m, 2H). |
| 2 | [structure] | $C_{11}H_9N_3S$ (215.28) | DMSO-d$_6$: 11.13 (br. s, 1H): 7.95 (d, J = 8.4, 1H); 7.58 (s, 1H); 7.36 (d, J = 7.8, 1H); 7.12-7.00 (m, 2H); 6.90 (br. s, 2H); 6.66 (s, 1H). |
| 3. | [structure] | $C_{12}H_{11}N_3S$ (229.30) | DMSO-d$_6$: 8.87 (br. s, 2H); 7.81 (s, 2H); 7.54 (d, J = 7.8, 1H); 7.30 (t, J = 7.8, 1H); 7.22 (t, J = 7.2, 1H); 6.97 (s, 1H); 3.86 (s, 3H). |

3-(4-Chlorophenyl)-1H-pyrazol-5-amine was purchased from Aldrich chemical company. 5-Amino-2-phenylpyrazoles were prepared as described in scheme 8 and structural information and characterization data of intermediates prepared are given in Table 4.

TABLE 4

Structure and $^1$H NMR data of selected 5-amino-2-phenylpyrazoles

| S No | Structure | Mol. Formula (Mol. Wt.) | $^1$H NMR (δ ppm, 300 MHz) |
|---|---|---|---|
| 1. | [structure] | $C_9H_7ClFN_3$ (211.62) | CDCl$_3$: 7.80-7.72 (m, 2H); 7.21-7.14 (m, 2H); 5.85 (s, 1H); 3.84 (br. s, 2H). |
| 2. | [structure] | $C_9H_8ClN_3$ (193.63) | CDCl$_3$: 7.63 (s, 1H); 7.47 (d, J = 8.4, 2H); 7.32 (d, J = 8.7, 2H); 5.83 (s, 1H); 3.82 (br. s, 2H). |
| 3. | [structure] | $C_{10}H_8F_3N_3$ (227.19) | CDCl$_3$: 7.82 (s, 1H): 7.73-7.68 (m, 2H), 7.48 (t, J = 7.8, 1H); 7.38 (d, J = 7.5, 1H); 5.87 (s, 1H); 3.27 (br. s, 2H). |

For further illustration of methods of preparing the compounds of the present invention, the following examples are disclosed below.

EXAMPLES

General Procedure for the Synthesis of Examples 1-83

Method A

To a stirred solution of quinazolinedione acetic acid derivative (1.0 equiv.) in 1,2-dichloroethane (100 ml) was added EDCI (1.2 equiv.), HOBt (0.3 equiv.) and 4-dimethylaminopyridine (0.1 equiv.) and the mixture was stirred at room temperature for 10-15 min. An appropriate amine (1.0 equiv.) was then added and mixture was stirred at the same temperature for 48 h. The solvent was evaporated under reduced pressure and the residue obtained was diluted with methanol (200 ml) and stirred at room temperature for 30 min. The solid separated out was collected by filtration. The solid product was further purified by recrystallization from isopropanol or methanol to give the desired products.

Method B

To a stirred solution of quinozolinedione acetic acid derivative (1.0 equiv.) in a mixture of tetrahydrofuran and N,N-dimethylformamide (3:1) was added EDCI (2.0 equiv.) and the mixture was stirred for 30 min. An appropriate amine (1.0 equiv.) and 4-dimethylaminopyridine (DMAP) (0.2 equiv.) was added and mixture was maintained at 80° C. under stirring for another 24 h. Most Of the tetrahydrofuran is evaporated under reduced pressure and the mixture was acidified to pH 6.0 by addition of 2N hydrochloric acid. The solid precipitated out was collected by filtration. The product was further purified by crystallization or by silica gel column chromatography using methanol-chloroform mixture.

Example 1

N1-[4-(4-Bromophenyl)phenyl]-2-(1,3-dimethyl-2,4-dioxo-1,2,3,4-tetrahydro-5-quinazolinyl)acetamide

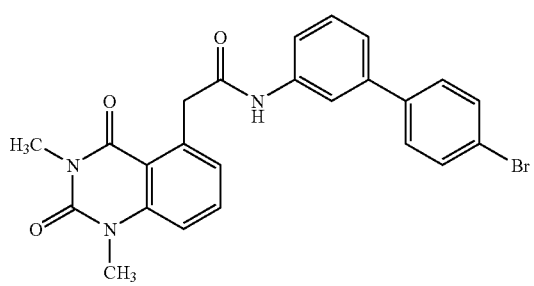

The title compound was prepared according to the general procedure (Method A) by coupling Intermediate 1 (100 mg, 0.403 mmol) with 4'-bromobiphenyl-3-amine (100 mg, 0.403 mmol) in the presence of EDCI hydrochloride (92 mg, 0.483 mmol), HOBt (16 mg, 0.120 mmol) and DMAP (5 mg, 0.040 mmol) in 1,2-dichloroethane (5 ml) to give 55 mg of the product as an off-white solid. $^1$H NMR (δ ppm, DMSO-d$_6$, 300 MHz): 10.19 (s, 1H); 9.41 (s, 1H); 7.75-7.60 (m, 3H); 7.60-7.45 (m, 3H), 7.43-7.25 (m, 3H); 7.17 (d, J=6.9, 1H); 4.27 (s, 2H); 3.54 (s, 3H); 3.24 (s, 3H). IR (cm$^{-1}$, KBr): 3290, 3259, 1703, 1666, 1654, 1611, 1598, 1552, 1499, 1481, 1421, 1383, 1344, 1310, 1228, 1185, 1073, 1026, 1009, 961, 811. MS (m/z): 479.84 ([M+H]$^+$).

Example 2

N1-[4-(4-Bromophenyl)phenyl]-2-(1,3-dimethyl-2,4-dioxo-1,2,3,4-tetrahydro-5-quinazolinyl)acetamide

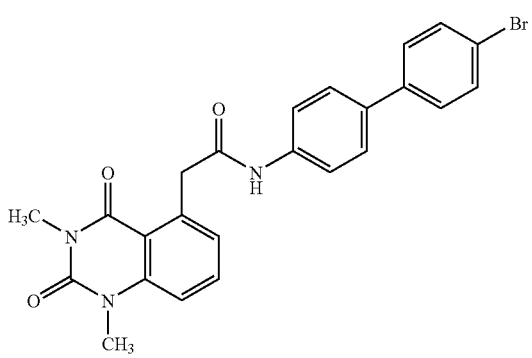

The title compound was prepared according to the general procedure (Method A) by coupling Intermediate 1 (100 mg, 0.403 mmol) with 4'-bromophenyl-4-amine (100 mg, 0.403 mmol) in the presence of EDCI hydrochloride (92 mg, 0.483 mmol), HOBt (16 mg, 0.120 mmol) and DMAP (5 mg, 0.403 mmol) in 1,2-dichloroethane (5 ml) to give 105 mg of the product as an off-white solid. $^1$H NMR (δ ppm, DMSO-d$_6$, 300 MHz): 10.19 (s, 1H); 7.76-7.57 (m, 9H); 7.39 (d, J=8.7, 1H); 7.17 (d, J=7.2, 1H); 4.26 (s, 2H); 3.53 (s, 3H); 3.24 (s, 3H). IR (cm$^{-1}$, KBr): 3288, 3033, 2948, 1704, 1651, 1599, 1525, 1504, 1479, 1414, 1343, 1311, 1285, 1197, 1182, 1071, 1024, 1003, 963, 811. MS (m/z): 479.83 ([M+H]$^+$).

Example 3

N1-[4-(4-Methylphenoxy)phenyl]-2-(1,3-dimethyl-2,4-dioxo-1,2,3,4-tetrahydro-5-quinazolinyl)acetamide

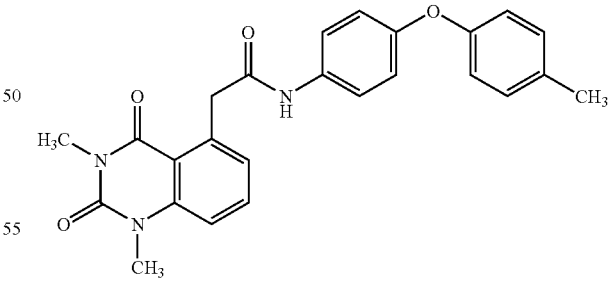

The title compound was prepared according to the general procedure (Method A) by coupling Intermediate 1 (200 mg, 0.806 mmol) with 4-(4-methylphenoxy)aniline (161 mg, 0.806 mmol) in the presence of EDCI hydrochloride (188 mg, 0.967 mmol), HOBt (33 mg, 0.241 mmol) and DMAP (10 mg, 0.080 mmol) in 1,2-dichloroethane (10 ml) to give 92 mg of the product as an off-white solid. $^1$H NMR (δ ppm, DMSO-d$_6$, 300 MHz): 10.04 (br. s, 1H); 7.66 (t, J=7.8, 1H); 7.55 (d, J=8.7, 2H); 7.38 (d, J=8.4, 1H); 7.20-7.05 (m, 3H); 6.90 (d, J=8.7, 2H); 6.83 (d, J=8.4, 2H); 4.23 (s, 2H); 3.53 (s, 3H); 3.42 (s, 3H); 2.56 (s, 3H). IR (cm$^{-1}$, KBr): 3250, 2952, 1698, 1686, 1659, 1639, 1599, 1500, 1480, 1414, 1343, 1234, 1185, 1166, 1069, 1024, 955, 822, 749. MS (m/z): 430.14 ([M+H]$^+$).

Example 4

N1-[6-(4-chlorophenyl)-2-pyridyl]-2-(1,3-dimethyl-2,4-dioxo-1,2,3,4-tetrahydro-5-quinazolinyl)acetamide

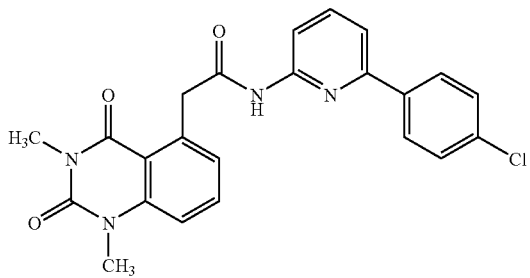

The title compound was prepared according to the general procedure (Method A) by coupling Intermediate 1 (100 mg, 0.403 mmol) with 6-(4-chlorophenyl)pyridin-2-amine (82 mg, 0.403 mmol) in the presence of EDCI hydrochloride (93 mg, 0.483 mmol), HOBt (16 mg, 0.120 mmol) and DMAP (5 mg, 0.040 mmol) in 1,2-dichloroethane (5 ml) to give 15 mg of the product as an off white solid. $^1$H NMR (δ ppm, DMSO-d$_6$, 300 MHz): 10.63 (s, 1H); 8.11 (d, J=8.4, 2H); 7.94 (d, J=8.4, 1H); 7.80 (t, J=7.8, 1H); 7.70-7.60 (m, 2H); 7.56 (d, J=8.4, 2H); 7.39 (d, J=7.8, 1H); 7.16 (d, J=7.2, 1H); 4.33 (s, 2H); 3.54 (s, 3H); 3.23 (s, 3H). IR (cm$^{-1}$, KBr): 3400, 2925, 1699, 1682, 1658, 1598, 1519, 1500, 1450, 1377, 1286, 1110, 1093, 1014, 803. MS (m/z): 435.33 ([M+H]$^+$).

Example 5

N1-[5-(4-chlorophenyl)-2-pyridyl]-2-(1,3-dimethyl-2,4-dioxo-1,2,3,4-tetrahydro-5-quinazolinyl)acetamide

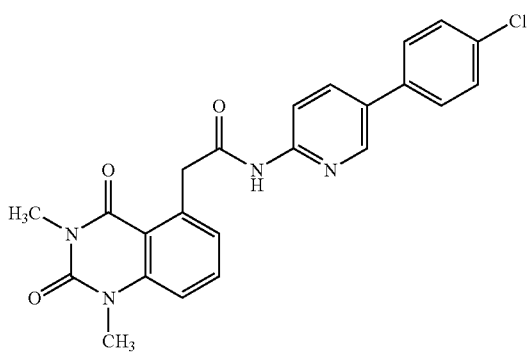

The title compound was prepared according to the general procedure (Method A) by coupling Intermediate 1 (200 mg, 0.806 mmol) with 5-(4-chlorophenyl)pyridin-2-amine (165 mg, 0.806 mmol) in the presence of EDCI hydrochloride (188 mg, 0.967 mmol), HOBt (33 mg, 0.241 mmol) and DMAP (10 mg, 0.080 mmol) in 1,2-dichloroethane (10 ml) to give 152 mg of the product as an off white solid. $^{1H\ NMR}$ (δ ppm, DMSO-d$_6$, 300 MHz): 10.70 (br. s, 1H); 8.64 (s, 1H); 8.04 (s, 2H); 7.80-7.60 (m, 3H); 7.50 (d, J=8.1, 2H); 7.40 (d, J=9.0, 1H); 7.16 (d, J=7.2, 1H); 4.31 (s, 2H); 3.54 (s, 3H); 3.23 (s, 3H). IR (cm$^{-1}$, KBr): 3299, 2950, 1702, 1674, 1651, 1599, 1518, 1498, 1481, 1410, 1344, 1310, 1295, 1181, 1094, 1015, 961, 820. MS (m/z): 435.30 ([M+H]$^+$).

Example 6

N1-[6-(4-Trifluoromethylphenyl)-2-pyridyl]-2-(1,3-dimethyl-2,4-dioxo-1,2,3,4-tetrahydro-5-quinazolinyl)acetamide

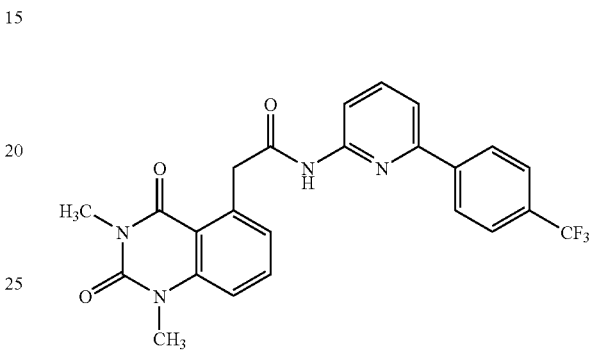

The title compound was prepared according to the general procedure as described in method A by coupling Intermediate 1 (100 mg, 0.403 mmol) with 6-(4-trifluoromethylphenyl)pyridin-2-amine (96 mg, 0.403 mmol) in the presence of EDCI hydrochloride (93 mg, 0.483 mmol), HOBt (16 mg, 0.120 mmol) and DMAP (5 mg, 0.040 mmol) in 1,2-dichloroethane (5 ml) to give 61 mg of the product as an off white solid. $^{1H\ NMR}$ (δ ppm, DMSO-d$_6$, 300 MHz): 10.71 (s, 1H); 8.30 (d, J6.9, 2H); 8.00-7.95 (m, 1H); 7.86 (d, J=6.9, 3H); 7.75-7.66 (m, 2H); 7.40 (d, J=8.7, 1H); 7.17 (d, J=8.7, 1H); 4.33 (s, 2H); 3.53 (s, 3H); 3.23 (s, 3H). IR (cm$^{-1}$, KBr): 3440, 3300, 1693, 1639, 1599, 1570, 1536, 1504, 1420, 1380, 1324, 1295, 1167, 1110, 1083, 1062, 1017, 992, 851, 804. MS (m/z): 469.14 ([M+H]$^+$).

Example 7

N1-[4-(4-Cyclohexyl)-1,3-thiazol-2yl]-2-(1,3-dimethyl-2,4-dioxo-1,2,3,4-tetrahydro-5-quinazolinyl)acetamide

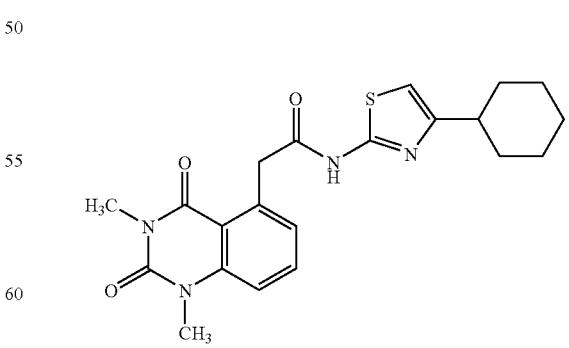

The title compound was prepared according to the general procedure as described in method A by coupling Intermediate 1 (200 mg, 0.806 mmol) with 4-cyclohexyl-1,3-thiazol-2-amine (145 mg, 0.806 mmol) in the presence of EDCI hydrochloride (184 mg, 0.967 mmol) and HOBt (32 mg, 0.241 mmol) in 1,2-dichloroethane (10 ml) to give 220 mg of the product as an off white solid. ¹H NMR (δ ppm, DMSO-d₆, 300 MHz): 12.13 (br. s, 1H); 7.67 (t, J=8.1, 1H); 7.40 (d, J=8.1, 1H); 7.15 (d, J=7.2, 1H); 6.63 (s, 1H); 4.26 (s, 2H); 3.52 (s, 3H); 3.21 (s, 3H); 2.60-2.50 (m, 1H); 2.00-1.85 (m, 2H); 1.80-1.64 (m, 3H); 1.47-1.20 (m, 5H). IR (cm⁻¹, KBr): 3217, 2919, 1694, 1631, 1600, 1557, 1505, 1480, 1417, 1341, 1315, 1283, 1173, 1027, 945, 740. MS (m/z) 413.18 ([M+H]⁺).

Example 8

N1-[4-phenyl-1,3-thiazol-2-yl]-2-(1,3-dimethyl-2,4-dioxo-1,2,3,4-tetrahydro-5-quinazolinyl)acetamide

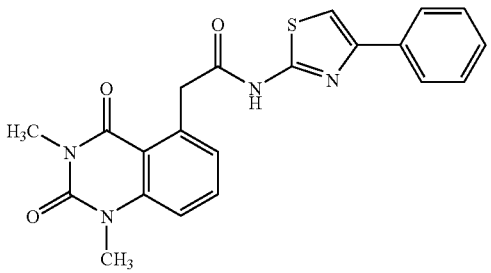

The title compound was prepared according to the general procedure as described in method A by coupling Intermediate 1 (100 mg, 0.403 mmol) with 4-phenyl-1,3-thiazol-2-amine (71 mg, 0.403 mmol) in the presence of EDCI hydrochloride (92 mg, 0.483 mmol), HOBt (16 mg, 0.120 mmol) and DMAP (5 mg, 0.403 mmol) in 1,2-dichloroethane (5 ml) to give 82 mg of the product as an off white solid. ¹H. NMR (δ ppm, DMSO-d₆, 300 MHz): 12.37 (s, 1H); 7.89 (d, J=7.8, 2H); 7.69 (t, J=7.8, 1H); 7.54 (s, 1H); 7.45-7.35 (m, 3H); 7.31 (d, J=6.9, 1H); 7.18 (d, J=6.9, 1H); 4.33 (s, 2H); 3.53 (s, 3H); 3.21 (s, 3H). IR (cm⁻¹, KBr): 3258, 3224, 1693, 1634, 1601, 1547, 1504, 1482, 1444, 1427, 1378, 1340, 1282, 1201, 1166, 1145, 1073, 1073, 1027, 968, 840, 760. MS (m/z): 407.09 ([M+H]⁺).

Example 9

N1-[4-(4-Fluorophenyl)-1,3-thiazol-2yl]-2-(1,3-dimethyl-2,4-dioxo-1,2,3,4-tetrahydro-5-quinazolinyl)acetamide

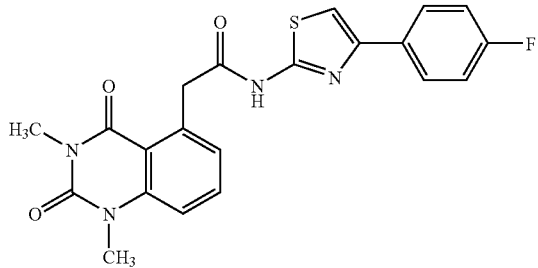

The title compound was prepared according to the general procedure as described in method A by coupling Intermediate 1 (200 mg, 0.806 mmol) with 4-(4-fluorophenyl)-1,3-thiazol-2-amine (156 mg, 0.8060 mmol) in the presence of EDCI hydrochloride (185 mg, 0.967 mmol), HOBt (32 mg, 0.241 mmol) and DMAP (10 mg, 0.080 mmol) in 1,2-dichloroethane (10 ml) to give 18 mg of the product as off-white solid. ¹H NMR (δ ppm, DMSO-d₆, 300 MHz): 12.36 (br. s, 1H); 7.95-7.82 (m, 2H); 7.72-7.65 (m, 1H); 7.52 (s, 1H); 7.41 (d, J=8.7, 1H); 7.28-7.15 (m, 3H); 4.32 (s, 2H); 3.53 (s, 3H); 3.21 (s, 3H).

Example 10

N1-[4-(4-Chlorophenyl-1,3-thiazol-2yl]-2-(1,3-dimethyl-2,4-dioxo-1,2,3,4-tetrahydro-5-quinazolinyl)acetamide

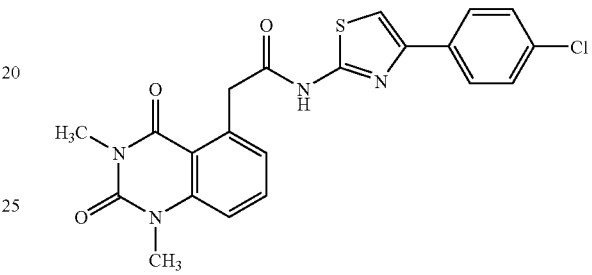

The title compound was prepared according to the general procedure as described in method A by coupling Intermediate 1 (200 ng, 0.806 mmol) with 4-(4-chlorophenyl)-1,3-thiazol-2-amine (169 mg, 0.806 mmol) in the presence of EDCI hydrochloride (184 mg, 0.967 mmol), HOBt (32 mg, 0.241 mmol) and DMAP (10 mg, 0.080 mmol) in 1,2-dichloroethane (10 ml) to give 90 mg of the product as a white solid. ¹H NMR (δ ppm, DMSO-d₆, 300 MHz): 12.37 (br. s, 1H); 7.90 (d, J=7.8, 2H); 7.71-7.64 (m, 1H); 7.60 (s, 1H); 7.49-7.39 (m, 3H); 7.17 (d, J=8.1, 1H); 4.32 (s, 2H); 3.53 (s, 3H); 3.21 (s, 3H). IR (cm⁻¹, KBr): 3273, 1691, 1642, 1600, 1542, 1504, 1481, 1448, 1430, 1409, 1314, 1279, 1162, 1062, 1025, 1012, 834, 748. MS (m/z): 441.16 ([M+H]⁺).

Example 11

N1-[4-(3-Chlorophenyl)-1,3-thiazol-2yl]-2-(1,3-dimethyl-2,4-dioxo-1,2,3,4-tetrahydro-5-quinazolinyl)acetamide

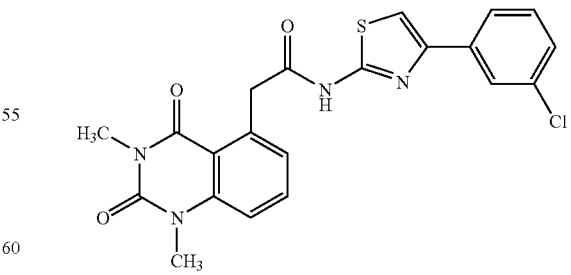

The title compound was prepared according to the general procedure (Method A) by coupling Intermediate 1 (200 mg, 0.806 mmol) with 4-(3-chlorophenyl)-1,3-thiazol-2-amine (169 mg, 0.806 mmol) in the presence of EDCI hydrochloride (184 mg, 0.967 mmol), HOBt (32 mg, 0.241 mmol) and DMAP (10 mg, 0.080 mmol) in 1,2-dichloroethane (10 ml) to give 181 mg of the product as a white solid. $^1$H NMR (δ ppm, DMSO-d$_6$, 300 MHz): 12.40 (br. s, 1H); 7.95 (s, 1H); 7.86 (d, J=7.2, 1H); 7.71-7.65 (m, 2H); 7.49-7.37 (m, 3H); 7.18 (d, J=7.2, 1H); 4.33 (s, 2H); 3.53 (s, 3H); 3.21 (s, 3H). IR (cm$^{-1}$, KBr): 3250, 2964, 1694, 1651, 1601, 1549, 1505, 1482, 1379, 1251, 1197, 1026, 981, 812. MS (m/z): 441.11 ([M+H]$^+$).

Example 12

N1-[4-(4-Bromophenyl-1,3-thiazol-2yl]-2-(1,3-dimethyl-2,4-dioxo-1,2,3,4-tetrahydro-5-quinazolinyl)acetamide

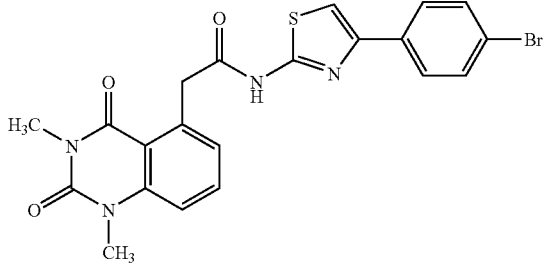

The title compound was prepared according to the general procedure (Method A) by coupling Intermediate 1 (200 mg, 0.806 mmol) with 4-(4-bromophenyl)-1,3-thiazol-2-amine (243 mg, 0.806 mmol) in the presence of EDCI hydrochloride (184 mg, 0.967 mmol), HOBt (32 mg, 0.241 mmol) and DMAP (10 mg, 0.080 mmol) in 1,2-dichloroethane (10 ml) to give 101 mg of the product as a white solid. $^1$H NMR (δ ppm, DMSO-d$_6$, 300 MHz): 12.37 (s, 1H); 7.83 (d, J=8.4, 2H); 7.72-7.58 (m, 4H); 7.41 (d, J=9.0, 1H); 7.18 (d, J=7.8, 1H); 4.32 (s, 2H); 3.53 (s, 3H); 3.21 (s, 3H). IR (cm$^{-1}$, KBr): 3268, 1683, 1691, 1642, 1601, 1541, 1501, 1481, 1430, 1409, 1334, 1409, 1334, 1278, 1163, 1071, 1025, 1009, 832, 748. MS (m/z): 483.24 ([M−2H]$^+$).

Example 13

N1-[4-(4-Iodophenyl)-1,3-thiazol-2yl]-2-(1,3-dimethyl-2,4-dioxo-1,2,3,4-tetrahydro-5-quinazolinyl)acetamide

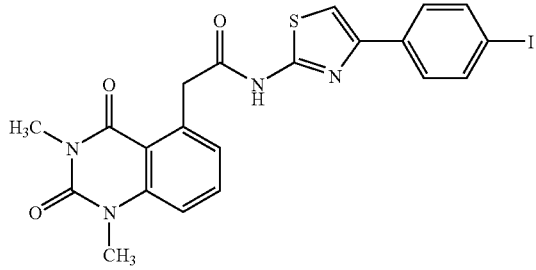

The title compound was prepared according to the general procedure (Method A) by coupling Intermediate 1 (200 mg, 0.806 mmol) with 4-(4-iodophenyl)-1,3-thiazol-2-amine (243 mg, 0.806 mmol) in the presence of EDCI hydrochloride (184 mg, 0.967 mmol), HOBt (32 mg, 0.241 mmol) and DMAP (10 mg, 0.080 mmol) in 1,2-dichloroethane (10 ml) to give 231 mg of the product as an off white solid. $^1$H NMR (δ ppm, DMSO-d$_6$, 300 MHz): 12.39 (br. s, 1H); 7.80-7.75 (m, 2H); 7.74-7.60 (m, 3H); 7.60 (s, 1H); 7.41 (d, J=8.4, 1H); 7.17 (d, J=7.2, 1H); 4.32 (s, 2H); 3.53 (s, 3H); 3.21 (s, 3H). IR (cm$^{-1}$, KBr): 3335, 3098, 1694, 1651, 1600, 1551, 1501, 1484, 1416, 1375, 1344, 1294, 1203, 1174, 1071, 1025, 759. MS (m/z): 532.91 ([M+H]$^+$).

Example 14

N1-[4-(4-Trifluromethylphenyl)-1,3-thiazol-2yl]-2-(1,3-dimethyl-2,4-dioxo-1,2,3,4-tetrahydro-5-quinazolinyl)acetamide

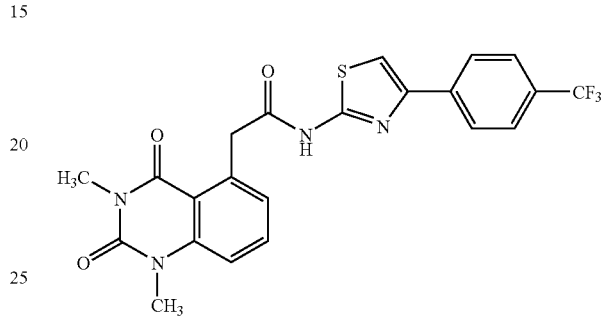

The title compound was prepared according to the general procedure (Method A) by coupling Intermediate 1 (200 mg, 0.806 mmol) with 4-[4-(trifluromethyl)phenyl]-1,3-thiazol-2-amine (197 mg, 0.806 mmol) in the presence of EDCI hydrochloride (188 mg, 0.967 mmol), HOBt (33 mg, 0.241 mmol) and DMAP (10 mg, 0.080 mmol) in 1,2-dichloroethane (10 ml) to give 60 mg of the product as an off white solid. $^1$H NMR (δ ppm, DMSO-d$_6$, 300 MHz): 12.44 (br. s, 1H); 8.10 (d, J=7.8, 2H); 7.80-7.70 (m, 3H); 7.69 (t, J=7.8, 1H); 7.42 (d, J=8.4, 1H); 7.19 (d, J=7.2, 1H); 4.33 (s, 2H); 3.54 (s, 3H); 3.21 (s, 3H). IR (cm$^{-1}$, KBr): 3217, 2922, 1698, 1683, 1629, 1599, 1571, 1557, 1480, 1461, 1398, 1338, 1286, 1263, 1176, 1162, 1025, 1006, 836, 725. MS (m/z): 473.45 ([M+H]$^+$).

Example 15

N1-[4-(3-Trifluoromethylphenyl)-1,3-thiazol-2yl]-2-(1,3-dimethyl-2,4-dioxo-1,2,3,4-tetrahydro-5-quinazolinyl)acetamide

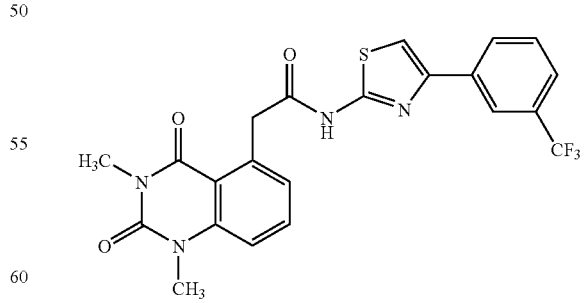

The title compound was prepared according to the general procedure (Method A) by coupling Intermediate 1 (200 mg, 0.806 mmol) with 4-(3-trifluoromethylphenyl)-1,3-thiazole-2-amine (197 mg, 0.806 mmol) in the presence of EDCI hydrochloride (188 mg, 0.967 mmol), HOBt (33 mg, 0.241 mmol) and DMAP (10 mg, 0.080 mmol) in 1,2-dichloroethane to give 45 mg of the title compound as an off white solid. $^1$H NMR (δ ppm, DMSO-d$_6$, 300 MHz): 12.45 (br. s, 1H); 8.24 (s, 1H); 8.20 (br. s, 1H); 7.80 (s, 1H); 7.75-7.60 (m, 3H); 7.42 (d, J=8.1, 1H); 7.19 (d, J=7.2, 1H); 4.33 (s, 2H), 3.54 (s, 3H); 3.22 (s, 3H). IR (cm$^{-1}$, KBr): 3244, 3211, 1695, 1645, 1601, 1548, 1504, 1482, 1418, 1381, 1342, 1317, 1279, 1261, 1164, 1118, 748. MS (m/z): 475.03 ([M+H]$^+$).

Example 16

N1-[4-(3-Trifluoromethoxyphenyl)-1,3-thiazol-2-yl]-2-(1,3-dimethyl-2,4-dioxo-1,2,3,4-tetrahydro-5-quinazolinyl)acetamide

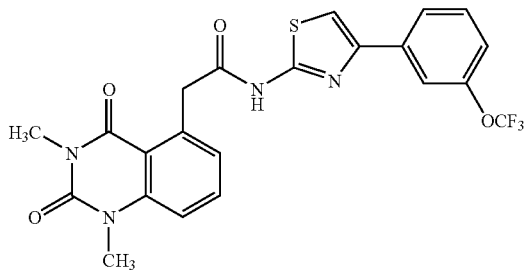

The title compound was prepared according to the general procedure (Method A) by coupling Intermediate 1 (150 mg, 0.604 mmol) with 4-(3-trifluoromethoxyphenyl)-1,3-thiazole-2-amine (157 mg, 0.604 mmol) in the presence of EDCI hydrochloride (139 mg, 0.725 mmol). HOBt (8 mg, 0.604 mmol) and DMAP (7.3 mg, 0.060 mmol) in 1,2-dichloroethane (8 ml) to give 63 mg of the product as an off white solid. $^1$H NMR (δ ppm, DMSO-d$_6$, 300 MHz): 12.41 (s, 1H); 7.92 (d, J=6.9, 1H); 7.85 (s, 1H); 7.75-7.65 (m, 2H); 7.55 (t, J=8.1, 1H); 7.41 (d, J=8.4, 1H), 7.30 (d, J=7.5, 1H); 7.18 (d, J=7.5, 1H); 4.32 (s, 2H); 3.53 (s, 3H); 3.21 (s, 3H). IR (cm$^{-1}$, KBr): 3425, 3097, 2939, 1697, 1673, 1655, 1600, 1552, 1501, 1483, 1428, 1419, 1345, 1317, 1261, 1213, 1163, 1074, 1025, 991, 878, 817, 786, 748. MS (m/z): 491.03 ([M+H]$^+$).

Example 17

N1-[4-(4-Methoxyphenyl)-1,3-thiazol-2-yl]-2-(1,3-dimethyl-2,4-dioxo-1,2,3,4-tetrahydro-5-quinazolinyl)acetamide

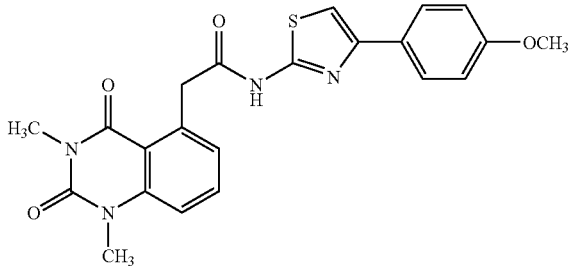

The title compound was prepared according to the general procedure (Method A) by coupling Intermediate 1 (100 mg, 0.403 mmol) with 4-(4-methoxyphenyl)-1,3-thiazol-2-amine (83 mg, 0.403 mmol) in the presence of EDCI hydrochloride (93 mg, 0.488 mmol), HOBt (16 mg, 0.120 mmol) and DMAP (5 mg, 0.080 mmol) in 1,2-dichloroethane to give 30 mg of the title compound as an off white solid. $^1$H NMR (δ ppm, DMSO-d$_6$, 300 MHz): 12.33 (s, 1H); 7.82 (d, J=8.1, 2H); 7.69 (t, J=7.8, 1H); 7.42 (d, J=8.4, 1H); 7.37 (s, 1H); 6.98 (d, J=8.1, 2H); 7.18 (d, J=7.2, 1H); 4.32 (s, 2H); 3.78 (s, 3H); 3.54 (s, 3H); 3.22 (s, 3H). IR (cm$^{-1}$, KBr): 3261, 3233, 2961, 1697, 1642, 1601, 1552, 1504, 1483, 1410, 1346, 1299, 1164, 1025, 928, 752. MS (m/z): 438.28 ([M+2H]$^+$), Example 18

N1-[4-(4-Cyclohexylphenyl)-1,3-thiazol-2yl]-2-(1,3-dimethyl-2,4-dioxo-1,2,3,4-tetrahydro-5-quinazolinyl)acetamide

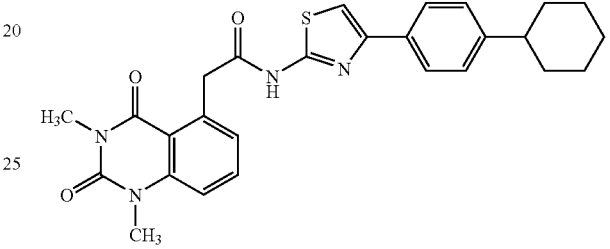

The title compound was prepared according to the general procedure (Method A) by coupling Intermediate 1 (200 mg, 0.806 mmol) with 4-(4-cyclohexylphenyl)-1,3-thiazol-2-amine (208 mg, 0.806 mmol) in the presence of EDCI hydrochloride (184 mg, 0.967 mmol), HOBt (32 mg, 0.241 mmol) and DMAP (10 mg, 0.080 mmol) in 1,2-dichloroethane (10 ml) to give 210 mg of the product as an off white solid. $^1$H NMR (δ ppm, DMSO-d$_6$, 300 MHz): 12.35 (br. s, 1H); 7.79 (d, J=7.8, 2H); 7.72-7.65 (m, 1H); 7.46-7.39 (m, 2H); 7.26 (d, J=7.8, 2H); 7.18 (d, J=7.5, 1H); 4.32 (s, 2H); 3.53 (s, 3H); 3.21 (s, 3H); 2.51-2.48 (m, 1H); 1.83-1.68 (m, 5H); 1.45-1.20 (m, 5H). IR (cm$^{-1}$, KBr): 3253, 2933, 1694, 1645, 1600, 1547, 1504, 1481, 1379, 1337, 1278, 1165, 1065, 962, 854, 749. MS (m/z): 489.00 ([M+H]$^+$).

Example 19

N1-[4-(4-(3-Methylbutoxy)phenyl)-1,3-thiazol-2-yl]-2-(1,3-dimethyl-2,4-dioxo-1,2,3,4-tetrahydro-5-quinazolinyl)acetamide

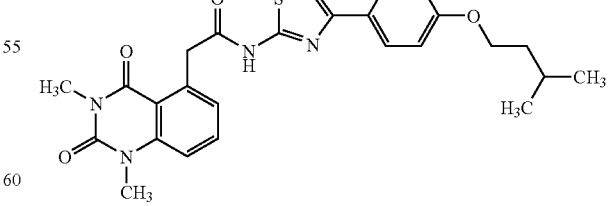

The title compound was prepared according to the general procedure (Method A) by coupling Intermediate 1 (150 mg, 0.604 mmol) with 4-[4-(3-methylbutoxy)phenyl]-1,3-thiazol-2-amine (158 mg, 0.604 mmol) in the presence of EDCI hydrochloride (139 mg, 0.725 mmol), HOBt (81 mg, 0.604 mmol) and DMAP (7 mg, 0.060 mmol) in 1,2-dichloroethane (8 ml) to give 61 mg of the product as an off white solid. $^1$NMR (δ ppm, DMSO-d$_6$, 300 MHz): 12.31 (s, 1H); 7.79 (d, J=8.7, 2H); 7.68 (d, J=7.8, 1H); 7.41 (d, J=9.0, 1H); 7.35 (s, 1H); 7.17 (d, J=6.9, 1H); 6.97 (d, J=9.0, 2H); 4.31 (s, 2H); 4.01 (t, J=6.3, 2H); 3.53 (s, 3H); 3.21 (s, 3H); 1.82-1.73 (m, 1H); 1.66-1.58 (m, 2H); 0.94 (d, J=6.3, 6H). IR (cm$^{-1}$, KBr): 3263, 2955, 1697, 1673, 1651, 1580, 1548, 1501, 1483, 1417, 1342, 1317, 1285, 1249, 1173, 1070, 1024, 904, 833, 747. MS (m/z): 493.17 ([M+H]$^+$).

Example 20

N1-[4-(4-tert-Butylphenyl)-1,3-thiazol-2-yl]-2-(1,3-dimethyl-2,4-dioxo-1,2,3,4-tetrahydro-5-quinazolinyl)acetamide

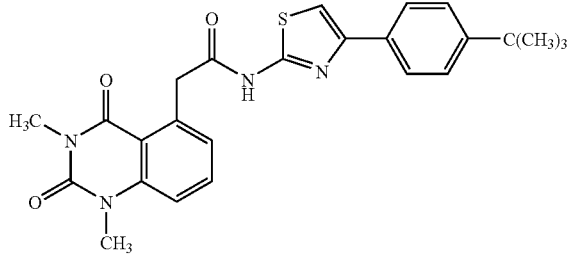

The title compound was prepared according to the general procedure (Method A) by coupling Intermediate 1 (100 mg, 0.403 mmol) with 4-(4-tert-butyl phenyl)-1,3-thiazole-2-amine (94 mg, 0.403 mmol) in the presence of EDCI (93 mg, 0.484 mmol), HOBt (16 mg, 0.120 mmol) and DMAP (5 mg, 0.040 mmol) in 1,2-dichloroethane (5 ml) to give 65 mg of the title compound as an off white solid. $^1$H NMR (δ ppm, DMSO-d$_6$, 300 MHz): 12.37 (s, 1H); 7.81 (d, J=8.1, 2H); 7.69 (t, J=7.8, 1H); 7.50-7.35 (m, 4H); 7.19 (d, J=7.5, 1H); 4.32 (s, 2H); 3.54 (s, 3H); 3.22 (s, 3H); 1.31 (s, 9H). IR (cm$^{-1}$, KBr): 3261, 3233, 2961, 1697, 1642, 1601, 1552, 1504, 1483, 1410, 1346, 1299, 1164, 1025, 928, 752. MS (m/z): 463.28 ([M+H]$^+$).

Example 21

N1-[4-(2-Isobutylphenyl)-1,3-thiazol-2-yl]-2-(1,3-dimethyl-2,4-dioxo-1,2,3,4-tetrahydro-5-quinazolinyl)acetamide

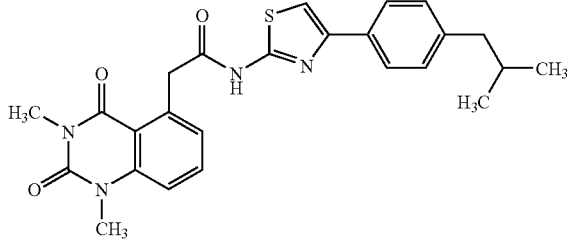

The title compound was prepared according to the general procedure (Method A) by coupling Intermediate 1 (120 mg, 0.483 mmol) with 4-(4-isobutylphenyl)-1,3-thiazol-2-amine (112 mg, 0.483 mmol) in the presence of EDCI hydrochloride (110 mg, 0.581 mmol), HOBt (65 mg, 0.483 mmol) and DMAP (6 mg, 0.048 mmol) in 1,2-dichloroethane (5 ml) to give 101 mg of the product as an off white solid. $^1$H NMR (δ ppm, DMSO-d$_6$, 300 MHz): 12.34 (s, 1H); 7.78 (d, J=7.5, 2H); 7.71-7.64 (m, 1H); 7.46 (s, 1H), 7.41 (d, J=9.0, 1H); 7.21-7.17 (m, 3H); 4.32 (s, 2H); 3.53 (s, 3H); 3.21 (s, 3H); 2.50-2.44 (m, 2H); 1.88-1.80 (m, 1H); 0.88 (d, J=6.3, 6H). MS (m/z): 463.47 ([M+H]$^+$).

Example 22

N1-[4-(4-isopropylphenyl)-1,3-thiazol-2-yl]-2-(1,3-dimethyl-2,4-dioxo-1,2,3,4-tetrahydro-5-quinazolinyl)acetamide

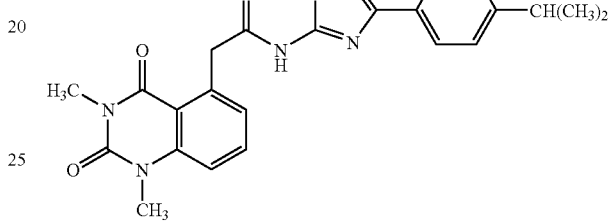

The title compound was prepared according to the general procedure (Method A) by coupling Intermediate 1 (100 mg, 0.403 mmol) with 4-(4-isopropylphenyl)-1,3-thiazole-2-amine (88 mg, 0.403 mmol) in the presence of EDCI (93 mg, 0.483 mmol), HOBt (16 mg, 0.120 mmol) and DMAP (5 mg, 0.040 mmol) in 1,2-dichloroethane (5 ml) to give 35 mg of the title compound as an off white solid. $^1$H NMR (δ ppm, DMSO-d$_6$, 300 MHz): 12.35 (s, 1H); 7.80 (d, J=8.1, 2H); 7.68 (t, J=7.8, 1H); 7.46 (s, 1H); 7.41 (d, J=8.4, 1H); 7.28 (d, J=8.4, 2H); 7.18 (d, J=7.2, 1H), 4.32 (s, 2H); 3.54 (s, 3H); 3.22 (s, 3H); 2.95-2.80 (m, 1H); 1.22 (d, J=6.9, 6H). IR (cm$^{-1}$, KBr): 3255, 3225, 2930, 1695, 1645, 1602, 1548, 1504, 1482, 1433, 1409, 1380, 1280, 1164, 1061, 1025, 961, 836, 747. MS (m/z): 449.04 ([M+H]$^+$).

Example 23

N1-[4-(2-Ethylphenyl)-1,3-thiazol-2-yl]-2-(1,3-dimethyl-2,4-dioxo-1,2,3,4-tetrahydro-5-quinazolinyl)acetamide

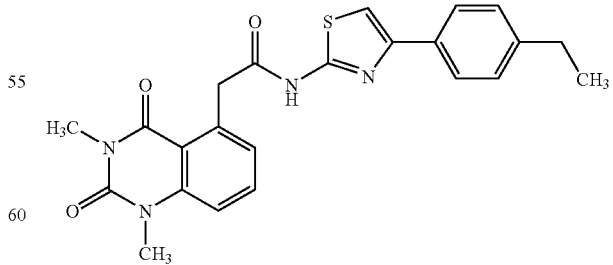

The title compound was prepared according to the general procedure (Method A) by coupling Intermediate 1 (150 mg, 0.604 mmol) with 4-(4-ethylphenyl)-1,3-thiazol-2-amine (123 mg, 0.604 mmol) in the presence of EDCI hydrochloride (115 mg, 0.724 mmol), HOBt (81 mg, 0.604 mmol) and DMAP (7 mg, 0.060 mmol) in 1,2-dichloroethane (5 ml) to give 92 mg of the product as an off white solid. $^1$H NMR (δ ppm, DMSO-d$_6$, 300 MHz): 12.35 (s, 1H); 7.80 (d, J=6.3, 2H); 7.78-7.72 (m, 1H); 7.47-7.30 (m, 2H); 7.27-7.06 (m, 3H); 4.32 (s, 2H); 3.53 (s, 3H); 3.21 (s, 3H); 2.67-2.60 (m, 2H); 1.24-1.19 (m, 3H). IR (cm$^{-1}$, KBr): 3255, 2961, 1694, 1645, 1601, 1547, 1505, 1481, 1432, 1378, 1337, 1279, 1165, 1064, 1024, 962, 880, 811, 749. MS (m/z): 435.35 ([M+H]$^+$).

Example 24

N1-[4-(4-Methylphenyl)-1,3-thiazol-2yl]-2-(1,3-dimethyl-2,4-dioxo-1,2,3,4-tetrahydro-5-quinazolinyl)acetamide

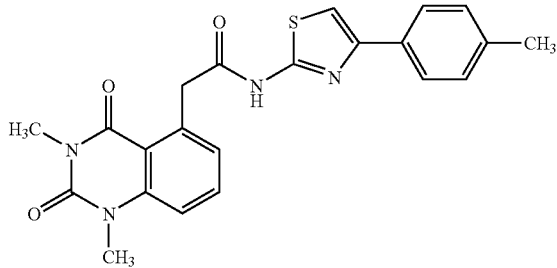

The title compound was prepared according to the general procedure (Method A) by coupling Intermediate 1 (200 mg, 0.806 mmol) with 4-(4-methylphenyl)-1,3-thiazol-2-amine (153 mg, 0.806 mmol) in the presence of EDCI hydrochloride (185 mg, 0.967 mmol), HOBt (32 mg, 0.241 mmol) and DMAP (9 mg, 0.080 mmol) in 1,2-dichloroethane (8 ml) to give 134 mg of the product as a cream colored solid. $^1$H NMR (δ ppm, DMSO-d6, 300 MHz): 12.34 (br. s, 1H);, 7.77 (d, J=7.8, 2H); 7.72-7.64 (m, 1H); 7.47-7.39 (m, 2H); 7.24-7.16 (m, 3H); 4.32 (s, 2H); 3.53 (s, 3H): 3.21 (s, 3H); 2.32 (s, 3H).

Example 25

N1-[4-(4-Chlorophenyl)-1,3-thiazol-2-yl]-2-(1,3-diethyl-2,4-dioxo-1,2,3,4-tetrahydro-5-quinazolinyl)acetamide

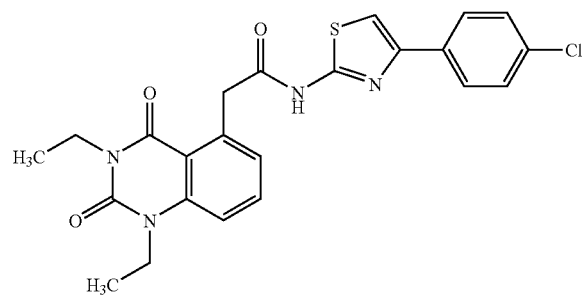

The title compound was prepared according to the general procedure (Method A) by coupling Intermediate 2 (200 mg, 0.724 mmol) with 4-(4-chlorophenyl)-1,3-thiazol-2-amine (153 mg, 0.724 mmol) in the presence of EDCI (166 mg, 0.868 mmol), HOBt (98 mg, 0.724 mmol) and DMAP (9 mg, 0.072 mmol) in 1,2-dichloroethane (10 ml) to give 27 mg of the title compound as an off white solid. $^1$H NMR (δ ppm, DMSO-d$_6$, 300 MHz): 12.36 (s, 1H); 7.90 (d, J=8.1, 2H); 7.75-7.58 (m, 1H); 7.60 (s, 1H); 7.47 (d, J=6.3, 3H); 7.16 (d, J=6.3, 1H); 4.31 (s, 2H); 4.22-4.10 (m, 2H); 3.95-3.80 (m, 2H); (d, J=1.20 (m, 3H); 1.15-1.00 (m, 3H). IR (cm$^{-1}$, KBr): 3399, 2980, 1693, 1651, 1597, 1536, 1489, 1476, 1403, 1353, 1291, 1261, 1175, 1155, 1089, 1048, 977, 755. MS (m/z): 467.33 ([M−H]$^+$).

Example 26

N1-[4-(3-Trifluoromethylphenyl)-1,3-thiazo-2-yl]-2-(1,3-dipropyl-2,4-dioxo-1,2,3,4-tetrahydro-5-quinazolinyl)acetamide

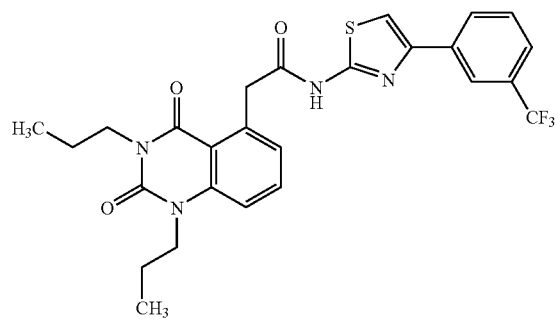

The title compound was prepared according to the general procedure (Method A) by coupling Intermediate 3 (400 mg, 1.314 mmol) with 4-(3-trifluoromethylphenyl)-1,3-thiazole-2-amine (320 mg, 1.314 mmol) in the presence of EDCI (302 mg, 1.577 mmol), HOBt (177 mg, 1.314 mmol) and DMAP (16 mg, 0.131 mmol) in 1,2-dichloroethane (13 ml) to give 75 mg of the title compound as an off white solid. $^1$H NMR (δ ppm, DMSO-d$_6$, 300 Hz): 12.42 (s, 1H); 9.25-8.15 (m, 2H); 7.79 (s, 1H); 7.70-7.64 (m, 3H); 7.45 (d, J=8.4, 1H); 7.16 (d, J=7.5, 1H); 4.31 (s, 2H); 4.10-4.00 (m, 2H); 3.80-3.73 (m, 2H); 1.68-1.62 (m, 2H); 1.52-1.50 (m, 2H); 0.95 (t, J=7.2, 3H); 0.80 (t, J=7.2, 3H). IR (cm$^{-1}$, KBr): 3262, 2966, 1698, 1656, 1599, 1542, 1493, 1477, 1405, 1342, 1300, 1263, 1221, 1199, 1163, 1124, 1094, 1070, 916, 893, 754. MS (m/z): 531.11 ([M+H]$^+$).

Example 27

N1-[4-(4-tert-Butylphenyl)-1,3-thiazol-2-yl]-2-(1-methyl-3-cyclopropylmethyl-2,4-dioxo-1,2,3,4-tetrahydro-5-quinazolinyl)acetamide

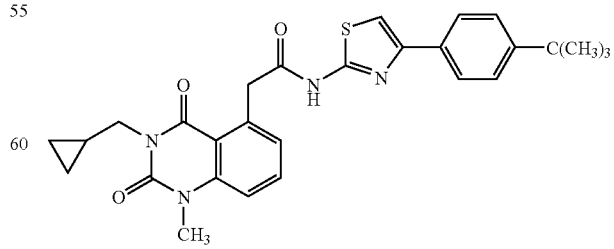

The title compound was prepared according to the general procedure (Method A) by coupling Intermediate 4 (150 mg, 0.604 mmol) with 4-(4-tert-butylphenyl)-1,3-thiazol-2-amine (123 mg, 0.604 mmol) in the presence of EDCI hydrochloride (115 mg, 0.724 mmol), HOBt (81 mg, 0.604 mmol) and DMAP (7 mg, 0.060 mmol) in 1,2-dichloroethane (5 ml) to give 92 mg of the product as an off white solid. $^1$H NMR (δ ppm, DMSO-$d_6$, 300 Hz): 12.33 (s, 1H); 7.80 (d, J=8.1, 2H); 7.69 (t, J=7.8, 1H); 7.48-7.40 (m, 4H): 7.18 (d, J=7.8, 1H), 4.31 (s, 2H); 3.75 (d, J=6.6, 2H); 3.54 (s, 3H); 1.30 (s, 9H); 1.14-1.07 (m, 1H), 1.05-1.01 (m, 2H); 0.25-0.31 (m, 2H). IR (cm$^{-1}$, KBr): 3259, 2961, 1699, 1656, 1598, 1544, 1498, 1481, 1404, 1381, 1351, 1325, 1269, 1201, 1161, 1120, 1063, 1020, 966, 841, 751. MS (m/z): 503.14 ([M+H]$^+$).

Example 28

Ethyl 5-[2-(4-chlorophenyl)-1,3-thiazol-5-ylcarboxymethyl]-2,4-dioxo-1,2,3,4-tetrahydro-3-quinazolinecarboxylate

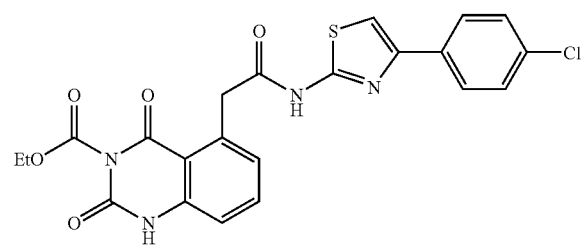

The title compound was prepared according to the general procedure (Method A) by coupling Intermediate 5 (1 g, 3.424 mmol) with 4-(4-chlorophenyl)-1,3-thiazole-2-amine (721 mg, 3.424 mmol) in the presence of EDCI hydrochloride (787 mg, 4.108 mmol), HOBt (462 mg, 3.424 mmol) and DMAP (41 mg, 0.342 mmol) in 1,2-dichloroethane (35 ml) to give 779 mg of the product as an off white solid. $^1$H NMR (δ ppm, DMSO-$_6$, 300 Hz): 12.37 (s, 1H); 11.82 (s, 1H); 7.89 (d, J=8.1, 2H); 7.68-7.60 (m, 2H); 7.47 (d, J=8.4, 2H); 7.21-7.10 (m, 2H); 4.40-4.30 (m, 2H); 4.26 (s, 2H); 1.25 (t, J=7.2, 3H). IR (cm$^{-1}$, KBr): 3262, 2972, 1793, 1724, 1662, 1597, 1547, 1477, 1453, 1404, 1367, 1317, 1281, 1242, 1173, 1133, 1090, 1013, 973, 820, 739. MS (m/z): 485.05 ([M+H]$^+$).

Example 29

N1-[4-(4-Chlorophenyl)-1,3-thiazol-2-yl]-2-(2,4-dioxo-1,2,3,4-tetrahydro-5-quinazolinyl)acetamide

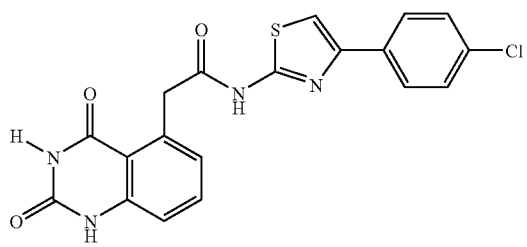

To a stirred solution of Example 28 (300 mg, 0.618 mmol) in ethanol (2 ml) was added 1.25 M aqeous KOH (0.6 ml) and mixture was refluxed for 24 h. The mixture was concentrated under reduced pressure and acidified with 1N HCl. The solid separated out was filtered. The crude solid was refluxed in isopropyl alcohol (25 ml) for 1 h and filtered while hot to give 28 mg of the product as an off-white solid; $^1$H NMR (δ ppm, DMSO-$d_6$, 300 Hz): 12.36 (s, 1H); 11.15 (s, 2H); 7.92 (d, J=8.4, 2H); 7.79 (d, J=8.1, 2H); 7.63 (s, 1H); 7.59-7.47 (m, 2H); 7.17-7.12 (m, 1H); 7.05 (d, J=7.5, 1H); 4.26 (s, 2H). MS (m/z): 413.05 ([M+H]$^+$).

Example 30

N1-[4-(4-Chlorophenyl)-5-methyl-1,3-thiazolyl]-2-(1,3-dimethyl-2,4-dioxo-1,2,3,4-tetrahydro-5-quinazolinyl)acetamide

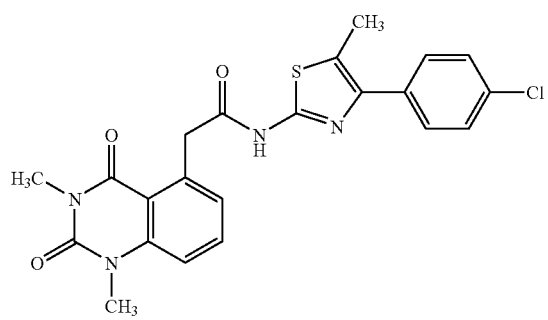

The title compound was prepared according to the general procedure (Method A) by coupling Intermediate 1 (200 mg, 0.806 mmol) with 4-(4-chlorophenyl)-5-methyl-1,3-thiazole-2-amine (181 mg, 0.806 mmol) in the presence of EDCI (185 mg, 0.967 mmol), HOBt (33 mg, 0.241 mmol) and DMAP (10 mg, 0.080 mmol) in 1,2-dichloroethane (10 ml) to give 140 mg of the title compound as an off white solid. $^1$H NMR (δ ppm, DMSO-$d_6$, 300 MHz): 12.20 (br. s, 1H); 7.75-7.60 (m, 3H); 7.50 (d, J=8.7, 2H); 7.42 (d, J=8.1, 1H); 7.18 (d, J=7.2, 1H); 4.29 (s, 2H); 3.54 (s, 3H); 3.22 (s, 3H); 2.43 (s, 3H). IR (cm$^{-1}$, KBr): 3216, 2994, 1687, 1637, 1600, 1580, 1503, 1482, 1414, 1326, 1308, 1289, 1162, 1111, 1069, 1018, 979, 860. MS (m/z): 455.34 ([M+H]$^+$).

Example 31

N1-[4-(2,4-Difluorophenyl)-1,3-thiazol-2-yl]-2-(1,3-dimethyl-2,4-dioxo-1,2,3,4-tetrahydro-5-quinazolinyl)acetamide

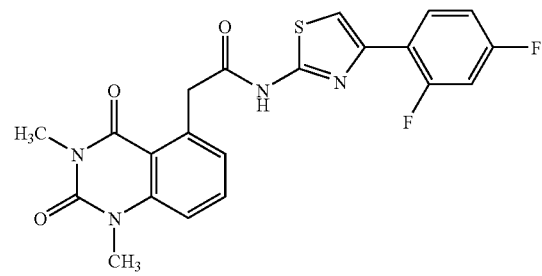

The title compound was prepared according to the general procedure (Method A) by coupling Intermediate 1 (100 mg, 0.403 mmol) with 4-(2,4-difluorophenyl)-1,3-thiazol-2-amine (85 mg, 0.403 mmol) in the presence of EDCI hydrochloride (93 mg, 0.724 mmol), HOBt (54 mg, 0.487 mmol) and DMAP (5 mg, 0.040 mmol) in 1,2-dichloroethane (5 ml) to give 52 mg of the product as an off white solid. $^1$H NMR ($\delta$ ppm, DMSO-d$_6$, 300 MHz): 12.40 (s, 1H); 8.06 (q, J=8.4, 1H); 7.69 (t, J=8.4, 1H); 7.42-7.31 (m, 3H); 7.24-7.16 (m, 2H); 4.33 (s, 2H); 3.53 (s, 3H); 3.21 (s, 3H). IR (cm$^{-1}$, KBr): 3256, 1697, 1651, 1640, 1599, 1551, 1504, 1482, 1426, 1378, 1341, 1316, 1283, 1265, 1170, 1137, 1101, 1060, 1025, 961, 880, 749. MS (m/z): 443.08 ([M+H]$^+$).

Example 32

N1-[4-(3,4-Difluorophenyl)-1,3-thiazol-2-yl]-2-(1,3-dimethyl-2,4-dioxo-1,2,3,4-tetrahydro-5-quinazolinyl)acetamide

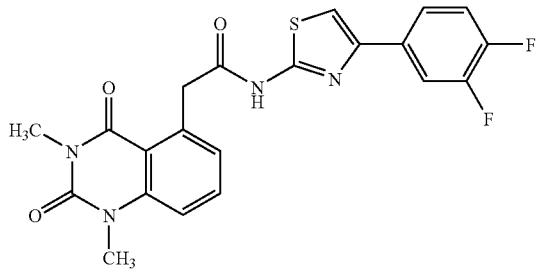

The title compound was prepared according to the general procedure (Method A) by coupling Intermediate 1 (100 mg, 0.403 mmol) with 4-(3,4-difluorophenyl)-1,3-thiazol-2-amine (85 mg, 0.403 mmol) in the presence of EDCI hydrochloride (93 mg, 0.724 mmol), HOBt (54 mg, 0.487 mmol) and DMAP (5 mg, 0.040 mmol) in 1,2-dichloroethane (5 ml) to give 41 mg of the product as an off white solid. $^1$H NMR ($\delta$ ppm, DMSO-d$_6$, 300 MHz): 12.39 (s, 1H); 7.93-7.85 (m, 1H); 7.80-7.62 (m, 2H); 7.64 (s, 1H); 7.54-7.39 (m, 2H); 7.18 (d, J=7.2, 1H); 4.32 (s, 2H); 3.53 (s, 3H); 3.21 (s, 3H). IR (cm$^{-1}$, KBr): 3254, 3215, 1694, 1633, 1601, 1548, 1503, 1485, 1429, 1339, 1280, 1169, 1024, 986, 758. MS (m/z): 443.02 ([M+H]$^+$).

Example 33

N1-[4-(2,6-Difluorophenyl)-1,3-thiazol-2-yl]-2-(1,3-dimethyl-2,4-dioxo-1,2,3,4-tetrahydro-5-quinazolinyl)acetamide

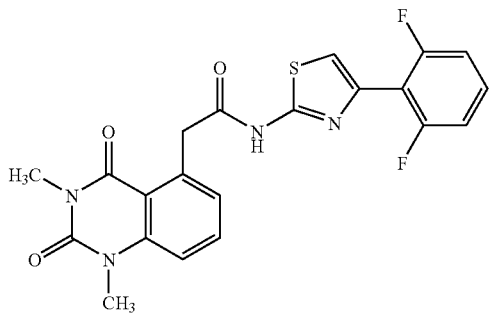

The title compound was prepared according to the general procedure (Method A) by coupling Intermediate 1 (150 mg, 0.604 mmol) with 4-(2,6-difluorophenyl)-1,3-thiazole-2-amine (128 mg, 0.604 mmol) in the presence of EDCI hydrochloride (139 mg, 0.725 mmol), HOBt (81 mg, 0.604 mmol) and DMAP (7.3 mg, 0.060 mmol) in 1,2-dichloroethane (8 ml) to give 110 mg of the product as an off white solid. $^1$H NMR ($\delta$ ppm, DMSO-d$_6$, 300 MHz): 12.43 (s, 1H); 7.69 (t, J=7.8, 1H); 7.48-7.39 (m, 2H); 7.36 (s, 1H); 7.23-7.16 (m, 3H); 4.31 (s, 2H); 3.53 (s, 3H); 3.22 (s, 3H). IR (cm$^{-1}$, KBr): 3274, 2996, 1694, 1626, 1596, 1547, 1503, 1468, 1481, 1412, 1379, 1341, 1311, 1268, 1167, 1002, 961, 814, 793, 722. MS (m/z): 443.04 ([M+H]$^+$).

Example 34

N1-[4-(3,5-Difluorophenyl)-1,3-thiazol-2-yl]-2-(1,3-dimethyl-2,4-dioxo-1,2,3,4-tetrahydro-5-quinazolinyl)acetamide

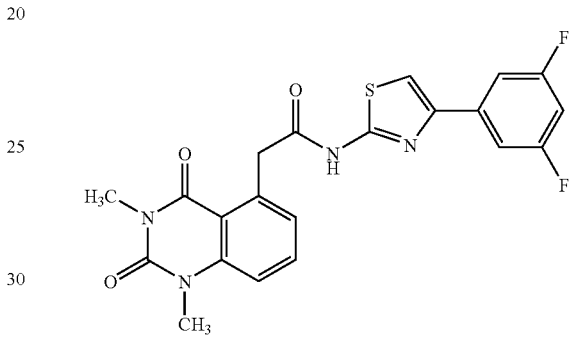

The title compound was prepared according to the general procedure (Method A) by coupling Intermediate 1 (300 mg, 1.209 mmol) with 4-(3,5-difluorophenyl)-1,3-thiazole-2-amine (256 mg, 1.206 mmol) in the presence of EDCI hydrochloride (278 mg, 1.451 mmol), HOBt (163 mg, 1.209 mmol) and DMAP (14 mg, 0.120 mmol) in 1,2-dichloroethane (15 ml) to give 55 mg of the product as an off white solid. $^1$H NMR ($\delta$ ppm, DMSO-d$_6$, 300 MHz): 12.41 (s, 1H); 7.79 (s, 1H); 7.68 (t, J=8.4, 1H); 7.58 (d, J=7.2, 2H); 7.41 (d, J=8.4, 1H); 7.18 (d, J=7.2, 2H); 4.32 (s, 2H); 3.53 (s, 3H); 3.21 (s, 3H). IR (cm$^{-1}$, KBr): 3254, 1693, 1645, 1600, 1552, 1504, 1483, 1434, 1411, 1381, 1334, 1280, 1261, 1162, 1115, 1072, 1028, 983, 948, 856, 812, 746. MS (m/z): 442.96 ([M]$^+$).

Example 35

N1-[4-(2,3-Difluorophenyl)-1,3-thiazol-2-yl]-2-(1,3-dimethyl-2,4-dioxo-1,2,3,4-tetrahydro-5-quinazolinyl)acetamide

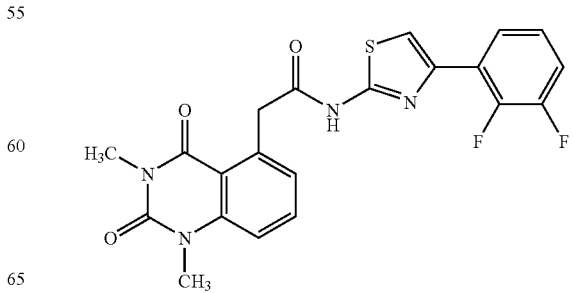

The title compound was prepared according to the general procedure (Method A) by coupling Intermediate 1 (150 mg, 0.604 mmol) with 4-(2,3-difluorophenyl)-1,3-thiazol-2-amine (128 mg, 0.604 mmol) in the presence of EDCI hydrochloride (138 mg, 0.724 mmol), HOBt (81 mg, 0.604 mmol) and DMAP (7 mg, 0.060 mmol) in 1,2-dichloroethane (8 ml) to give 61 mg of the product as an off white solid. $^1$H NMR (δ ppm, DMSO-$d_6$, 300 MHz): 12.44 (s, 1H); 7.85-7.78 (m, 1H); 7.67 (t, J=8.4, 1H); 7.53 (s, 1H); 7.44-7.28 (m, 3H); 7.18 (d, J=7.5, 1H); 4.33 (s, 2H); 3.53 (s, 3H); 3.21 (s, 3H). IR (cm$^{-1}$, KBr): 3214, 1693, 1628, 1599, 1556, 1505, 1450, 1419, 1372, 1338, 1312, 1283, 1268, 1172, 1141, 1074, 1026, 998, 833, 795, 748. MS (m/z): 443.34 ([M+H]$^+$).

Example 36

N1-[4-(2-Fluoro-4-trifluoromethylphenyl)-1,3-thiazol-2-yl]-2-(1,3-dimethyl-2,4-1,2,3,4-tetrahydro-5-quinazolinyl)acetamide

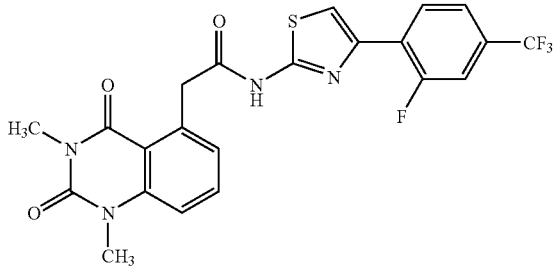

The title compound was prepared according to the general procedure (Method A) by coupling Intermediate 1 (100 mg, 0.403 mmol) with 4-(2-fluoro-4-trifluoromethylphenyl)-1,3-thiazol-2-amine (105 mg, 0.403 mmol) in the presence of EDCI hydrochloride (93 mg, 0.483 mmol), HOBt (54 mg, 0.403 mmol) and DMAP (5 mg, 0.040 mmol) in 1,2-dichloroethane (5 ml) to give 21 mg of the product as an off white solid. $^1$H NMR (δ ppm, DMSO-$d_6$, 300 MHz): 12.50 (s, 1H); 8.32-8.20 (m, 1H); 7.82-7.65 (m, 4H); 7.43 (d, J=8.7, 1H); 7.19 (d, J=7.8, 1H); 4.34 (s, 2H); 3.54 (s, 3H); 3.21 (s, 3H). MS (m/z): 493.11 ([M+H]$^+$).

Example 37

N1-[4-(3-Fluoro-4-trifluoromethylphenyl)-1,3-thiazol-2-yl]-2-(1,3-dimethyl-2,4-dioxo-1,2,3,4-tetrahydro-5-quinazolinyl)acetamide

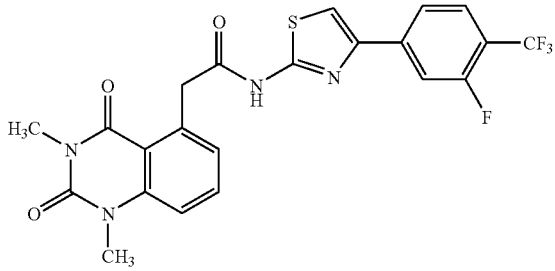

The title compound was prepared according to the general procedure (Method A) by coupling Intermediate 1 (125 mg, 0.504 mmol) with 4-(3-fluoro-4-trifluoromethylphenyl)-1,3-thiazol-2-amine (131 mg, 0.504 mmol) in the presence of EDCI hydrochloride (115 mg, 0.604 mmol), HOBt (67 mg, 0.504 mmol) and DMAP (6 mg, 0.050 mmol) in 1,2-dichloroethane (7 ml) to give 30 mg of the product as an off white solid. $^1$H NMR (δ ppm, DMSO-$d_6$, 300 MHz): 12.48 (s, 1H); 8.00-7.80 (m, 4H); 7.78-7.60 (m, 1H); 7.42 (d, J=7.8, 1H); 7.19 (d, J=6.3, 1H); 4.33 (s, 2H); 3.54 (s, 3H); 3.21 (s, 3H). IR (cm$^{-1}$, KBr): 3095, 2975, 1698, 1630, 1600, 1581, 1502, 1483, 1430, 1377, 1331, 1288, 1128, 1072, 1045, 1026, 971, 879, 762. MS (m/z): 491.18 ([M−H]$^+$).

Example 38

N1-[4-(4-Fluoro-3-trifluoromethylphenyl)-1,3-thiazol-2-yl]-2-(1,3-dimethyl-2,4-dioxo-1,2,3,4-tetrahydro-5-quinazolinyl)acetamide

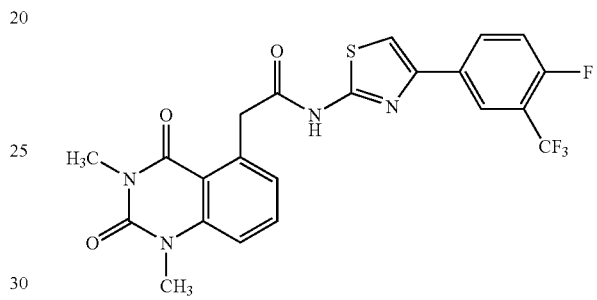

The title compound was prepared according to the general procedure (Method A) by coupling Intermediate 1 (100 mg, 0.403 mmol) with 4-(4-fluoro-3-trifluoromethylphenyl)-1,3-thiazole-2-amine (105 mg, 0.403 mmol) in the presence of EDCI hydrochloride (92 mg, 0.483 mmol), HOBt (16 mg, 0.120 mmol) and DMAP (4.8 mg, 0.040 mmol) in 1,2-dichloroethane (5 ml) to give 41 mg of the product as an off white solid. $^1$H NMR (δ ppm, DMSO-d6, 300 MHz): 12.45 (s, 1H); 8.27-8.20 (m, 2H); 7.77 (s, 1H); 7.76-7.45 (m, 2H); 7.42 (d, J=7.8, 1H); 7.19 (d, J=7.8, 1H); 4.32 (s, 2H); 3.53 (s, 3H); 3.21 (s, 3H). IR (cm$^{-1}$, KBr): 3208, 2977, 1694, 1645, 1601, 1547, 1483, 1414, 1344, 1312, 1271, 1198, 1165, 1127, 1069, 1052, 1026, 965, 812. MS (m/z): 493.06 ([M+H]$^+$).

Example 39

N1-[4-(4-Fluoro-2-trifluoromethylphenyl)-1,3-thiazol-2-yl]-2-(1,3-dimethyl-2,4-dioxo-1,2,3,4-tetrahydro-5-quinazolinyl)acetamide

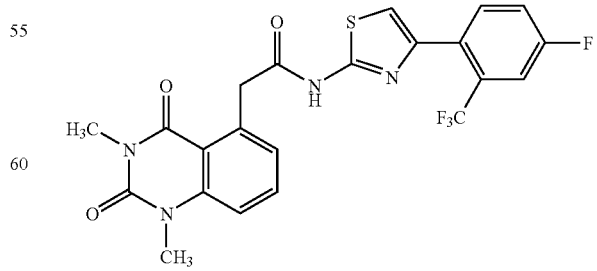

The title compound was prepared according to the general procedure (Method A) by coupling Intermediate 1 (150 mg, 0.604 mmol) with 4-(4-fluoro-2-trifluoromethylphenyl)-1,3-thiazole-2-amine (158 mg, 0.604 mmol) in the presence of EDCI hydrochloride (139 mg, 0.725 mmol), HOBt (81 mg, 0.604 mmol) and DMAP (14 mg, 0.120 mmol) in 1,2-dichloroethane (6 ml) to give 75 mg of the product as an off white solid. $^1$H NMR (δ ppm, DMSO-$d_6$, 300 MHz): 12.32 (s, 1H); 7.73-7.56 (m, 4H); 7.41 (d, J=8.1, 1H); 7.21-7.15 (m, 2H); 4.32 (s, 2H); 3.53 (s, 3H); 3.23 (s, 3H). IR (cm$^{-1}$, KBr): 3205, 2926, 1694, 1673, 1601, 1556, 1502, 1484, 1419, 1380, 1341, 1320, 1282, 1250, 1215, 1163, 1136, 1073, 1025, 961, 920, 812, 753. MS (m/z): 493.15 ([M+H]$^+$).

Example 40

N1-[4-(2-Fluoro-5-trifluoromethylphenyl)-1,3-thiazol-2-yl]-2-(1,3-dimethyl-2,4-dioxo-1,2,3,4-tetrahydro-5-quinazolinyl)acetamide

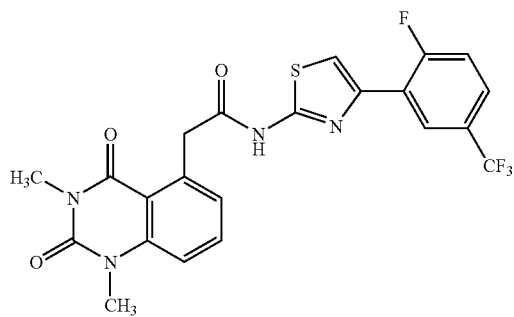

The title compound was prepared according to the general procedure procedure (Method B) by coupling Intermediate 1 (284 mg, 1.145 mmol) with 4-(2-fluoro-5-trifluoromethylphenyl)-1,3-thiazol-2-amine (300 mg, 1.145 mmol) in the presence of EDCI hydrochloride (263.2 mg, 1.374 mmol), DMAP (14 mg, 0.114 mmol) in the mixture of THF:DMF (3:1, 14 ml) to give 10 mg of the product as a pale yellow solid. $^1$H NMR (δ ppm, DMSO-$d_6$, 300 Hz): 12.49 (s, 1H); 8.40 (d, J=5.7, 1H); 7.71-7.76 (m, 1H); 7.54-7.66 (m, 3H); 7.41 (d, J=8.7, 1H); 7.18 (d, J=7.2, 1H); 4.32 (s, 2H); 3.53 (s, 3H); 3.21 (s, 3H). IR (cm$^{-1}$, KBr): 3445, 2928, 1693, 1647, 1600, 1545, 1504, 1480, 1466, 1407, 1381, 1339, 1278, 1250, 1187, 1157, 1120, 1071, 1025, 965, 826, 750. MS (m/z): 492.95 ([M]$^+$).

Example 41

N1-[4-(3-Fluoro-4-trifluoromethoxyphenyl)-1,3-thiazol-2-yl]-2-(1,3-dimethyl-2,4-dioxo-1,2,3,4-tetrahydro-5-quinazolinyl)propanamide

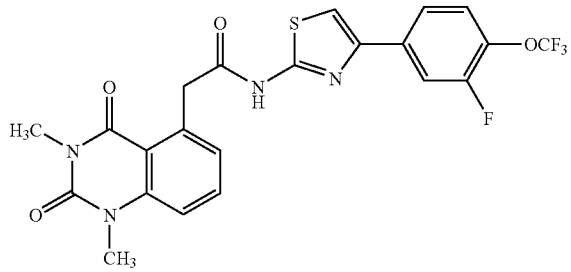

The title compound was prepared according to the general procedure procedure (Method B) by coupling Intermediate 1 (200 mg, 0.806 mmol) with 4-(3-fluoro-4-trifluoromethoxyphenyl)-1,3-thiazole-2-amine (224 mg, 0.806 mmol) in the presence of EDCI hydrochloride (309 mg, 1.612 mmol), and DMAP (19 mg, 0.161 mmol) in the mixture of THF:DMF (3:1, 4 ml) to give 55 mg of the product as an off white solid. $^1$H NMR (δ ppm, DMSO-$d_6$, 300 Hz): 12.46 (s, 1H); 8.00-7.95 (m, 1H); 7.96 (d, J=8.4, 1H); 7.77 (s, 1H); 7.75-7.60 (m, 2H); 7.44 (d, J=9.0, 1H); 7.20 (d, J=7.2, 1H); 4.34 (s, 2H); 3.54 (s, 3H); 3.22 (s, 3H). IR (cm$^{-1}$, KBr): 3218, 2925, 1686, 1641, 1602, 1544, 1504, 1483, 1412, 1380, 1315, 1279, 1259, 1220, 1168, 1027, 971, 877, 750. MS (m/z): 508.97 ([M]$^+$).

Example 42

N1-[4-(4-Fluoro-3-trifluoromethoxyphenyl)-1,3-thiazol-2-yl]-2-(1,3-dimethyl-2,4-dioxo-1,2,3,4-tetrahydro-5-quinazolinyl)propanamide

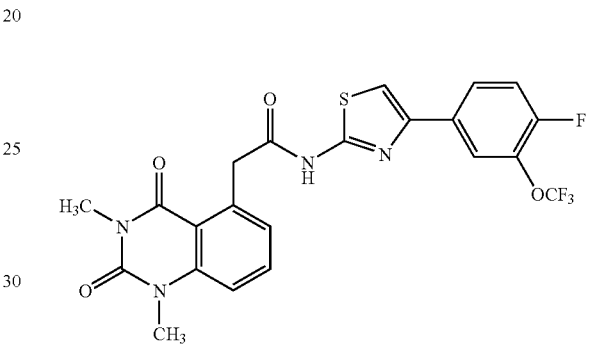

The title compound was prepared according to the general procedure procedure (Method B) by coupling Intermediate 1 (200 mg, 0.806 mmol) with 4-(4-fluoro-3-trifluoromethoxyphenyl)-1,3-thiazole-2-amine (224 mg, 0.806 mmol) in the presence of EDCI (309 mg, 1.162 mmol) and DMAP (19 mg, 0.161 mmol) in mixture of tetrahydrofuran and DMF (3:1 ratio, 8 ml) to give 25 mg of the title compound as an off white solid. $^1$H NMR (δ ppm, DMSO-$d_6$, 300 Hz): 12.47 (s, 1H); 8.06-7.97 (m, 2H); 7.76-7.68 (m, 2H); 7.60 (t, J=8.7, 1H); 7.44 (d, J=8.4, 1H); 7.20 (d, J=7.2, 1H); 4.34 (s, 2H); 3.54 (s, 3H); 3.22 (s, 3H). MS (m/z): 508.97 ([M]$^+$).

Example 43

N1-[4-(3-Fluoro-4-methoxyphenyl)-1,3-thiazol-2-yl]-2-(1,3-dimethyl-2,4-dioxo-1,2,3,4-tetrahydro-5-quinazolinyl)propanamide

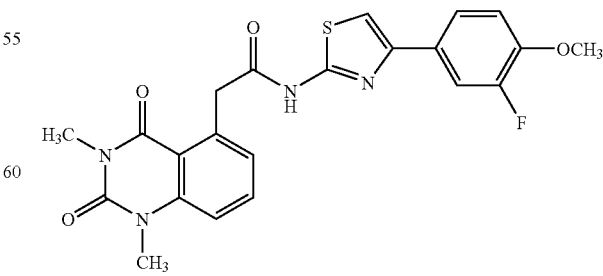

The title compound was prepared according to the general procedure procedure (Method B) by coupling Intermediate 1

(250 mg, 1.008 mmol) with 4-(3-fluoro-4-methoxyphenyl)-1,3-thiazole-2-amine (225 mg, 1.008 mmol) in the presence of EDCI (386 mg, 2.016 mmol) and DMAP (24 mg, 0.201 mmol) in mixture of tetrahydrofuran and DMF (3:1 ratio, 12 ml) to give 165 mg of the title compound as an off white solid. $^1$H NMR (δ ppm, DMSO-$d_6$, 300 Hz): 12.39 (s, 1H); 7.75-7.69 (m, 3H); 7.52 (s, 1H); 7.44 (d, J=8.4, 1H); 7.28-7.18 (m, 2H); 4.33 (s, 2H); 3.88 (s, 3H); 3.54 (s, 3H); 3.22 (s, 3H). IR (cm$^{-1}$, KBr): 3249, 2950, 1693, 1643, 1601, 1547, 1504, 1481, 1410, 1335, 1310, 1279, 1261, 1220, 1168, 1034, 1024, 924, 816. MS (m/z): 453.07 ([M−H]$^+$).

Example 44

N1-[4-(4-Difluoromethoxyl-3-fluorophenyl)-1,3-thiazol-2-yl]-2-(1,3-dimethyl-2,4-dioxo-1,2,3,4-tetrahydro-5-quinazolinyl)acetamide

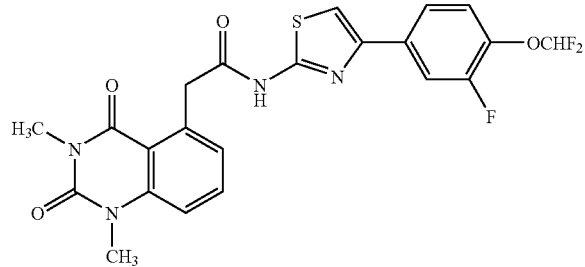

The title compound was prepared according to the general procedure (Method A) by coupling Intermediate 1 (200 mg, 0.806 mmol) with 4-(4-difluoromethoxyl-3-fluorophenyl)-1,3-thiazole-2-amine (195 mg, 0.806 mmol) in the presence of EDCI (185 mg, 0.967 mmol), HOBt (108 mg, 0.806 mmol) and DMAP (9 mg, 0.080 mmol) in 1,2-dichloroethane (10 ml) to give 31 mg of the title compound as an off white solid. $^1$H NMR (δ ppm, DMSO-$d_6$, 300 MHz): 12.41 (s, 1H); 7.83-7.89 (m, 1H); 7.76 (d, J=8.7, 1H); 7.65-7.71 (m, 2H); 7.40-7.51 (m, 2H); 7.27 (s, 1H); 7.18 (d, J=7.2, 1H); 4.32 (s, 2H); 3.53 (s, 3H); 3.21 (s, 3H). IR (cm$^{-1}$, KBr): 3248, 3213, 1690, 1640, 1602, 1546, 1504, 1482, 1409, 1380, 1329, 1279, 1262, 1129, 1110, 1059, 969, 877, 787, 750 MS (m/z): 489.33 ([M−H]$^+$).

Example 45

N1-[4-(2,4-Dichlorophenyl)-1,3-thiazol-2yl]-2-(1,3-dimethyl-2,4-dioxo-1,2,3,4-tetrahydro-5-quinazolinyl)acetamide

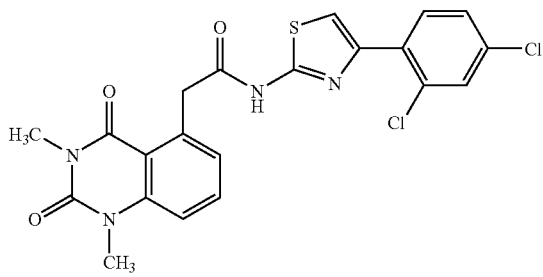

The title compound was prepared according to the general procedure (Method A) by coupling Intermediate 1 (200 mg, 0.806 mmol) with 4-(2,4-dichlorophenyl)-1,3-thiazol-2-amine (197 mg, 0.806 mmol) in the presence of EDCI hydrochloride (185 mg, 0.967 mmol), HOBt (33 mg, 0.241 mmol) and DMAP (10 mg, 0.040 mmol) in 1,2-dichloroethane (5 ml) to give 93 mg of the title compound as an off white solid. $^1$H NMR (δ ppm, DMSO-$d_6$, 300 MHz): 12.43 (br. s, 1H); 7.88 (d, J=8.7, 1H); 7.75-7.65 (m, 2H); 7.59 (s, 1H); 7.53 (d, J=8.4, 1H); 7.42 (d, J=8.1, 1H); 7.19 (d, J=7.2, 1H); 4.32 (s, 2H); 3.54 (s, 3H); 3.22 (s, 3H). IR (cm$^{-1}$, KBr): 3267, 3137, 2983, 2921, 1698, 1688, 1632, 1600, 1565, 1546, 1506, 1481, 1421, 1374, 1340, 1316, 1302, 1286, 1261, 1253, 1205, 1170, 1145, 1112, 1076, 1040, 1028, 962, 906, 881, 853, 831, 817, 792, 745, 696, 667. MS (m/z): 475.37 ([M+H]$^+$).

Example 46

N1-[4-(2,5-Dichlorophenyl)-1,3-thiazol-2-yl]-2-(1,3-dimethyl-2,4-dioxo-1,2,3,4-tetrahydro-5-quinazolinyl)acetamide

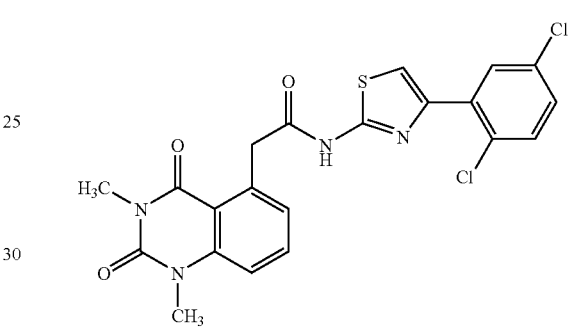

The title compound was prepared according to the general procedure (Method A) by coupling Intermediate 1 (100 mg, 0.403 mmol) with 4-(2,5-dichlorophenyl)-1,3-thiazol-2-amine (98 mg, 0.403 mmol) in the presence of EDCI hydrochloride(93 mg, 0.483 mmol), HOBt (16 mg, 0.121 mmol) and DMAP (5 mg, 0.040 mmol) in 1,2-dichloroethane (5 ml) to give 30 mg of the title compound as an off white solid. $^1$H NMR (δ ppm, DMSO-$d_6$, 300 MHz): 12.44 (s, 1H); 7.95 (s, 1H), 7.75-7.60 (m, 2H); 7.59 (d, J=8.4, 1H); 7.45-7.40 (m, 2H); 7.19 (d, J=7.2, 1H); 4.33 (s, 2H); 3.54 (s, 3H); 3.22 (s, 3H). IR (cm$^{-1}$, KBr): 3249, 3225, 1697, 1687, 1641, 1600, 1557, 1542, 1502, 1481, 1377, 1337, 1279, 1165, 1097, 1039, 1024, 966, 812 MS (m/z): 475.77 ([M+H]$^+$).

Example 47

N1-[4-(3,4-Dichlorophenyl)-1,3-thiazol-2yl]-2-(1,3-dimethyl-2,4-dioxo-1,2,3,4-tetrahydro-5-quinazolinyl)acetamide

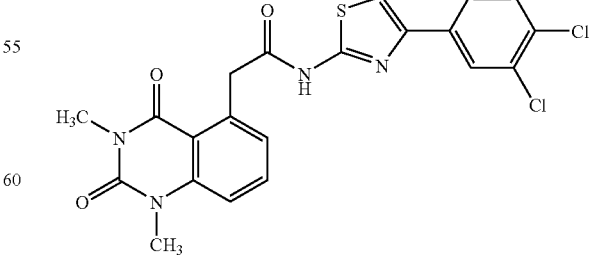

The title compound was prepared according to the general procedure (Method A) by coupling Intermediate 1 (200 mg, 0.806 mmol) with 4-(3,4-dichlorophenyl)-1,3-thiazol-2- amine (197 mg, 0.806 mmol) in the presence of EDCI hydrochloride (214 mg, 1.116 mmol), HOBt (32 mg, 0.241 mmol) and DMAP (10 mg, 0.040 mmol) in 1,2-dichloroethane (10 ml) to give 68 mg of the title compound as an off white solid. $^1$H NMR (δ ppm, DMSO-d$_6$, 300 MHz): 12.40 (br. s, 1H); 8.12 (br. s, 1H); 7.86 (d, J=7.8, 1H); 7.77-7.65 (m, 3H); 7.41 (d, J=7.8, 1H); 7.18 (d, J=7.8, 1H); 4.32 (br. s, 2H); 3.53 (s, 3H); 3.21 (s, 3H). IR (cm$^{-1}$, KBr): 3252, 3217, 1691, 1041, 1600, 1542, 1504, 1481, 1432, 1408, 1380, 1312, 1161, 1142, 1161, 1069, 1027, 748. MS (m/z): 477.48 ([M+H]$^+$).

Example 48

N1-[4-(3,5-Dichlorophenyl)-1,3-thiazol-2-yl]-2-(1,3-dimethyl-2,4-dioxo-1,2,3,4-tetrahydro-5-quinazolinyl)acetamide

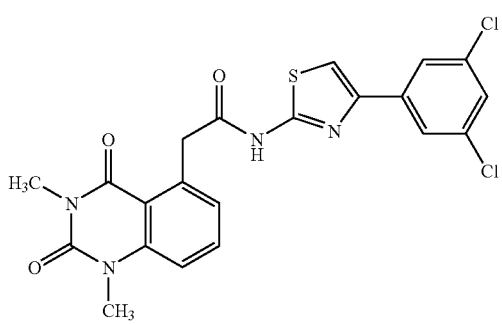

The title compound was prepared according to the general procedure (Method A) by coupling Intermediate 1 (200 mg, 0.806 mmol) with 4-(3,5-Dichlorophenyl)-1,3-thiazol-2-amine (197 mg, 0.806 mmol) in the presence of EDCI hydrochloride (185 mg, 0.967 mmol), HOBt (108 mg, 0.806 mmol) and DMAP (10 mg, 0.080 mmol) in 1,2-dichloroethane (10 ml) to give 46 mg of the title compound as an off white solid. $^1$H NMR (δ ppm, DMSO-d$_6$, 300 Hz): 12.41 (s, 1H); 7.93 (s, 2H); 7.85 (s, 1H); 7.68 (t, J=7.8, 1H); 7.54 (s, 1H); 7.42 (d, J=8.4, 1H), 7.18 (d, J=7.5, 1H); 4.32 (s, 2H); 3.53 (s, 3H); 3.21 (s, 3H). IR (cm$^{-1}$, KBr): 3261, 2953, 1692, 1643, 1601, 1568, 1550, 1503, 1431, 1408, 1379, 1304, 1280, 1162, 1078, 1027, 968, 878, 797, 748. MS (m/z): 475.31 ([M+H]$^+$).

Example 49

N1-[4-(3-Chloro-4-fluorophenyl)-1,3-thiazol-2-yl]-2-(1,3-dimethyl-2,4-dioxo-1,2,3,4-tetrahydro-5-quinazolinyl)acetamide

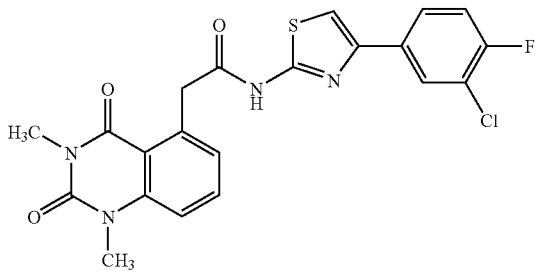

The title compound was prepared according to the general procedure (Method A) by coupling Intermediate 1 (100 mg, 0.403 mmol) with 4-(3-chloro-4-fluorophenyl)-1,3-thiazol-2-amine (92 mg, 0.403 mmol) in the presence of EDCI hydrochloride (93 mg, 0.483 mmol), HOBt (16 mg, 0.121 mmol) and DMAP (5 mg, 0.040 mmol) in 1,2-dichloroethane (5 ml) to give 21 mg of the title compound as an off white solid. $^1$H NMR (δ ppm, DMSO-d$_6$, 300 MHz): 12.39 (s, 1H); 8.08 (d, J=7.2, 1H); 7.95-7.80 (m, 1H); 7.75-7.70 (m, 2H); 7.55-7.35 (m, 2H); 7.19 (d, J=7.2, 1H); 4.33 (s, 2H); 3.54 (s, 3H); 3.22 (s, 3H). IR (cm$^{-1}$, KBr): 3251, 3222, 2961, 1693, 1642, 1601, 1547, 1504, 1482, 1432, 1409, 1337, 1313, 1281, 1258, 1168, 1073, 737. MS (m/z): 457.30 ([M+H]$^+$).

Example 50

N1-[4-(3-Chloro-2-fluorophenyl)-1,3-thiazol-2-yl]-2-(1,3-dimethyl-2,4-dioxo-1,2,3,4-tetrahydro-5-quinazolinyl)acetamide

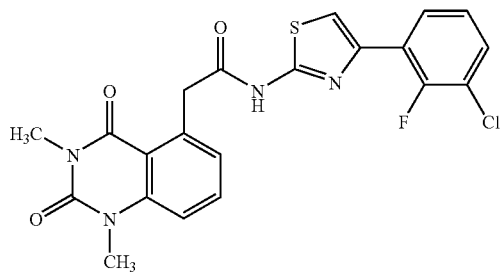

The title compound was prepared according to the general procedure (Method A) by coupling Intermediate 1 (200 mg, 0.806 mmol) with 4-(3-chloro-2-fluorophenyl)-1,3-thiazol-2-amine (192 mg, 0.806 mmol) in the presence of EDCI hydrochloride (185 mg, 0.967 mmol), HOBt (108 mg, 0.806 mmol) and DMAP (10 mg, 0.080 mmol) in 1,2-dichloroethane (10 ml) to give 48 mg of the title compound as an off white solid. $^1$H NMR (δ ppm, DMSO-d$_6$, 300 MHz): 12.44 (s, 1H); 7.98 (t, J=7.8, 1H); 7.69 (t, J=7.8, 1H); 7.60-7.50 (m, 2H); 7.41 (d, J=8.1, 1H); 7.32 (t, J=7.8, 1H); 7.18 (d, J=7.5, 1H); 4.33 (s, 2H); 3.53 (s, 3H); 3.21 (s, 3H). IR (cm$^{-1}$, KBr): 3226, 2948, 1701, 1634, 1602, 1546, 1504, 1483, 1426, 1339, 1305, 1289, 1238, 1185, 1164, 1075, 1023, 985, 810, 762. MS (m/z): 459.31 ([M+H]$^+$).

Example 51

N1-[4-(4-Chloro-2-fluorophenyl)-1,3-thiazol-2-yl]-2-(1,3-dimethyl-2,4-dioxo-1,2,3,4-tetrahydro-5-quinazolinyl)acetamide

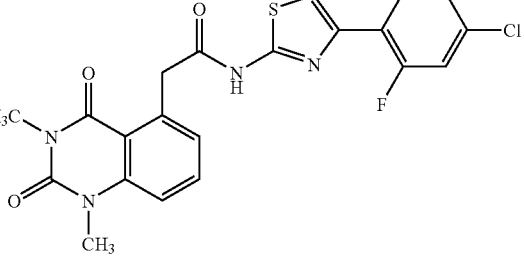

The title compound was prepared according to the general procedure (Method A) by coupling Intermediate 1 (100 mg, 0.403 mmol) with 4-(4-chloro-2-fluorophenyl)-1,3-thiazol- 2-amine (92 mg, 0.403 mmol) in the presence of EDCI hydrochloride (92 mg, 0.483 mmol), HOBt (54 mg, 0.403 mmol) and DMAP (5 mg, 0.040 mmol) in 1,2-dichloroethane (5 ml) to give 41 mg of the product as an off white solid. $^1$H NMR (δ ppm, DMSO-d$_6$, 300 MHz): 12.42 (s, 1H); 8.07 (t, J=8.1, 1H); 7.73-7.65 (m, 1H); 7.58-7.39 (m, 4H); 7.18 (d, J=7.5, 1H); 4.33 (s, 2H); 3.53 (s, 3H); 3.21 (s, 3H). IR (cm$^{-1}$, KBr): 3254, 3226, 1697, 1628, 1610, 1599, 1578, 1556, 1505, 1479, 1421, 1315, 1284, 1270, 1218, 1171, 1082, 1060, 1027, 917, 747. MS (m/z): 459.18 ([M+H]$^+$).

Example 52

N1-[4-(5-Chloro-2-fluorophenyl)-1,3-thiazol-2-yl]-2-(1,3-dimethyl-2,4-dioxo-1,2,3,4-tetrahydro-5-quinazolinyl)acetamide

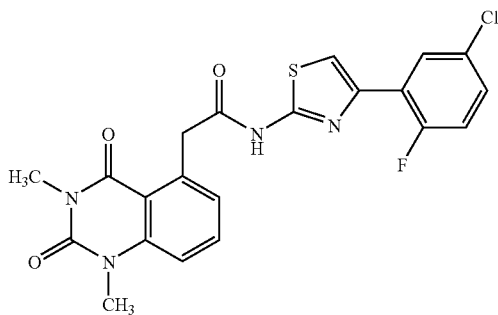

The title compound was prepared according to the general procedure (Method A) by coupling Intermediate 1 (200 mg, 0.806 mmol) with 4-(5-chloro-2-fluorophenyl)-1,3-thiazol-2-amine (211 mg, 0.806 mmol) in the presence of EDCI hydrochloride (185 mg, 0.967 mmol), HOBt (108 mg, 0.806 mmol) and DMAP (10 mg, 0.080 mmol) in 1,2-dichloroethane (8 ml) to give 41 mg of the title compound as an off white solid. $^1$H NMR (δ ppm, DMSO-d6, 300 MHz): 12.43 (s, 1H); 8.06-8.02 (m, 1H); 7.69 (t, J=7.8, 1H); 7.54 (s, 1H); 7.44-7.32 (m, 3H); 7.19 (d, J=7.2, 1H); 4.33 (s, 2H); 3.53 (s, 3H); 3.21 (s, 3H). IR (cm$^{-1}$, KBr): 3225, 2963, 1694, 1645, 1600, 1547, 1504, 1482, 1409, 1380, 1339, 1279, 1243, 1160, 1188, 1062, 964, 810, 750. MS (m/z): 457.38 ([M−H]$^+$).

Example 53

N1-[4-(2-Chloro-6-fluorophenyl)-1,3-thiazol-2-yl]-2-(1,3-dimethyl-2,4-dioxo-1,2,3,4-tetrahydro-5-quinazolinyl)acetamide

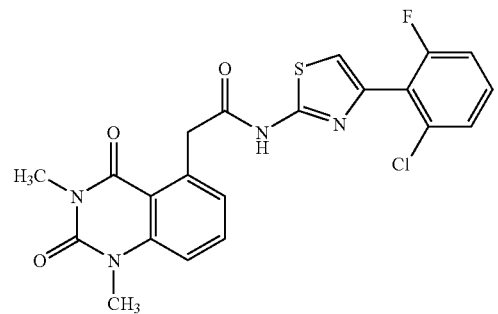

The title compound was prepared according to the general procedure (Method A) by coupling Intermediate 1 (150 mg, 0.604 mmol) with 4-(2-chloro-6-fluorophenyl)-1,3-thiazol-2-amine (136 mg, 0.604 mmol) in the presence of EDCI hydrochloride (139 mg, 0.724 mmol), HOBt (81 mg, 0.604 mmol) and DMAP (7 mg, 0.060 mmol) in 1,2-dichloroethane (5 ml) to give 55 mg of the product as an off white solid. $^1$H NMR (δ ppm, DMSO-d$_6$, 300 MHz): 12.39 (s, 1H); 7.69 (t, J=8.1, 1H); 7.50-7.40 (m, 4H); 7.36-7.40 (m, 4H); 7.36-7.27 (m, 1H); 7.18 (d, J=7.2, 1H); 4.31 (s, 2H); 3.53 (s, 3H); 3.23 (s, 3H). IR (cm$^{-1}$, KBr): 3219, 1712, 1683, 1633, 1602, 1551, 1504, 1480, 1448, 1424, 1409, 1375, 1337, 1319, 1312, 1284, 1244, 1183, 1157, 1074, 1027, 961, 865, 790, 776, 759. MS (m/z): 459.45 ([M+H]$^+$).

Example 54

N1-[4-(2-Chloro-4-fluorophenyl)-1,3-thiazol-2-yl]-2-(1,3-dimethyl-2,4-dioxo-1,2,3,4-tetrahydro-5-quinazolinyl)propanamide

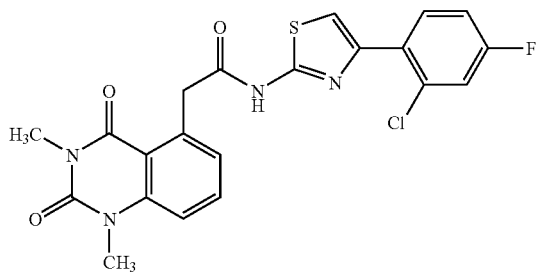

The title compound was prepared according to the general procedure (Method A) by coupling Intermediate 1 (163 mg, 0.657 mmol) with 4-(2-chloro-4-fluorophenyl)-1,3-thiazol-2-amine (150 mg, 0.657 mmol) in the presence of EDCI hydrochloride (150 mg, 0.785 mmol), HOBt (88 mg, 0.657 mmol) and DMAP (8 mg, 0.065 mmol) in 1,2-dichloroethane (7 ml) to give 89 mg of the product as an off white solid. $^1$H NMR (δ ppm, DMSO-d$_6$, 300 Hz): 12.39 (s, 1H); 7.86 (t J=7.8, 1H); 7.69 (t, J=8.4, 1H); 7.50-7.56 (m, 2H); 7.41 (d, J=8.4, 1H); 7.32 (t, J=8.1, 1H); 7.18 (d, J=7.8, 1H); 4.32 (s, 2H); 3.54 (s, 3H); 3.22 (s, 3H). MS (m/z): 459.02 ([M+H]$^+$).

Example 55

N1-[4-(4-Chloro, 3-trifluoromethylphenyl)-1,3-thiazol-2-yl]-2-(1,3-dimethyl-2,4-dioxo-1,2,3,4-tetrahydro-5-quinazolinyl)acetamide

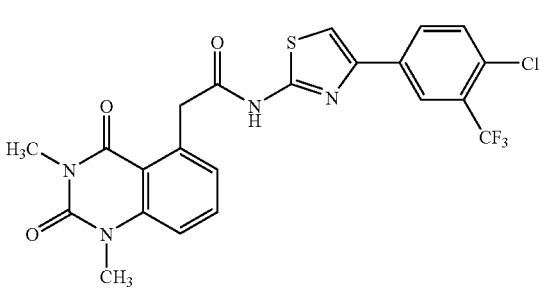

The title compound was prepared according to the general procedure (Method B) by coupling Intermediate 1 (200 mg, 0.806 mmol) with 4-(4-chloro-3-trifluoromethylphenyl)-1,3-thiazol-2-amine (224 mg, 0.806 mmol) in the presence of EDCI hydrochloride (185 mg, 0.967 mmol) and DMAP (10 mg, 0.080 mmol) in the mixture of THF:DMF (3:1, 9.67 ml)

to give 30 mg of the product as an off white solid. $^1$H NMR (δ ppm, DMSO-$d_6$, 300 MHz): 12.43 (s, 1H); 8.34 (s, 1H); 8.19 (d, J=6.3, 1H); 7.84 (s, 1H); 7.79 (d, J=6.3, 1H); 7.69 (t, J=6.1, 1H); 7.42 (d, J=6.3, 1H); 7.19 (d, J=5.5, 1H); 4.34 (s, 2H); 3.53 (s. 3H); 3.21 (s, 3H). MS (m/z): 509.22 ([M+H]$^+$).

Example 56

N1-[4-(2-Chloro-5-trifuoromethylphenyl)-1,3-thiazol-2-yl]-2-(1,3-dimethyl-2,4-dioxo-1,2,3,4-tetrahydro-5-quinazolinyl)propanamide

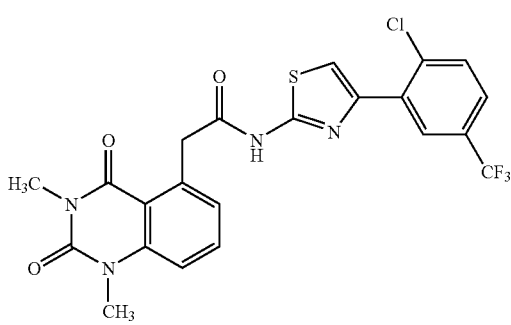

The title compound was prepared according to the general procedure (Method A) by coupling Intermediate 1 (200 mg, 0.806 mmol) with 4-(2-chloro-5-trifuoromethylphenyl)-1,3-thiazol-2-amine (224 mg, 0.806 mmol) in the presence of EDCI hydrochloride (185 mg, 0.967 mmol), HOBt (108 mg, 0.806 mmol) and DMAP (10 mg, 0.080 mmol) in 1,2-dichloroethane (10 ml) to give 31 mg of the title compound as an off white solid. $^1$H NMR (δ ppm, DMSO-$d_6$, 300 Hz): 12.52 (s, 1H), 8.30 (s, 1H); 7.88-7.67 (m, 4H); 7.44 (d, J=8.1, 1H); 7.21 (d, J=7.5, 1H); 4.34 (s, 2H); 3.55 (s, 3H); 3.23 (s, 3H). IR (cm$^{-1}$, KBr): 3291, 2971, 1698, 1644, 1601, 1544, 1503, 1480, 1410, 1384, 1337, 1279, 1242, 1164, 1123, 1073, 1024, 964, 812, 751. MS (m/z): 508.51 ([M]$^+$).

Example 57

N1-{4-[3-Chloro-4-(difluoromethoxy)phenyl]-1,3-thiazol-2-yl}-2-(1,3-dimethyl-2,4-dioxo-1,2,3,4-tetrahydro-5-quinazolinyl)acetamide

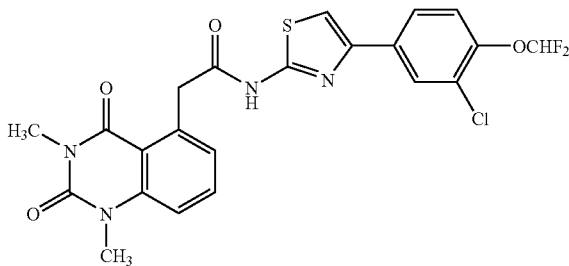

The title compound was prepared according to the general procedure (Method A) by coupling Intermediate 1 (200 mg, 0.806 mmol) with 4-[3-chloro-4-(difluoromethoxy)phenyl]-1,3-thiazol-2-amine (223 mg, 0.806 mmol) in the presence of EDCI (310 mg, 1.612 mmol) and DMAP (20 mg, 0.161 mmol) in mixture of tetrahydrofuran and DMF (3:1 ratio, 16 ml) to give 112 mg of the title compound as an off white solid. $^1$H NMR (δ ppm, DMSO-$d_6$, 300 Hz): 12.46 (s, 1H); 8.12 (s, 1H); 7.88 (d, J=8.7, 1H); 7.76-7.69 (m, 2H); 7.44 (d, J=8.4, 2H), 7.33 (t, J=73.2, 1H); 7.18 (d, J=7.2, 1H); 4.34 (s, 2H); 3.54 (s, 3H); 3.22 (s, 3H). MS (m/z): 506.96 ([M]$^+$).

Example 58

N1-[4-(4-Chloro-3-methylphenyl)-1,3-thiazol-2yl]-2-(1,3-dimethyl-2,4-dioxo-1,2,3,4-tetrahydro-5-quinazolinyl)acetamide

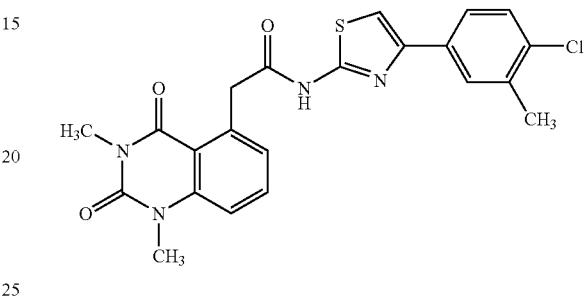

The title compound was prepared according to the general procedure (Method A) by coupling Intermediate 1 (200 mg, 0.806 mmol) with 4-(4-chloro-3-methylphenyl)-1,3-thiazol-2-amine (180 mg, 0.806 mmol) in the presence of EDCI hydrochloride (184 mg, 0.967 mmol), HOBt (32 mg, 0.241 mmol) and DMAP (10 mg, 0.080 mmol) in 1,2-dichloroethane (10 ml) to give 190 mg of the product as an off white solid. $^1$H NMR (δ ppm, DMSO-$d_6$, 300 MHz): 12.38 (br. s, 1H); 7.87 (br. s, 1H); 7.74-7.64 (m, 2H); 7.57 (br. s, 1H); 7.42 (t, J=9.0, 2H): 7.17 (d, J=7.5, 1H); 4.31 (s, 2H); 3.53 (s, 3H); 3.21 (s, 3H); 2.38 (s, 3H). IR (cm$^{-1}$, KBr): 3258, 3219, 1689, 1642, 1601, 1547, 1504, 1481, 1429, 1409, 1378, 1340, 1315, 1280, 1160, 1075, 1045, 1025, 750. MS (m/z): 455.18 ([M+H]$^+$).

Example 59

N1-{4-[3-fluoro-4-(2,2,2-trifluoroethoxy)phenyl]-1,3-thiazol-2yl}-2-(1,3-dimethyl-2,4-dioxo-1,2,3,4-tetrahydro-5-quinazolinyl)acetamide

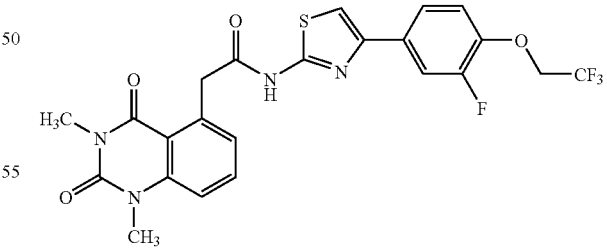

The title compound was prepared according to the general procedure (Method B) by coupling Intermediate 1 (250 mg, 1.008 mmol) with 4-[4-fluoro-3-(2,2,2-trifluoroethoxy)phenyl]-1,3-thiazol-2-amine (294 mg, 1.008 mmol) in the presence of EDCI hydrochloride (386 mg, 2.016 mmol) and DMAP (24 mg, 0.201 mmol) in the mixture of THF:DMF (3:1, 5.04 ml) to give 200 mg of the product as an off white solid. $^1$H NMR (δ ppm, DMSO-$d_6$, 300 Hz): 12.41 (s, 1H);

7.82-7.67 (m, 3H); 7.60 (s, 1H); 7.46-7.33 (m, 2H); 7.21 (d, J=7.2, 1H); 4.95-4.85 (m, 2H); 4.33 (s, 2H); 3.54 (s, 3H); 3.22 (s, 3H). IR (cm$^{-1}$, KBr): 3207, 2965, 1689, 1640, 1602, 1547, 1504, 1482, 1415, 1380, 1336, 1279, 1261, 1167, 1138, 1071, 1027, 968, 812, 750. MS (m/z): 523.07 ([M+H]$^+$).

Example 60

N1-[4-(4-Cyclopropylmethoxy-3-fluorophenyl)-1,3-thiazol-2yl]-2-(1,3-dimethyl-2,4-dioxo-1,2,3,4-tetrahydro-5-quinazolinyl)acetamide

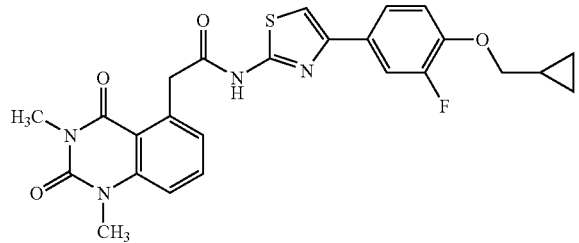

The title compound was prepared according to the general procedure (Method A) by coupling Intermediate 1 (200 mg, 0.806 mmol) with 4-[4-(cyclopropylmethoxy)-3-fluorophenyl]-1,3-thiazol-2-amine (224 mg, 0.806 mmol) in the presence of EDCI hydrochloride (185 mg, 0.967 mmol), HOBt (108 mg, 0.806 mmol) and DMAP (10 mg, 0.080 mmol) in 1,2-dichloroethane (10 ml) to give 31 mg of the title compound as an off white solid. $^1$H NMR (δ ppm, DMSO-d$_6$, 300 Hz): 12.38 (s, 1H); 7.76-7.64 (m, 3H); 7.50 (s, 1H), 7.44 (d, J=8.4, 1H), 7.22-7.16 (m, 2H); 4.33 (s, 2H); 3.93 (d, J=6.9, 2H); 3.54 (s, 3H); 3.22 (s, 3H), 1.29-1.23 (m, 1H); 0.63-0.55 (m, 2H); 0.39-0.31 (m, 2H). IR (cm$^{-1}$, KBr): 3250, 2949, 1694, 1644, 1601, 1546, 1504, 1482, 1409, 1380, 1337, 1277, 1261, 1164, 1129, 1025, 969, 813, 750. MS (m/z): 494.98 ([M]$^+$).

Example 61

N1-[4-(3-Fluoro-4-trifluoromethylphenyl)-1,3-thiazol-2-yl]-2-(1-methyl-3-cyclopropyl-methyl-2,4-dioxo-1,2,3,4-tetrahydro-5-quinazolinyl)acetamide

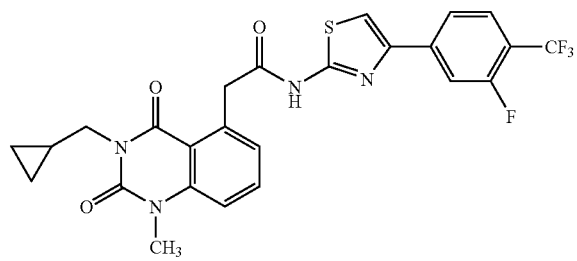

The title compound was prepared according to the general procedure (Method A) by coupling Intermediate 4 (300 mg, 1.040 mmol) with 4-[3-fluoro-4-(trifluoromethyl)phenyl]-1,3-thiazol-2-amine (272 mg, 1.040 mmol) in the presence of EDCI hydrochloride(239 mg, 1.248 mmol), HOBt (140 mg, 1.040 mmol) and DMAP (12.59 mg, 0.104 mmol) in 1,2-dichloroethane (10 ml) to give 35 mg of the title compound as an off white solid. $^1$H NMR (δ ppm, DMSO-d$_6$, 3000 MHz): 12.44 (s, 1H); 7.98-7.83 (m, 4H); 7.69 (t, J=8.7, 1H); 7.42 (d, J=8.4, 1H); 7.19 (d, J=6.9, 1H); 4.33 (s, 2H), 3.75 (d, J=6.9, 2H); 3.54 (s, 3H); 1.07-1.01 (m, 1H); 0.34 (d, J=7.2, 2H); 0.24-0.30 (m, 2H). IR (cm$^{-1}$, KBr): 3250, 2939, 1738, 1687, 1644, 1600, 1504, 1480, 1403, 1383, 1304, 1271, 1193, 1166, 1091, 1024, 926, 805, 745. MS (m/z): 533.19 ([M+H]$^+$).

Example 62

N1-[4-(2,3,6-Trifluorophenyl)-1,3-thiazol-2-yl]-2-(1,3-dimethyl-2,4-dioxo-1,2,3,4-tetrahydro-5-quinazolinyl)acetamide

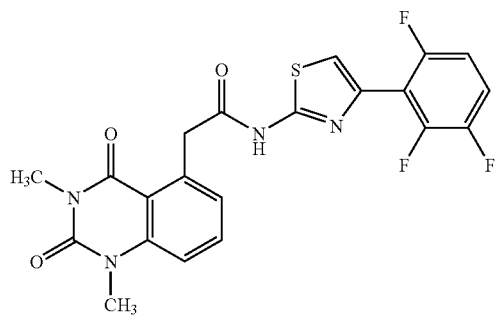

The title compound was prepared according to the general procedure (Method A) by coupling Intermediate 1 (250 mg, 1.008 mmol) with 4-(2,3,6-trifluorophenyl)-1,3-thiazol-2-amine (232 mg, 1.008 mmol) in the presence of EDCI hydrochloride (231 mg, 1.209 mmol), HOBt (136 mg, 1.008 mmol) and DMAP (12 mg, 0.101 mmol) in 1,2-dichloroethane (12 ml) to give 118 mg of the product as an off white solid. $^1$H NMR (δ ppm, DMSO-d$_6$, 300 MHz): 12.47 (s, 1H); 7.72-7.64 (m, 1H); 7.62-7.39 (m, 3H); 7.35-7.15 (m, 2H); 4.31 (s, 2H); 3.53 (s, 3H); 3.22 (s, 3H). IR (cm$^{-1}$, KBr): 3270, 2995, 1697, 1670, 1633, 1597, 1503, 1484, 1426, 1341, 1311, 1276, 1243, 1170, 1156, 1072, 1023, 943, 921, 821, 757. MS (m/z): 461.25 ([M+H]$^+$).

Example 63

N1-[4-(2,4-Dichloro-5-fluorophenyl)-1,3-thiazol-2-yl]-2-(1,3-dimethyl-2,4-dioxo-1,2,3,4-tetrahydro-5-quinazolinyl)acetamide

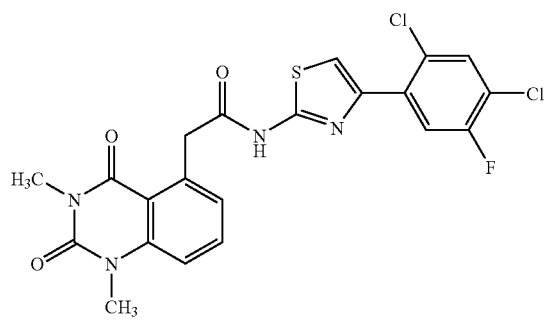

The title compound was prepared according to the general procedure (Method A) by coupling Intermediate 1 (200 mg, 0.806 mmol) with 4-(2,4-dichloro-5-fluorophenyl)-1,3-thiazol-2-amine (210 mg, 0.806 mmol) in the presence of EDCI hydrochloride (185 mg, 0.967 mmol), HOBt (108 mg, 0.806 mmol) and DMAP (10 mg, 0.080 mmol) in 1,2-dichloroethane (10 ml) to give 49 mg of the product as an off white solid. $^1$H NMR (δ ppm, DMSO-$d_6$, 300 MHz): 12.43 (s, 1H); 7.92-7.84 (m, 2H); 7.71-7.65 (m, 2H); 7.41 (d, J=7.8, 1H); 7.18 (d, J=7.5, 1H); 4.32 (s, 2H); 3.53 (s, 3H); 3.21 (s, 3H). IR (cm$^{-1}$, KBr): 3279, 2975, 1698, 1645, 1601, 1551, 1506, 1479, 1461, 1421, 1380, 1356, 1311, 1277, 1152, 1096, 1078, 1023, 884, 772, 758. MS (m/z): 492.94 ([M]$^+$).

Example 64

N1-[4-(2,6Dichloro-3-fluorophenyl)-1,3-thiazol-2-yl]-2-(1,3-dimethyl-2,4-dioxo-1,2,3,4-tetrahydro-5-quinazolinyl)acetamide

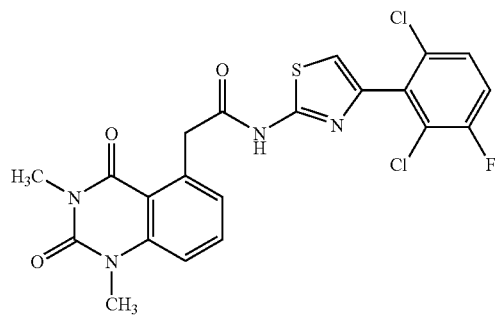

The title compound was prepared according to the general procedure (Method A) by coupling Intermediate 1 (150 mg, 0.604 mmol) with 4-(2,6-dichloro-3-fluorophenyl)-1,3-thiazole-2-amine (160 mg, 0.604 mmol) in the presence of EDCI (140 mg, 0.728 mmol), HOBt (82 mg, 0.604 mmol) and DMAP (15 mg, 0.120 mmol) in 1,2-dichloroethane (8 ml) to give 35 mg of the title compound as an off white solid. Yield: 12%. $^1$H NMR (δ ppm, DMSO-$d_6$, 300 Hz): 12.40 (s, 1H); 7.72-7.51 (m, 3H); 7.42 (d, J=8.4, 1H); 7.26 (s, 1H); 7.17 (d, J=7.2, 1H); 4.32 (s, 2H); 3.54 (s, 3H); 3.23 (s, 3H). IR (cm$^{-1}$, KBr): 3428, 3241, 3213, 3098, 1696, 1635, 1599, 1550, 1526, 1504, 1481, 1442, 1430, 1305, 1252, 1144, 1025, 819, 757. MS (m/z): 492.95 ([M]$^+$).

Example 65

N1-[4-(2,3-Difluoro-4-trifluormethylphenyl)-1,3-thiazol-2-yl]-2-(1,3-dimethyl-2,4-dioxo-1,2,3,4-tetrahydro-5-quinazolinyl)acetamide

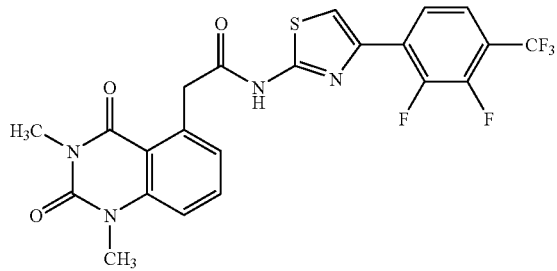

The title compound was prepared according to the general procedure (Method A) by using Intermediate 1 (175 mg, 0.705 mmol), 4-(2,3-difluoro-4-trifluormethylphenyl)-1,3-thiazole-2-amine (197 mg, 0.705 mmol) in the presence of EDCI hydrochloride (162 mg, 0.846 mmol), HOBt (95 mg, 0.705 mmol) and DMAP (17 mg, 0.141 mmol) in 1,2-dichloroethane (9 ml) to give 17 mg of the title compound as an off white solid. $^1$H NMR (δ ppm, DMSO-$d_6$, 300 Hz): 12.55 (s, 1H); 8.04 (t, J=8.7, 1H); 7.76-7.68 (m, 3H); 7.44 (d, J=8.4, 1H); 7.21 (d, J=7.5, 1H); 4.35 (s, 2H); 3.54 (s, 3H); 3.22 (s, 3H). IR (cm$^{-1}$, KBr): 3213, 2945, 1697, 1687, 1628, 1599, 1557, 1506, 1484, 1472, 1419, 1371, 1333, 1314, 1280, 1208, 1173, 1117, 1124, 1075, 1006, 953, 839, 747. MS (m/z): 509.15 ([M–H]$^+$).

Example 66

N1-{4-[3,5-Difluoro-4-trifluoromethylphenyl]-1,3-thiazol-2-yl}-2-(1,3-dimethyl-2,4-dioxo-1,2,3,4-tetrahydro-5-quinazolinyl)acetamide

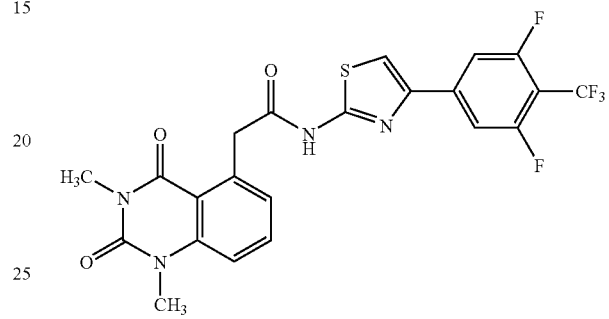

The title compound was prepared according to the general procedure (Method B) by coupling Intermediate 1 (200 mg, 0.806 mmol) with 4-[3,5-difluoro-4-trifluoromethylphenyl]-1,3-thiazol-2-amine (226 mg, 0.806 mmol) in the presence of EDCI hydrochloride (310 mg, 1.612 mmol) and DMAP (19 mg, 0.161 mmol) in mixture of tetrahydrofuran and DMF (3:1 ratio, 4 ml) to give 125 mg of the title compound as an off white solid. $^1$H NMR (δ ppm, DMSO-$d_6$, 300 Hz): 12.53 (s, 1H); 8.04 (s, 1H); 7.86 (d, J=11.7, 2H); 7.71 (t, J=7.8, 1H); 7.44 (d, J=8.4, 1H), 7.21 (d, J=7.5, 1H); 4.34 (s, 2H); 3.54 (s, 3H); 3.22 (s, 3H). IR (cm$^{-1}$, KBr): 3406, 3244, 3213, 1686, 1641, 1602, 1543, 1482, 1433, 1342, 1303, 1246, 1075, 1039, 744. MS (m/z): 510.99 ([M+H]$^+$).

Example 67

N1-{4-[2,4-Difluoro-3-trifluoromethylphenyl]-1,3-thiazol-2-yl}-2-(1,3-dimethyl-2,4-dioxo-1,2,3,4-tetrahydro-5-quinazolinyl)acetamide

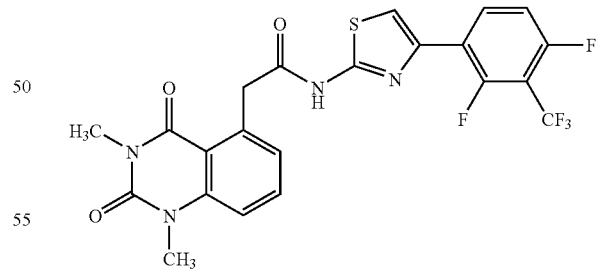

The title compound was prepared according to the general procedure (Method B) by coupling Intermediate 1 (186 mg, 0.751 mmol) with 4-[2,4-difluoro-3-trifluoromethylphenyl]-1,3-thiazol-2-amine (210 mg, 0.751 mmol) in the presence of EDCI hydrochloride (287 mg, 1.501 mmol) and DMAP (18 mg, 0.150 mmol) in mixture of tetrahydrofuran and DMF (3:1 ratio, 4 ml) to give 24 mg of the title compound as an off white solid. $^1$H NMR (δ ppm, DMF-$d_7$, 300 Hz): 12.51 (s, 1H); 8.52-8.42 (m, 1H); 7.77 (t, J=7.8, 1H); 7.66 (s, 1H); 7.59-7.49

(m, 2H), 7.31 (d, J=7.2, 1H); 4.54 (s, 2H); 3.64 (s, 3H); 3.29 (s, 3H). IR (cm$^{-1}$, KBr): 3267, 2916, 1695, 1638, 1626, 1600, 1562, 1507, 1481, 1418, 1307, 1274, 1235, 1123, 1081, 1020, 967, 812, 759. MS (m/z): 511.07 ([M+H]$^+$).

Example 68

N1-{4-[2,6-Difluoro-3-trifluoromethylphenyl]-1,3-thiazol-2-yl}-2-(1,3-dimethyl-2,4-dioxo-1,2,3,4-tetrahydro-5-quinazolinyl)acetamide

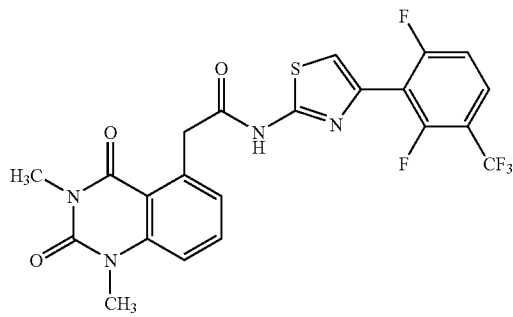

The title compound was prepared according to the general procedure (Method B) by coupling Intermediate 1 (275 mg, 1.108 mmol) with 4-(2,6-difluoro-3-trifluoromethylphenyl)-1,3-thiazole-2-amine (310 mg, 1.108 mmol) in the presence of EDCI hydrochloride (425 mg, 2.216 mmol) and DMAP (26 mg, 0.221 mmol) in mixture of tetrahydrofuran and DMF (3:1 ratio, 6 ml) to give 180 mg of the title compound as an off white solid. $^1$H NMR (δ ppm, DMSO-d$_6$, 300 Hz): 12.54 (s, 1H), 7.97-7.88 (m, 1H); 7.75-7.68 (m, 1H); 7.54 (s, 1H); 7.52-7.45 (m, 2H), 7.21 (d, J=7.8, 1H); 4.33 (s, 2H); 3.55 (s, 3H); 3.23 (s, 3H). MS (m/z): 511.06 ([M+H]$^+$).

Using the similar procedure as described in method A or B, additional examples of quinazolinedione acetamides with multiple fluorine substitutions (as depicted in Table 5) can be prepared by coupling 2-(1,3-Dimethyl-2,4-dioxo-1,2,3,4-tetrahydro-quinazolinyl)acetic acid with an appropriate fluorinated 2-amino-4-arylthiazole selected from Table 2.

TABLE 5

Additional examples of fluorinated quinazolinedione acetamide derivatives

| S No. | Molecular structure | Chemical name | Mol. Formula | Mol Wt. |
|---|---|---|---|---|
| 1 | 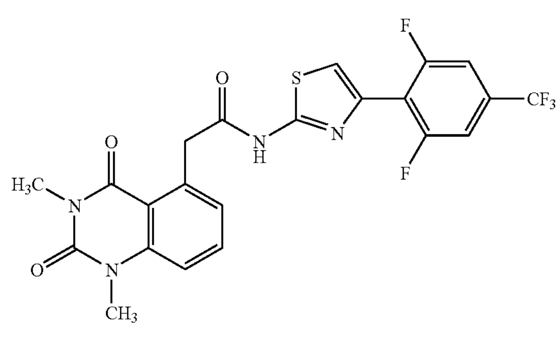 | N1-[4-[2,6-Difluoro-4-trifluoromethylphenyl]-(1,3-thiazol-2-yl}-2-(1,3-dimethyl-2,4-dioxo-1,2,3,4-tetrahydro-5-quinazolinyl) acetamide | $C_{22}H_{15}F_5N_4O_3S$ | 510.44 |
| 2 | 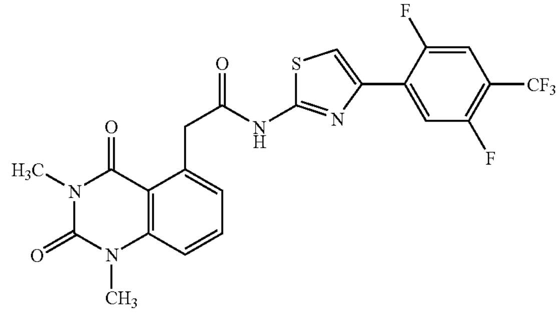 | N1-{4-[2,5-Difluoro-4-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |

TABLE 5-continued

Additional examples of fluorinated quinazolinedione acetamide derivatives

| S No. | Molecular structure | Chemical name | Mol. Formula | Mol Wt. |
|---|---|---|---|---|
| 3 | 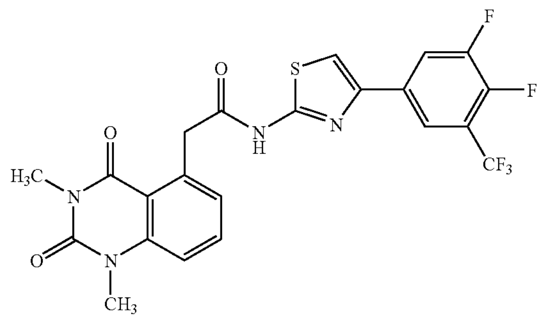 | N1-{4-[3,4-Difluoro-5-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |
| 4 | 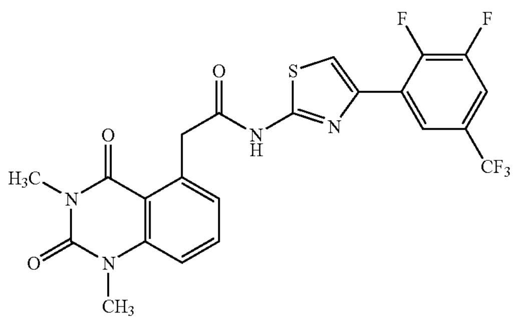 | N1-{4-[2,3-Difluoro-5-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |
| 5 | 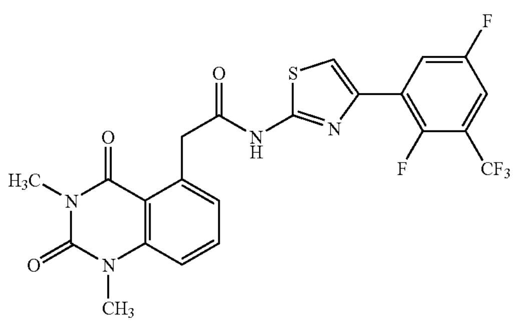 | N1-{4-[2,5-Difluoro-3-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |
| 6 | 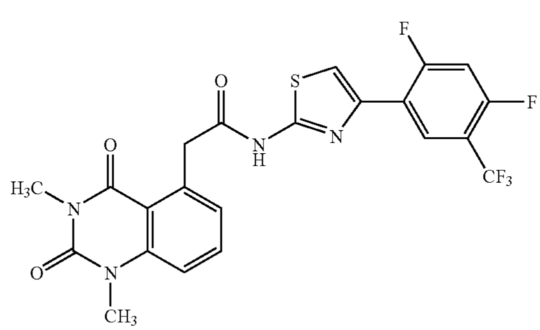 | N1-{4-[2,4-Difluoro-5-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |

TABLE 5-continued

Additional examples of fluorinated quinazolinedione acetamide derivatives

| S No. | Molecular structure | Chemical name | Mol. Formula | Mol Wt. |
|---|---|---|---|---|
| 7 | 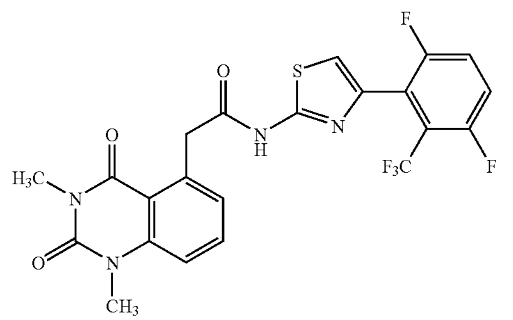 | N1-{4-[3,6-Difluoro-2-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |
| 8 | 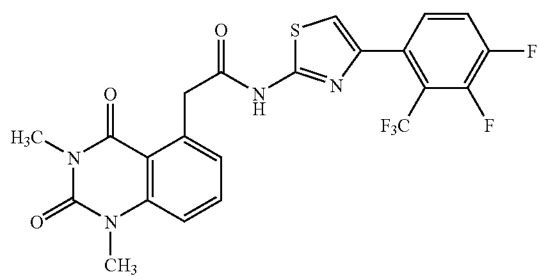 | N1-{4-[3,4-Difluoro-2-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |
| 9 | 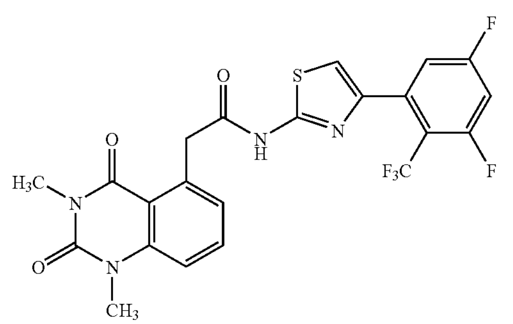 | N1-{4-[3,5-Difluoro-2-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |
| 10 | 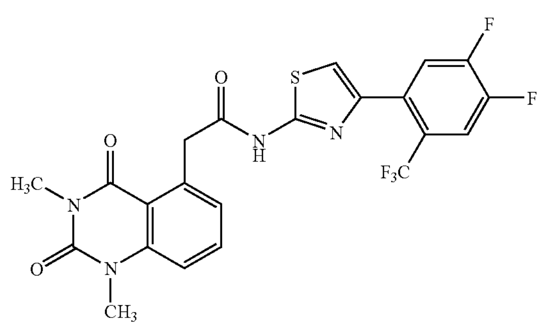 | N1-{4-[4,5-Difluoro-2-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |
| 11 | 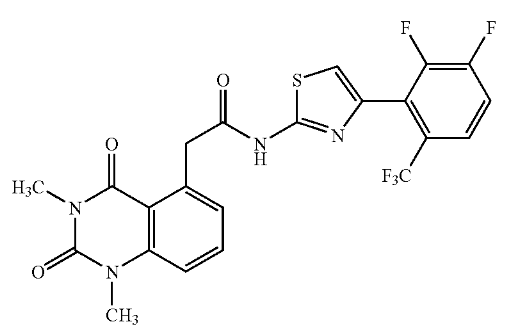 | N1-{4-[2,3-Difluoro-6-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |

TABLE 5-continued

Additional examples of fluorinated quinazolinedione acetamide derivatives

| S No. | Molecular structure | Chemical name | Mol. Formula | Mol Wt. |
|---|---|---|---|---|
| 12 | 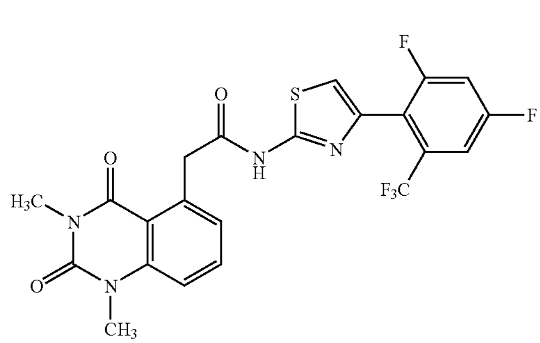 | N1-{4-[2,4-Difluoro-6-trifluoromethylphenyl]-1,3-thiazol-2-yl}-2-(1,3-dimethyl-2,4-dioxo-1,2,3,4-tetrahydro-5-quinazolinyl)acetamide | $C_{22}H_{15}F_5N_4O_3S$ | 510.44 |

Example 69

N1-[4-(4-Difluoromethoxy-3,5-difluorophenyl)-1,3-thiazol-2-yl]-2-(1,3-dimethyl-2,4-dioxo-1,2,3,4-tetrahydro-5-quinazolinyl)propanamide

Example 70

N1-{4-[3,5-Difluoro-4-(2,2,2-trifluoroethoxy)phenyl]-1,3-thiazol-2-yl}-2-(1,3-dimethyl-2,4-dioxo-1,2,3,4-tetrahydro-5-quinazolinyl)acetamide

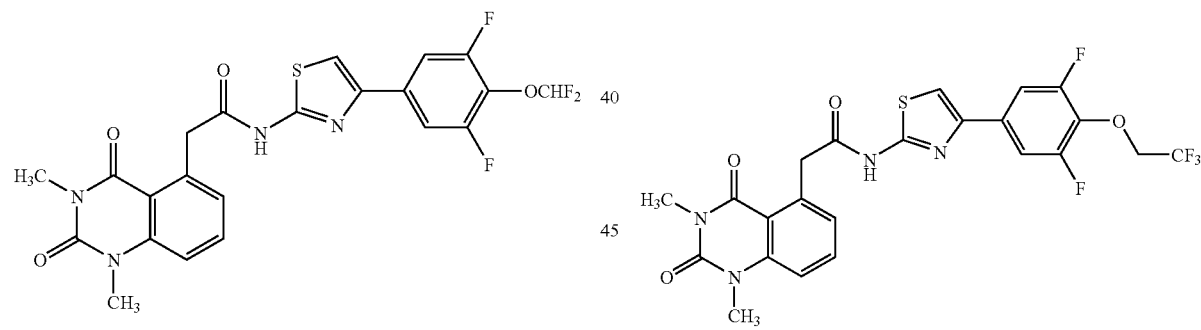

The title compound was prepared according to the general procedure (Method A) by coupling Intermediate 1 (100 mg, 0.403 mmol) with 4-(4-difluoromethoxy-3,5-difluorophenyl)-1,3-thiazole-2-amine (112 mg, 0.403 mmol) in the presence of EDCI hydrochloride (92 mg, 0.483 mmol), HOBt (55 mg, 0.403 mmol) and DMAP (10 mg, 0.080 mmol) in 1,2-dichloroethane (5 ml) to give 15 mg of the title compound as an off white solid. $^1$H NMR (δ ppm, DMSO-$d_6$, 300 Hz): 12.44 (s, 1H); 7.82-7.65 (m, 4H); 7.41 (d, J=8.1, 1H), 7.26 (t, J=71.4, 1H); 7.18 (d, J=7.5, 1H); 4.32 (s, 2H); 3.53 (s, 3H); 3.21 (s, 3H). IR (cm$^{-1}$, KBr): 3240, 3204, 1689, 1641, 1602, 1602, 1546, 1500, 1482, 1434, 1351, 1280, 1155, 1064, 1030, 773. MS (m/z): 507.00 ([M−H]$^−$).

The title compound was prepared according to the general procedure (Method B) by coupling Intermediate 1 (250 mg, 1.008 mmol) with 4-[3,5-difluoro-4-(2,2,2-trifluoroethoxy)phenyl]-1,3-thiazol-2-amine (312 mg, 1.008 mmol) in the presence of EDCI hydrochloride (386 mg, 2.016 mmol) and DMAP (24 mg, 0.201 mmol) in the mixture of THF:DMF (3:1, 5 ml) to give 155 mg of the title compound as an off white solid. $^1$H NMR (δ ppm, DMSO-$d_6$, 300 Hz): 12.45 (s, 1H); 7.76-7.68 (m, 4H); 7.44 (d, J=8.4, 1H); 7.20 (d. J=7.5, 1H); 4.93-4.80 (m, 2H), 4.33 (s, 2H); 3.54 (s, 3H); 3.22 (s, 3H). MS (m/z): 540.98 ([M]$^+$).

Example 71

N1-[4-(3,5-Difluoro-4-methoxyphenyl)-1,3-thiazol-2-yl]-2-(1,3-dimethyl-2,4-dioxo-1,2,3,4-tetrahydroquinazolin-5-yl)acetamide

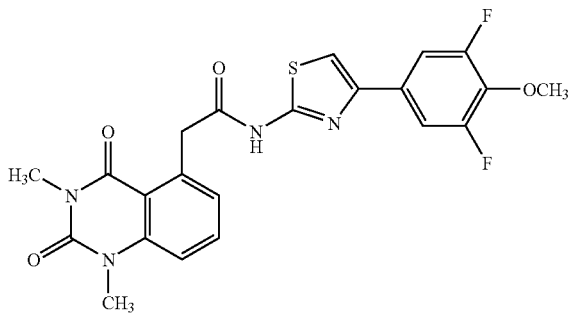

The title compound was prepared according to the general procedure (Method B) by coupling Intermediate 1 (250 mg, 1.008 mmol) with 4-[3,5-difluoro-4-(methoxy)phenyl]-1,3-thiazol-2-amine (244 mg, 1.008 mmol) in the presence of EDCI hydrochloride (386 mg, 2.016 mmol) and DMAP (24 mg, 0.201 mmol) in the mixture of THF:DMF (3:1, 5 ml) to give 230 mg of the title compound as an off white solid. $^1$H NMR (δ ppm, DMSO-$d_6$, 300 Hz): 12.44 (s, 1H); 7.75-7.63 (m, 4H); 7.43 (d, J=8.1, 1H), 7.20 (d, J=7.2, 1H); 4.33 (s, 2H); 3.96 (s, 3H); 3.54 (s, 3H); 3.22 (s, 3H). MS (m/z): 473.03 ([M+H]$^+$).

Example 72

N1-[4-(4-Cyclopropylmethoxy-3,5-difluorophenyl)-1,3-thiazol-2-yl]-2-(1,3-dimethyl-2,4-dioxo-1,2,3,4-tetrahydroquinazolin-5-yl)acetamide

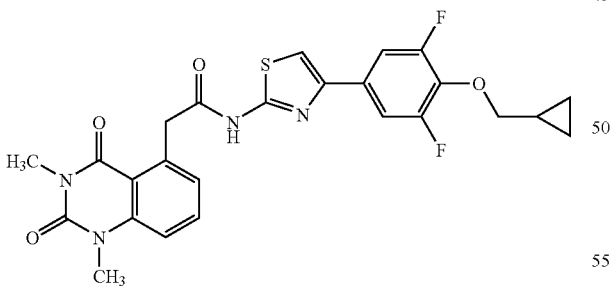

The title compound was prepared according to the general procedure (Method A) by coupling Intermediate 1 (250 mg, 1.008 mmol) with 4-[4-(cyclopropylmethoxy)-3,5-difluorophenyl]-1,3-thiazol-2-amine (284 mg, 1.008 mmol) in the presence of EDCI hydrochloride (230 mg, 1.209 mmol) and HOBt (135 mg, 1.008 mmol) in 1,2-dichloroethane (12 ml) to give 40 mg of the product as an off while solid. $^1$H NMR (δ ppm, DMSO-$d_6$, 300 Hz,): 12.43 (s, 1H); 7.75-7.62 (m, 4H); 7.43 (d, J=8.1, 1H), 7.20 (d, J=7.2, 1H); 4.33 (s, 2H); 3.97 (d, J=6.9, 2H), 3.54 (s, 3H); 3.22 (s, 3H), 1.22-1.16 (m, 1H), 0.53 (d, J=6.9, 2H), 0.30-0.24 (m, 2H). MS (m/z): 507.00 ([M−H]$^+$)

Example 73

N1-[4-(1H-3-Indolyl)-1,3-thiazol-2-yl]-2-(1,3-dimethyl-2,4-dioxo-1,2,3,4-tetrahydro-5-quinazolinyl)acetamide

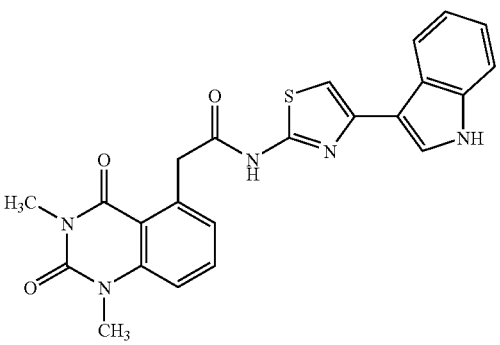

The title compound was prepared according to the general procedure (Method A) by coupling Intermediate 1 (100 mg, 0.403 mmol) with 4-(1H-3-indolyl)-1,3-thiazol-2-amine (87 mg, 0.403 mmol) in the presence of FDCI hydrochloride (93 mg, 0.483 mmol), HOBt (54 mg, 0.403 mmol) and DMAP (5 mg, 0.040 mmol) in 1,2-dichloroethane (5 ml) to give 60 mg of the title compound as an off white solid. $^1$H NMR (δ ppm, DMSO-$d_6$, 300 MHz): 12.26 (s, 1H); 11.27 (s, 1H); 8.08 (d, J=7.8, 1H); 7.74-7.65 (m, 2H); 7.41 (d, J=7.8, 2H); 7.21-7.07 (m, 4H); 4.33 (s, 2H); 3.53 (s, 3H); 3.22 (s, 3H). IR (cm$^{-1}$, KBr): 3261, 2945, 1693, 1633, 1600, 1556, 1504, 1481, 1458, 1429, 1379, 1315, 1242, 1176, 1152, 1033, 963, 821. MS (m/z): 446.29 ([M+H]$^+$).

Example 74

N1-[4-(4-(1-Methyl-3-indolyl)-1,3-thiazol-2-yl]-2-(1,3-dimethyl-2,4-dioxo-1,2,3,4-tetrahydro-5-quinazolinyl)acetamide

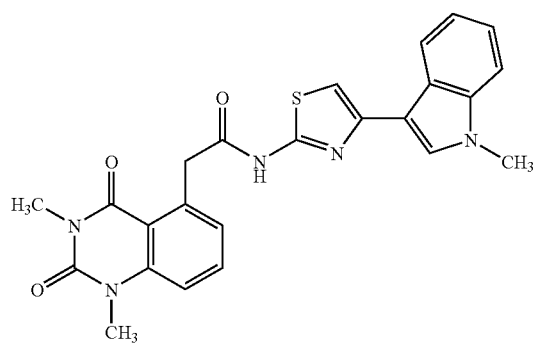

The title compound was prepared according to the general procedure (Method A) by coupling Intermediate 1 (150 mg, 0.604 mmol) with 4-(1-methyl-3-indolyl)-1,3-thiazol-2-amine (138 mg, 0.604 mmol) in the presence of EDCI hydrochloride (139 mg, 0.724 mmol), HOBt (81 mg, 0.604 mmol)

and DMAP (7 mg, 0.060 mmol) in 1,2-dichloroethane (8 ml) to give 60 mg of the title compound as a light brown solid. $^1$H NMR (δ ppm, DMSO-d$_6$, 300 MHz): 12.26 (s, 1H); 8.10 (d, J=7.8, 1H), 7.72-7.65 (m, 2H); 7.49-7.39 (m, 2H); 7.24-7.11 (m, 4H); 4.33 (s, 2H); 3.84 (s, 3H); 3.54 (s, 3H); 3.22 (s, 3H). IR (cm$^{-1}$, KBr): 3272, 2938, 1693, 1682, 1634, 1599, 1557, 1504, 1480, 1466, 1338, 1283, 1242, 1172, 1026, 730. MS (m/z): 458.14 ([M−H]$^+$).

Example 75

N1-Benzo[d][1,3]thiazol-2-yl]-2-(1,3-dimethyl-2,4-dioxo-1,2,3,4-tetrahydro-5-quinazolinyl)acetamide

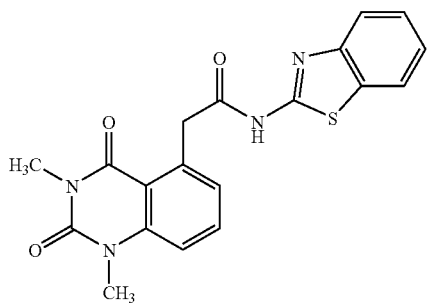

The title compound was prepared according to the general procedure (Method A) by coupling Intermediate 1 (100 mg, 0.403 mmol) with 1,3-benzothiazol-2-amine (60 mg, 0.403 mmol) in the presence of EDCI hydrochloride (93 mg, 0.483 mmol), HOBt (16 mg, 0.120 mmol) and DMAP (5 mg, 0.040 mmol) in 1,2-dichloroethane (5 ml) to give 61 mg of the title compound as a white solid. $^1$H NMR (δ ppm, DMSO-d$_6$, 300 MHz): 12.47 (s, 1H); 7.91 (d, J=7.8, 2H); 7.75-7.65 (m, 2H); 7.41 (t, J=9.0, 1H); 7.25-7.15 (m, 2H); 4.36 (s, 2H); 3.54 (s, 3H); 3.21 (s, 3H). IR (cm$^{-1}$, KBr): 3251, 3209, 3056, 2982, 1699, 1661, 1598, 1539, 1501, 1478, 1417, 1376, 1337, 1315, 1258, 1163, 1142, 1025, 1019, 812. MS (m/z): 381.69 ([M+H]$^+$).

Example 76

N1-[6-Fluorobenzo[d][1,3]thiazol-2-yl]-2-(1,3-dimethyl-2,4-dioxo-1,2,3,4-tetrahydro-5-quinazolinyl)acetamide

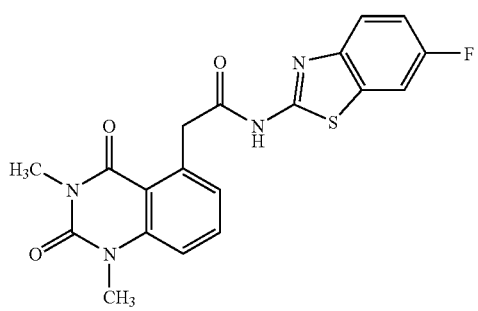

The title compound was prepared according to the general procedure (Method A) by coupling Intermediate 1 (100 mg, 0.403 mmol) with 6-fluoro-1,3-benzothiazol-2-amine (68 mg, 0.403 mmol) in the presence of EDCI hydrochloride (92 mg, 0.483 mmol), HOBt (16 mg, 0.120 mmol) and DMAP (5 mg, 0.040 mmol) in 1,2-dichloroethane (5 ml) to give 84 mg of the title compound as an off-white solid. $^1$H NMR (δ ppm, DMSO-d$_6$, 300 MHz): 12.48 (s, 1H); 7.82 (d, J=7.8, 1H); 7.73-7.65 (m, 2H); 7.42 (d, J=7.8, 1H); 7.28-7.17 (m, 2H); 4.34 (s, 2H); 3.53 (s, 3H); 3.20 (s, 3H). IR (cm$^{-1}$, KBr): 3252, 3209, 2941, 1698, 1659, 1599, 1548, 1501, 1480, 1455, 1418, 1374, 1337, 1268, 1251, 1195, 1141, 1025, 986, 849, 812, 749. MS (m/z): 399.06 ([M+H]$^+$).

Example 77

N1-(5,6-Dimethylbenzo[d][1,3]thiazol-2-yl)-2-(1,3-dimethyl-2,4-dioxo-1,2,3,4-tetrahydro-5-quinazolinyl)acetamide

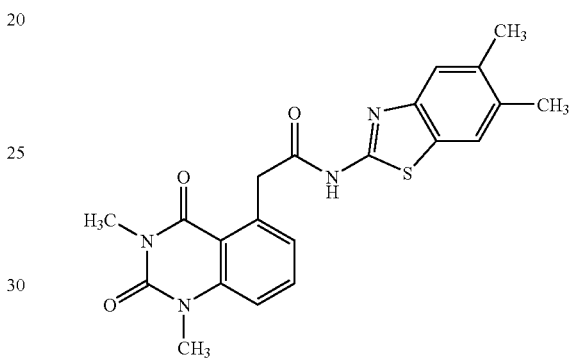

The title compound was prepared according to the general procedure (Method A) by coupling Intermediate 1 (100 mg, 0.403 mmol) with 6-fluoro-1,3-benzothiazol-2-amine (68 mg, 0.403 mmol) in the presence of EDCI hydrochloride (92 mg, 0.483 mmol), HOBt (16 mg, 0.120 mmol) and DMAP (5 mg, 0.040 mmol) in 1,2-dichloroethane (5 ml) to give 84 mg of the title compound as an off-white solid. $^1$H NMR (δ ppm, DMSO-d$_6$, 300 MHz): 12.34 (s, 1H); 7.72-7.62 (m, 1H); 7.63 (s, 1H); 7.51 (s, 1H); 7.42 (d, J=8.1, 1H); 7.18 (d, J=7.2, 1H); 4.33 (s, 2H); 3.53 (s, 3H); 3.21 (s, 3H); 2.31 (s, 3H); 2.28 (s, 3H). IR (cm$^{-1}$, KBr): 3254, 3222, 2994, 2927, 1696, 1634, 1596, 1503, 1478, 1456, 1426, 1380, 1344, 1309, 1285, 1274, 1165, 1041, 1023, 958, 865, 809, 751. MS (m/z): 409.16 ([M+H]$^+$).

Example 78

N1-[4-(7-Chloro-4,5-dihydronaphtho[1,2-d][1,3]-thiazol-2-yl]-2-(1,3-dimethyl-2,4-dioxo-1,2,3,4-tetrahydro-5-quinazolinyl)acetamide

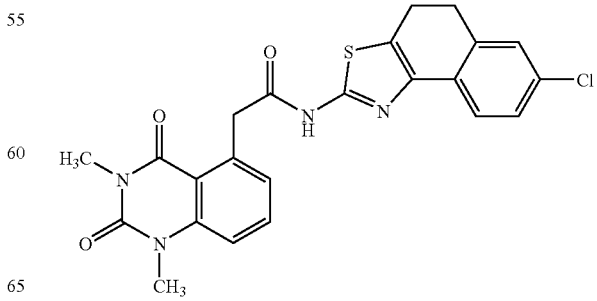

The title compound was prepared according to the general procedure (Method A) by coupling Intermediate 1 (150 mg, 0.604 mmol) with 7-chloro-4,5-dihydronaphtho[1,2-d][1,3]thiazol-2-amine (143 mg, 0.604 mmol) in the presence of EDCI hydrochloride (139 mg, 0.725 mmol), HOBt (24 mg, 0.181 mmol) and DMAP (7 mg, 0.060 mmol) in 1,2-dichloroethane (8 ml) to give 61 mg of the title compound as an off white solid. $^1$H NMR ($\delta$ ppm, DMSO-$d_6$, 300 MHz): 12.30 (br. s, 1H); 7.72-7.60 (m, 2H); 7.41 (d, J=8.1, 1H); 7.34-7.29 (m, 2H); 7.18 (d, J=6.6, 1H); 4.30 (s, 2H); 3.53 (s, 3H); 3.21 (s, 3H); 2.94 (dd, J=6.3, 22.5, 4H). IR (cm$^{-1}$, KBr): 3253, 1693, 1641, 1601, 1553, 1504, 1481, 1427, 1409, 1376, 1340, 1312, 1281, 1252, 1140, 1093, 1024, 879. MS (m/z): 467.15 ([M+H]$^+$).

Example 79

N1-[3-(4-Chlorophenyl)-1H,5-pyrazolyl]-2-(1,3-dimethyl-2,4-dioxo-1,2,3,4-tetrahydro-5-quinazolinyl)acetamide

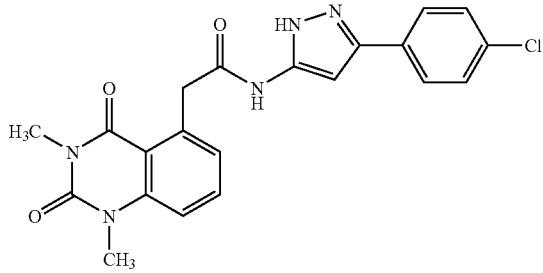

The title compound was prepared according to the general procedure (Method A) by coupling Intermediate 1 (200 mg, 0.806 mmol) with 3-(4-chlorophenyl)-1H-pyrazol-5-amine (156 mg, 0.806 mmol) in the presence of EDCI hydrochloride (185 mg, 0.967 mmol), HOBt (33 mg, 0.241 mmol) and DMAP (10 mg, 0.080 mmol) in 1,2-dichloroethane (10 ml) to give 35 mg of the title compound as an off-white solid. $^1$H NMR ($\delta$ ppm, DMSO-$d_6$, 300 MHz): 12.81 (br. s, 1H); 10.51 (br. s, 1H); 7.80-7.60 (m, 3H); 7.50-7.30 (m, 3H); 7.15 (d, J=7.2, 1H); 6.80 (br. s, 1H); 4.24 (s, 2H); 3.53 (s, 3H); 3.24 (s, 3H). IR (cm$^{-1}$, KBr): 3356, 3085, 2948, 1697, 1640, 1597, 1571, 1499, 1482, 1412, 1315, 1219, 1165, 1090, 960, 725. MS (m/z): 424.34 ([M+H]$^+$).

Example 80

N1-[1-(4-Chlorophenyl)-1H,3-pyrazolyl]-2-(1,3-dimethyl-2,4-dioxo-1,2,3,4-tetrahydro-5-quinazolinyl)acetamide

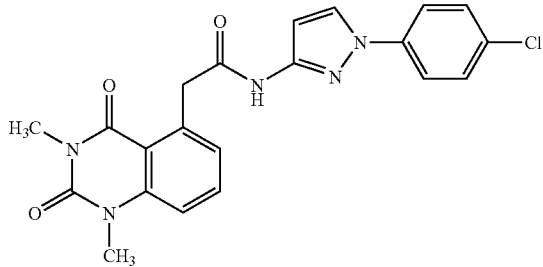

The title compound was prepared according to the general procedure (Method A) by coupling Intermediate 1 (200 mg, 0.806 mmol) with 1-(4-chlorophenyl)-1H-pyrazol-3-amine (155 mg, 0.806 mmol) in the presence of EDCI hydrochloride (185 mg, 0.967 mmol), HOBt (36 mg, 0.241 mmol) and DMAP (10 mg, 0.080 mmol) in 1,2-dichloroethane (10 ml) to give 181 mg of the title compound as a white solid. $^1$H NMR ($\delta$ ppm, CDCl$_3$, 300 MHz): 9.09 (br. s, 1H); 7.71 (br. s, 1H); 7.62 (t, J=7.8, 1H); 7.50 (d, J=8.7, 2H); 7.45-7.10 (m, 4H); 6.89 (br. s, 1H); 4.32 (s, 2H); 3.62 (s, 3H); 3.51 (s, 3H). IR (cm$^{-1}$, KBr): 3320, 2984, 1693, 1646, 1600, 1574, 1504, 1500, 1473, 1428, 1387, 1279, 1178, 1094, 1026, 827; MS (m/z): 424.25 ([M+H]$^+$).

Example 81

N1-[1-(3-Trifluoromethylphenyl)-1H-3-pyrazolyl]-2-(1,3-dimethyl-2,4-dioxo-1,2,3,4-tetrahydro-5-quinazolinyl)acetamide

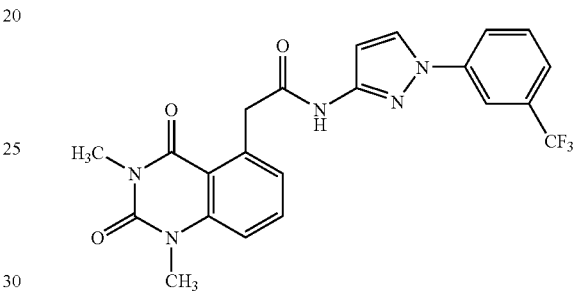

The title compound was prepared according to the general procedure (Method A) by coupling Intermediate 1 (100 mg, 0.403 mmol) with 1-[3-(trifluoromethyl)phenyl]-1H-pyrazol-3-amine (91 mg, 0.403 mmol) in the presence of EDCI hydrochloride (92 mg, 0.483 mmol), HOBt (54 mg, 0.403 mmol) and DMAP (5 mg, 0.040 mmol) in 1,2-dichloroethane (5 ml) to give 61 mg of the title compound as an off-white solid. $^1$H NMR ($\delta$ ppm, DMSO-$d_6$, 300 MHz): 10.87 (s, 1H); 8.53 (s, 1H); 8.10-8.05 (m, 2H); 7.74-7.57 (m, 3H); 7.39 (d, J=7.8, 1H); 7.15 (d, J=7.8, 1H); 6.72 (s, 1H); 4.25 (s, 2H); 3.53 (s, 3H); 3.23 (s, 3H). IR (cm$^{-1}$, KBr): 3265, 1698, 1668, 1655, 1600, 1575, 1503, 1482, 1403, 1381, 1330, 1290, 1177, 1121, 1069, 1025, 765. MS (m/z): 458.01 ([M+H]$^+$).

Example 82

N1-[1-(4-Chloro-2-Fluorophenyl)-1H-3-pyrazolyl]-2-(1,3-dimethyl-2,4-dioxo-1,2,3,4-tetrahydro-5-quinazolinyl)acetamide

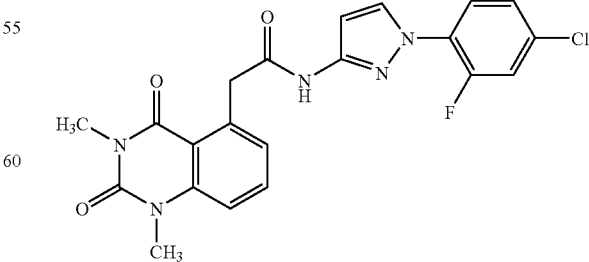

The title compound was prepared according to the general procedure (Method A) by coupling Intermediate 1 (100 mg, 0.403 mmol) with 1-(4-chloro-2-fluorophenyl)-1H-pyrazol-3-amine (77 mg, 0.403 mmol) in the presence of EDCI hydrochloride (92 mg, 0.483 mmol), HOBt (18 mg, 0.120 mmol) and DMAP (5 mg, 0.040 mmol) in 1,2-dichloroethane (4 ml) to give 61 mg of the title compound as an off-white solid. $^1$H NMR (δ ppm, CDCl$_3$, 300 MHz): 9.12 (s, 1H); 7.82 (s, 1H); 7.74 (t, J=8.7, 1H); 7.62 (t, J=8.4, 1H); 7.28 (d, J=6.9, 1H); 7.27-7.15 (m, 3H); 6.91 (s, 1H); 4.32 (s, 2H); 3.61 (s, 3H); 3.50 (s, 3H). IR (cm$^{-1}$, KBr): 3412, 1681, 1700, 1653, 1596, 1570, 1503, 1475, 1430, 1420, 1375, 1313, 1214, 1168, 1140, 1055, 1022, 1014, 944, 887, 857, 827, 757, 748. MS (m/z): 442.19 ([M+H]$^+$).

Example 83

N1-[5-(4-Bromophenyl)-1,3,4-thadiazol-2-yl]-2-(1,3-dimethyl-2,4-dioxo-1,2,3,4-tetrahydro-5-quinazolinyl)acetamide

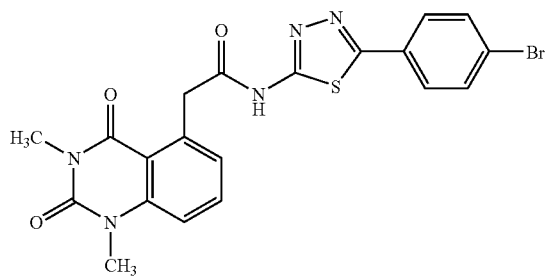

The title compound was prepared according to the general procedure (Method A) by coupling Intermediate 1 (200 mg, 0.806 mmol) with 5-(4-bromophenyl)-1,3,4-thiadiazol-2-amine (206 mg, 0.806 mmol) in the presence of EDCI hydrochloride (185 mg, 0.967 mmol), HOBt (36 mg, 0.241 mmol) and DMAP (10 mg, 0.080 mmol) in 1,2-dichloroethane (10 ml) to give 271 mg of the title compound as an off-white solid. $^1$H NMR (δ ppm, DMSO-d$_6$, 300 MHz): 12.82 (br. s, 1H); 7.85-7.80 (m, 2H); 7.72-7.66 (m, 3H); 7.43 (d, J=7.5, 1H); 7.19 (d, J=7.5, 1H); 4.35 (s, 2H); 3.53 (s, 3H); 3.20 (s, 3H). IR (cm$^{-1}$, KBr): 3429, 2929, 1703, 1659, 1651, 1598, 1570, 1500, 1482, 1442, 1427, 1374, 1361, 1299, 1206, 1179, 1068, 1023, 9874, 817, 747; MS (m/z): 486.10 ([M+H]$^+$).

Pharmacological Activity

The illustrative examples of the present invention are screened for TRPA1 activity according to a modified procedure described in (a) Tóth, A. et al. *Life Sciences* (2003), 73, 487-498. (b) McNamara C. R. et al. *Proc. Natl. Acad. Sci. U.S.A.*, (2007), 104, 13525-13530. The screening of the compounds can be carried out by other methods and procedures known to persons skilled in the art.

Screening for TRPA1 Antagonist Using the $^{45}$Calcium Uptake Assay

The inhibition of TRPA1 receptor activation was measured as inhibition of allyl isothiocyanate (AITC) induced cellular uptake of radioactive calcium. Test compounds were dissolved in DMSO to prepare 10 mM stock solution and then diluted using plain medium with 0.1% BSA and 1.8 mM CaCl$_2$ to get desired concentration. Final concentration of DMSO in the reaction was 0.5% (v/v). Human TRPA1 expressing CHO cells were grown in F-12 DMEM medium with 10% FBS, 1% penicillin-streptomycin solution, 400 µg/ml of G-418. Cells were seeded 24 h prior to the assay in 96 well plates so as to get ~50,000 cells per well on the day of experiment. Cells were treated with test compounds for 10 min followed by addition of AITC at a final concentration of 30 µM and 5 µCi/ml $^{45}$Ca$^{+2}$ for 3 min. Cells were washed and lysed using buffer containing 1% Triton X-100, 0.1% deoxycholate and 0.1% SDS. Radioactivity in the lysate was measured in Packard Top count after addition of liquid scintillant. Concentration response curves were plotted as a % of maximal response obtained in the absence of test antagonist. IC$_{50}$ value was calculated from concentration response curve by nonlinear regression analysis using GraphPad PRISM software.

The compounds prepared were tested using the above assay procedure and the results obtained are given in Table 6. Percentage inhibition at concentrations of 1.0 µM and 10.0 µM are given in the table along with IC$_{50}$ (nM) details for selected examples. The IC$_{50}$ (nM) values of the compounds are set forth in Table 6 wherein "A" refers to an IC$_{50}$ value of less than 50 nM, "B" refers to IC$_{50}$ value in range of 50.1 to 100.0 nM and "C" refers to an IC$_{50}$ value of greater than 100.1 nM.

TABLE 6

In-vitro screening results of compounds of invention

| Examples | Percentage inhibition at 1.0 µM | at 10.0 µM | IC$_{50}$ value (range) |
|---|---|---|---|
| Example 1 | 17.34 | 90.73 | — |
| Example 2 | 25.28 | 50.78 | — |
| Example 3 | 7.98 | 31.58 | — |
| Example 4 | 60.66 | 95.20 | — |
| Example 5 | 52.24 | 71.45 | — |
| Example 6 | 71.35 | 88.20 | — |
| Example 7 | 62.23 | 60.53 | — |
| Example 8 | 52.91 | 79.92 | — |
| Example 9 | 30.75 | 43.75 | — |
| Example 10 | 99.74 | 99.93 | B |
| Example 11 | 95.46 | 99.08 | C |
| Example 12 | 98.65 | 99.17 | B |
| Example 13 | 79.15 | 94.66 | B |
| Example 14 | 97.90 | 99.12 | A |
| Example 15 | 98.0 | 100.0 | A |
| Example 16 | 95.56 | 99.68 | A |
| Example 17 | 30.01 | 75.89 | — |
| Example 18 | 79.32 | 88.26 | A |
| Example 19 | 93.00 | 97.91 | B |
| Example 20 | 98.86 | 99.76 | B |
| Example 21 | 95.70 | 99.71 | A |
| Example 22 | 95.35 | 98.04 | B |
| Example 23 | 96.18 | 96.92 | B |
| Example 24 | 83.91 | 96.75 | B |
| Example 25 | 20.37 | 30.78 | — |
| Example 26 | 13.56 | 5.39 | — |
| Example 27 | 17.24 | 29.63 | — |
| Example 28 | 2.80 | 6.54 | — |
| Example 29 | 20.86 | 47.70 | — |
| Example 30 | 37.29 | 90.97 | — |
| Example 31 | 90.10 | 97.88 | A |
| Example 32 | 53.69 | 66.26 | — |
| Example 33 | 50.44 | 79.77 | — |
| Example 34 | 15.83 | 85.00 | — |
| Example 35 | 76.81 | 95.82 | B |
| Example 36 | 95.13 | 100.00 | A |
| Example 37 | 97.47 | 99.38 | A |
| Example 38 | 98.55 | 98.67 | A |
| Example 39 | 51.62 | 90.32 | — |
| Example 40 | 82.72 | 98.67 | C |
| Example 41 | 74.38 | 99.65 | A |
| Example 42 | 98.27 | 99.04 | B |
| Example 43 | 5.71 | 9.15 | — |
| Example 44 | 46.22 | 99.24 | — |
| Example 45 | 82.09 | 95.49 | C |

TABLE 6-continued

In-vitro screening results of compounds of invention

| Examples | Percentage inhibition at 1.0 µM | at 10.0 µM | IC$_{50}$ value (range) |
|---|---|---|---|
| Example 46 | 84.35 | 87.93 | C |
| Example 47 | 98.44 | 99.24 | B |
| Example 48 | 96.27 | 100 | B |
| Example 49 | 98.60 | 98.96 | B |
| Example 50 | 95.30 | 98.92 | B |
| Example 51 | 97.50 | 99.31 | C |
| Example 52 | 92.49 | 95.27 | C |
| Example 53 | 33.07 | 88.60 | — |
| Example 54 | 74.07 | 99.79 | A |
| Example 55 | 100.00 | 99.98 | A |
| Example 56 | 85.01 | 99.77 | C |
| Example 57 | 97.75 | 99.69 | A |
| Example 58 | 94.15 | 96.67 | C |
| Example 59 | 96.75 | 99.98 | A |
| Example 60 | 1.31 | 41.26 | — |
| Example 61 | 25.03 | 60.39 | — |
| Example 62 | 59.00 | 94.25 | C |
| Example 63 | 87.07 | 96.92 | C |
| Example 64 | 11.54 | 27.01 | — |
| Example 65 | 99.39 | 99.56 | A |
| Example 66 | 99.95 | 100 | A |
| Example 67 | 97.76 | 99.51 (3 µM) | A |
| Example 68 | 84.62 | 98.58 | C |
| Example 69 | 99.88 | 99.98 | A |
| Example 70 | 99.95 | 99.93 | A |
| Example 71 | 83.64 | 98.94 | A |
| Example 72 | 95.42 | 96.45 | A |
| Example 73 | 32.53 | 72.61 | — |
| Example 74 | 96.26 | 97.74 | C |
| Example 75 | 5.60 | 30.50 | — |
| Example 76 | 32.95 | 28.50 | — |
| Example 77 | 49.09 | 95.46 | — |
| Example 78 | 59.81 | 90.32 | C |
| Example 79 | 3.81 | 8.12 | — |
| Example 80 | 97.21 | 99.68 | B |
| Example 81 | 97.06 | 99.59 | B |
| Example 82 | 76.73 | 90.70 | C |
| Example 83 | 5.49 | 3.46 | — |

In Vivo Efficacy Screens for Pain

The illustrative examples of the present invention are screened for 'in vivo' TRPA1 based efficacy in various models of pain/hyperalgesia according to modified procedures described in (a) McNamara C R et al., *PNASU* (2007), 104, 13525-13530 (b) Eid S R et al., *Molecular Pain*, (2008), 4, 48 (c) Bennett G J and Xie Y K, *Pain* (1988), 33, 87-107. The screening of the compounds can also be carried out by some other methods and procedures known to persons skilled in the art.

AITC-Induced Nocifensive Behaviour in Rats

Allyl isothiocyanate (AITC), a selective activator of TRPA1 receptor channel, induces nocifensive behavior (paw flinching and licking responses) in rats. The number of flinches and licking responses were counted for 45 min following the injection of 5% AITC into the plantar region of the paw. AITC being an activator of TRPA1 receptor, this model serves as a mechanistic validation for screened molecules as selective antagonists at TRPA1 channel receptor.

Compound 10 potently blocked the allyl isothiocyanate (AITC) induced nocifensive flinching behavior in male SD rats. Compound 10 at 3, 5 and 10 mg/kg, p.o., showed around 65 to 70% inhibition of AITC-induced flinching in rats at plasma levels ranging 2078 to 7382 ng/ml at 2 h post-dose as shown in FIG. 1 and Table 7.

TABLE 7

Effect of compound 10 on AITC (5%) induced finches in male SD rats:

| Dose (mg/kg, p.o.) | Plasma levels at 2 h (ng/ml) |
|---|---|
| 3 | 2078 |
| 5 | — |
| 10 | 7382 |

Figure 2:
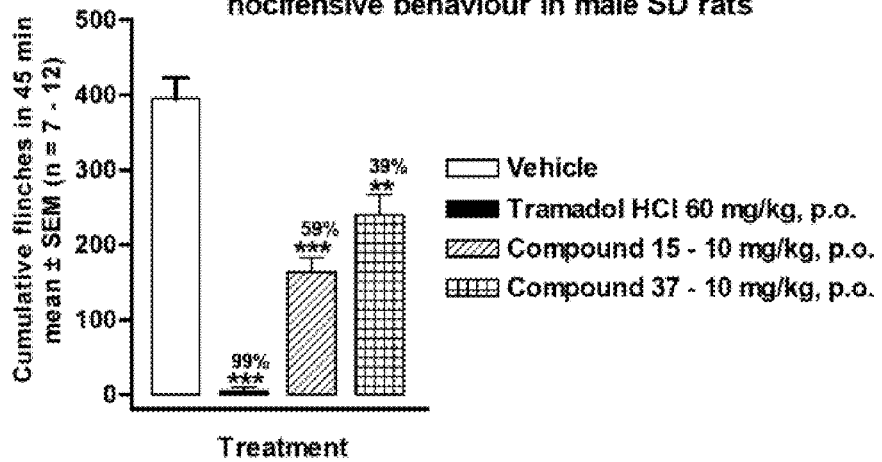
FIG. 2 is a bar graph the effect of Compounds 15 & 37 on Allyl Isothiocyanate (AITC) induced nocifensive behaviour in rats.

Compound 15 and compound 37 also inhibited the AITC induced nocifensive flinching behavior in male SD rats. Compound 15 & 37 at 10 mg/kg, p.o., showed 59 & 39% inhibition of AITC induced flinching in rats, respectively as shown in FIG. 2. The corresponding plasma levels at 4 h post dose were shown in Table 8.

TABLE 8

Effect of compound 15 & 37 on AITC (5%) induced nocifensive behaviour in male SD rats

| Compound No. | Dose (mg/kg, p.o.) | Plasma levels at 4 h (ng/ml) |
|---|---|---|
| 15 | 10 mg | 9804.16 |
| 37 | 10 mg | 6196.35 |

Formalin-Induced Nocifensive Behaviour

Formalin also induces nocifensive behaviour (paw flinching and licking responses) in rats and mice. TRPA1-deficient mice show marked attenuation of characteristic paw flinching and licking responses as a result of intraplantar injection of formalin in a characteristic early and late phase manner. This model also serves as a selective TRPA1 based mechanistic model.

Figure 3:
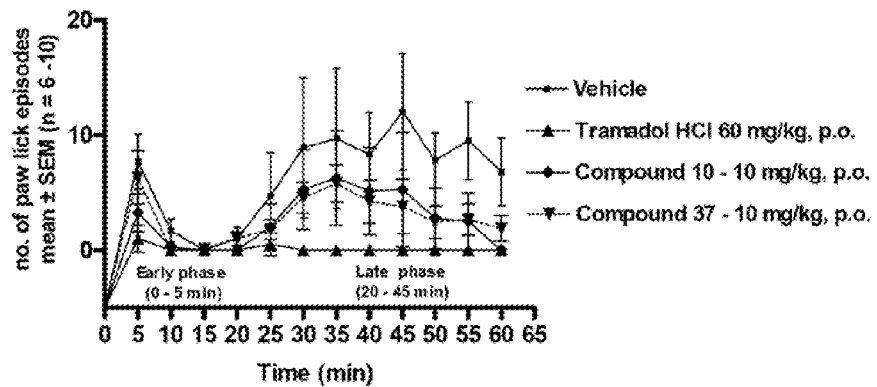
FIG. 3 is a line graph the effect of Compounds 10 & 37 on Formalin induced nocifensive behaviour in rats.

Compound 10 and compound 37 inhibited the formalin-induced nocifensive licking behaviour in both early & late phases in male SD rats. Compound 10 & 37 (10 mg/kg, p.o.), when administered 1.5 & 3 h prior to formalin (2.5%) injection, showed 58 & 18% inhibition of the early phase and 58 & 59% inhibition of the late phase nocifensive behaviour in rats, respectively as depicted in FIG. 3.

FCA (Freund's Complete Adjuvant)-Induced Inflammatory Hyperalgesia

Freund's Complete Adjuvant (FCA), containing heat killed, dried *Mycobaterium tuberculosis* (1 mg/ml) emulsified in mineral oil and mannide monooleate, when injected (30 µl) into the plantar region of the paw of mice and rats induces an inflammatory hyperalgesia. Mechanical hyperalgesia (24 h after injection) was assessed by measuring hind paw withdrawal thresholds to an increasing pressure (g) stimulus, using the Randall-Sellitto analgesymeter (37215, Ugo Basile, Italy) fitted with a wedge-shaped probe.

Figure 4:
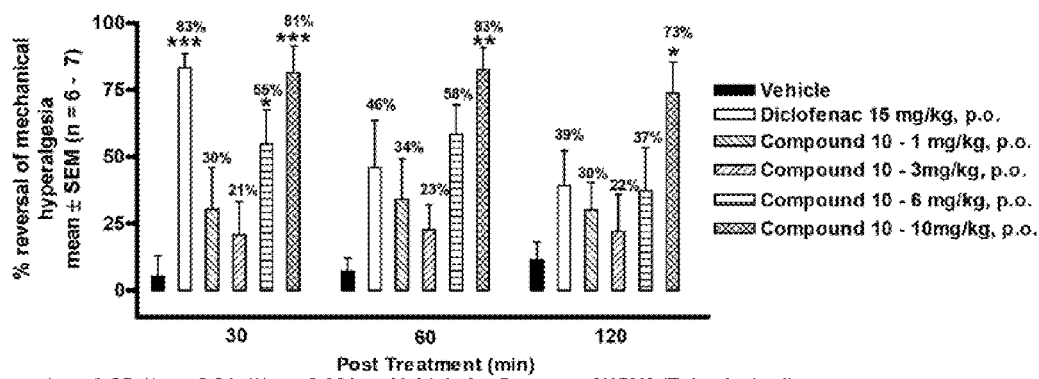
FIG. 4 is a bar graph the effect of Compound 10 on Freund's Complete Adjuvant (FCA) induced inflammatory mechanical hyperalgesia in rats.

Compound 10 was found to have good efficacy against mechanical hyperalgesia. A clear dose-dependent effect was observed at 1, 3, 6 and 10 mg/kg, p.o., with a maximum efficacy of 81% at 10 mg/kg, p.o. (corresponding plasma levels were 3.5 µg/ml at 0.5 h) and an ED$_{50}$ of 2.7 mg/kg, p.o. as depicted in FIG. 4.

Figure 5:
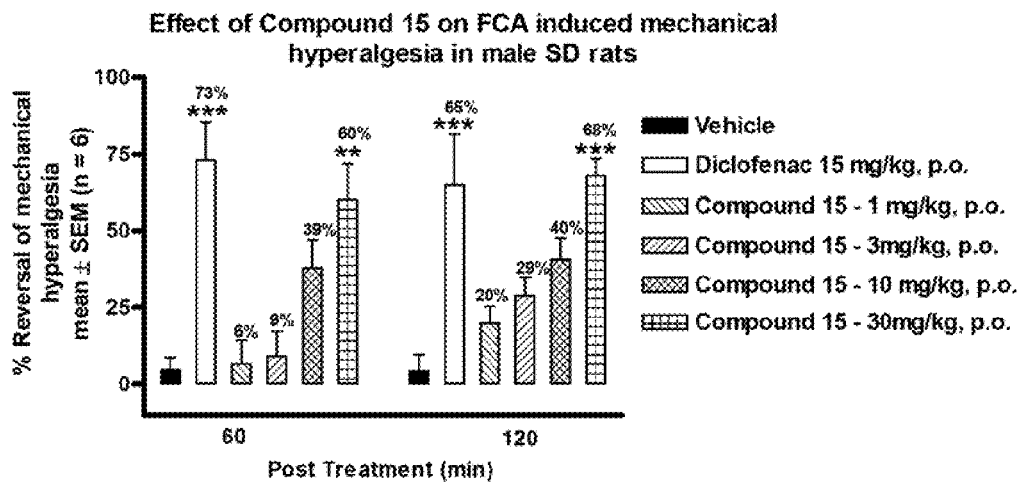
FIG. 5 is a bar graph the effect of Compound 15 on Freund's Complete Adjuvant (FCA) induced inflammatory mechanical hyperalgesia in rats.

Compound 15 was also found to have good dose dependent efficacy FCA-induced mechanical hyperalgesia in rats. A clear dose-dependent effect was observed at 1, 3, 10 and 30 mg/kg, p.o., with a maximum efficacy of ~70% at 30 mg/kg (p.o.) (corresponding plasma levels were 3.43 µg/ml at 1 h) as depicted in FIG. 5.

Chronic Constriction Injury (CCI)-Induced Neuropathic Pain (Bennett's Model)

Chronic constriction injury (CCI) of sciatic nerve in rats and mice induces inflammatory mechanical hyperalgesia in this Bennet's neuropathic pain model. Rats were anesthetized using ketamine/xylazine (40/5 mg/kg, i.p.) and the left sciatic nerve was exposed at mid thigh level through a small incision. Four loose ligatures of 4-0 chromic cat gut (Ethicon-Johnson & Johnson) at 1 mm space were placed around the sciatic nerve after the bifurcation of common sciatic nerve. After 6-7 days, mechanical hyperalgesia was assessed by measuring hind paw withdrawal thresholds to an increasing pressure (g) stimulus, using the Randall-Sellitto analgesymeter (Ugo Basile, Italy), fitted with a wedge-shaped probe.

Figure 6:
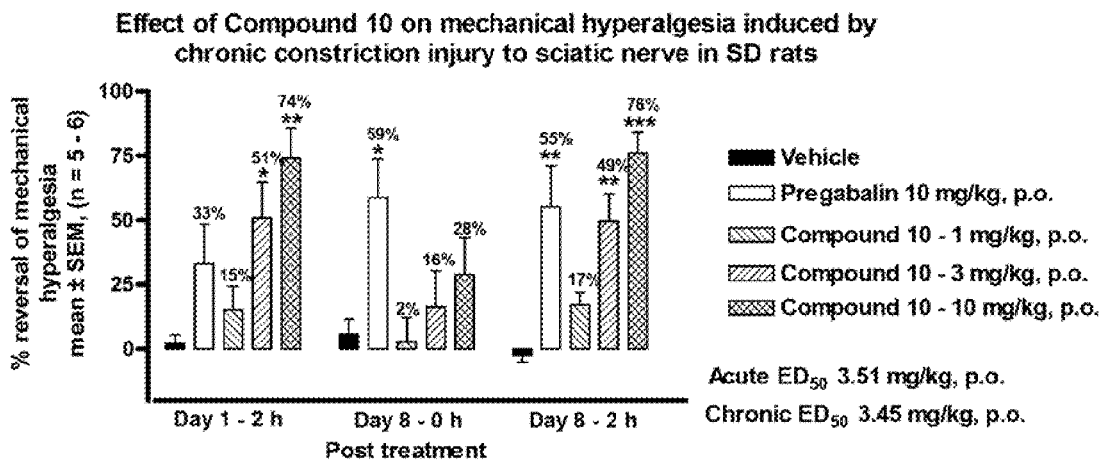
FIG. 6 is a bar graph the effect of Compound 10 on Chronic Constriction Injury (CCI) induced neuropathic hyperalgesia in rats.

Compound 10 showed good efficacy in Bennett's model of neuropathic model induced by CCI in male SD rats with a maximum efficacy of 75% reversal both upon acute and chronic administration in the presence of drug at 10 mg/kg dose (plasma levels 5.1 µg/ml) with an $ED_{50}$ of 3.5 mg/kg as depicted in FIG. 6.

We claim:

1. A compound of Formula (I)

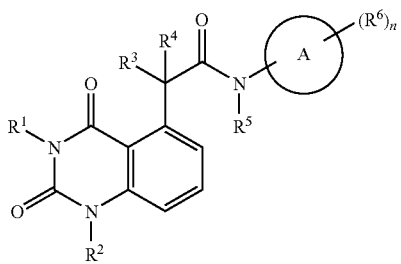

or a tautomer thereof, stereoisomer thereof, or pharmaceutically acceptable salt thereof,
wherein,
ring A is aryl, heteroaryl, heterocyclyl or cycloalkyl;
at each occurrence $R^1$ and $R^2$ is independently selected from hydrogen, hydroxyl, substituted or unsubstituted alkyl, substituted or unsubstituted alkenyl, substituted or unsubstituted alkynyl, substituted or unsubstituted cycloalkyl, substituted or unsubstituted cycloalkylalkyl, $(CR^xR^y)_nOR^x$, $COR^x$, $COOR^x$, $CONR^xR^y$, $SO_2NR^xR^y$, $NR^xR^y$, $NR^x(CR^xR^y)_nOR^x$, $NR^x(CR^xR^y)_n$ $CN(CH_2)_nNR^xR^y$, $(CH_2)_nCHR^xR^y$, $(CR^xR^y)NR^xR^y$, $NR^x(CR^xR^y)_nCONR^xR^y$, $(CH_2)_nNHCOR^x$ and $(CH_2)_n$ $NH(CH_2)_nSO_2R^x$, and $(CH_2)_nNHSO_2R^x$;
each occurrence of $R^x$ and $R^y$ is independently selected from hydrogen, hydroxyl, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, or
when directly attached to a common atom, $R^x$ and $R^y$ together with the atom to which they are attached may form an optionally substituted 3 to 7 membered saturated, unsaturated or partially saturated cyclic ring, which may optionally include one or more heteroatoms selected from O, $NR^a$ or S;
each occurrence of $R^a$ is independently hydrogen or substituted or unsubstituted alkyl;
$R^3$ and $R^4$ are independently selected from hydrogen, hydroxyl, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl; or
$R^3$ and $R^4$ may be joined together to form an optionally substituted 3 to 7 membered saturated or unsaturated cyclic ring, which may optionally include one or more heteroatom or group selected from O, $NR^a$, S, C(O) and $S(O)_{0-2}$; and
$R^5$ is selected from hydrogen, hydroxyl, substituted or unsubstituted alkyl, substituted or unsubstituted alkenyl, substituted or unsubstituted alkynyl, $(CR^xR^y)_nOR^x$, $COR^x$, $COOR^x$, $CONR^xR^y$, $S(O)_{0-2}NR^xR^y$, $NR^xR^y$, $NR^x$ $(CR^xR^y)_nOR^x$, $NR^x(CR^xR^y)_nCN(CH_2)_nNR^xR^y$, $(CH_2)_n$ $CHR^xR^y$, $(CR^xR^y)NR^xR^y$, $NR^x(CR^xR^y)_nCONR^xR^y$, $(CH_2)_nNHCOR^x$ and $(CH_2)_nNH(CH_2)_nSO_2R^x$, and $(CH_2)_nNHSO_2R^x$;
each occurrence of $R^6$ is independently selected from hydrogen, cyano, nitro, $NR^xR^y$, halogen, hydroxyl, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, haloalkyl, haloalkoxy, cycloalkylalkoxy, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, $C(O)OR^x$, $OR^x$, $C(O)NR^xR^y$, $C(O)R^x$, and $SO_2NR^xR^y$;
each occurrence of 'n' is selected from 0 to 5.

2. A compound according to claim 1, wherein ring A is heteroaryl.

3. A compound according to any of claim 1, wherein ring A is selected from pyridine, pyrazole, thiazole, thiadiazole and benzothiazole.

4. A compound according to claim 1, wherein $R^1$ and $R^2$ are independently selected from hydrogen, alkyl and cycloalkylalkyl.

5. A compound according to claim 1, wherein $R^3$ and $R^4$ are hydrogen.

6. A compound according to claim 1, wherein $R^5$ is hydrogen.

7. A compound according to claim 1, wherein $R^6$ is substituted or unsubstituted phenyl.

8. A compound selected from
N1-[3-(4-Bromophenyl)phenyl]-2-(1,3-dimethyl-2,4-dioxo-1,2,3,4-tetrahydro-5-quinazolinyl)acetamide,
N1-[4-(4-Bromophenyl)phenyl]-2-(1,3-dimethyl-2,4-dioxo-1,2,3,4-tetrahydro-5-quinazolinyl)acetamide,
N1-[4-(4-Methylphenoxy)phenyl]-2-(1,3-dimethyl-2,4-dioxo-1,2,3,4-tetrahydro-5-quinazolinyl)acetamide,
N1-[6-(4-Chlorophenyl)-2-pyridyl]-2-(1,3-dimethyl-2,4-dioxo-1,2,3,4-tetrahydro-5-quinazolinyl)acetamide,
N1-[5-(4-Chlorophenyl)-2-pyridyl]-2-(1,3-dimethyl-2,4-dioxo-1,2,3,4-tetrahydro-5-quinazolinyl)acetamide,
N1-[6-(4-Trifluoromethylphenyl)-2-pyridyl]-2-(1,3-dimethyl-2,4-dioxo-1,2,3,4-tetrahydro-5-quinazolinyl)acetamide,
N1-[4-(4-Cyclohexyl)-1,3-thiazol-2-yl]-2-(1,3-dimethyl-2,4-dioxo-1,2,3,4-tetrahydro-5-quinazolinyl)acetamide, N1-[4-Phenyl-1,3-thiazol-2-yl]-2-(1,3-dimethyl-2,4-dioxo-1,2,3,4-tetrahydro-5-quinazolinyl)acetamide,
N1-[4-(4-Fluorophenyl)-1,3-thiazol-2-yl]-2-(1,3-dimethyl-2,4-dioxo-1,2,3,4-tetrahydro-5-quinazolinyl)acetamide,
N1-[4-(4-Chlorophenyl)-1,3-thiazol-2-yl]-2-(1,3-dimethyl-2,4-dioxo-1,2,3,4-tetrahydro-5-quinazolinyl)acetamide,
N1-[4-(3-Chlorophenyl)-1,3-thiazol-2-yl]-2-(1,3-dimethyl-2,4-dioxo-1,2,3,4-tetrahydro-5-quinazolinyl)acetamide,
N1-[4-(4-Bromophenyl)-1,3-thiazol-2-yl]-2-(1,3-dimethyl-2,4-dioxo-1,2,3,4-tetrahydro-5-quinazolinyl)acetamide,
N1-[4-(4-Iodophenyl)-1,3-thiazol-2-yl]-2-(1,3-dimethyl-2,4-dioxo-1,2,3,4-tetrahydro-5-quinazolinyl)acetamide,
N1-[4-(4-Trifluoromethylphenyl)-1,3-thiazol-2-yl]-2-(1,3-dimethyl-2,4-dioxo-1,2,3,4-tetrahydro-5-quinazolinyl)acetamide,
N1-[4-(3-Trifluoromethylphenyl)-1,3-thiazol-2-yl]-2-(1,3-dimethyl-2,4-dioxo-1,2,3,4-tetrahydro-5-quinazolinyl)acetamide,
N1-[4-(3-Trifluoromethoxyphenyl)-1,3-thiazol-2-yl]-2-(1,3-dimethyl-2,4-dioxo-1,2,3,4-tetrahydro-5-quinazolinyl)acetamide,
N1-[4-(4-Methoxyphenyl)-1,3-thiazol-2-yl]-2-(1,3-dimethyl-2,4-dioxo-1,2,3,4-tetrahydro-5-quinazolinyl)acetamide,
N1-[4-(4-Cyclohexylphenyl)-1,3-thiazol-2-yl]-2-(1,3-dimethyl-2,4-dioxo-1,2,3,4-tetrahydro-5-quinazolinyl)acetamide,
N1-[4-(4-(3-Methylbutoxy)phenyl)-1,3-thiazol-2-yl]-2-(1,3-dimethyl-2,4-dioxo-1,2,3,4-tetrahydro-5-quinazolinyl)acetamide,
N1-[4-(4-tert-Butylphenyl)-1,3-thiazol-2-yl]-2-(1,3-dimethyl-2,4-dioxo-1,2,3,4-tetrahydro-5-quinazolinyl)acetamide,
N1-[4-(2-Isobutylphenyl)-1,3-thiazol-2-yl]-2-(1,3-dimethyl-2,4-dioxo-1,2,3,4-tetrahydro-5-quinazolinyl)acetamide,
N1-[4-(4-Isopropylphenyl)-1,3-thiazol-2-yl]-2-(1,3-dimethyl-2,4-dioxo-1,2,3,4-tetrahydro-5-quinazolinyl)acetamide,
N1-[4-(2-Ethylphenyl)-1,3-thiazol-2-yl]-2-(1,3-dimethyl-2,4-dioxo-1,2,3,4-tetrahydro-5-quinazolinyl)acetamide,
N1-[4-(4-Methylphenyl)-1,3-thiazol-2-yl]-2-(1,3-dimethyl-2,4-dioxo-1,2,3,4-tetrahydro-5-quinazolinyl)acetamide,
N1-[4-(4-Chlorophenyl)-1,3-thiazol-2-yl]-2-(1,3-diethyl-2,4-dioxo-1,2,3,4-tetrahydro-5-quinazolinyl)acetamide,
N1-[4-(3-Trifluoromethylphenyl)-1,3-thiazol-2-yl]-2-(1,3-dipropyl-2,4-dioxo-1,2,3,4-tetrahydro-5-quinazolinyl)acetamide,
N1-[4-(4-tert-Butylphenyl)-1,3-thiazol-2-yl]-2-(1-methyl-3-cyclopropylmethyl-2,4-dioxo-1,2,3,4-tetrahydro-5-quinazolinyl)acetamide,
Ethyl-5-[2-(4-Chlorophenyl)-1,3-thiazol-5-ylcarboxymethyl]-2,4-dioxo-1,2,3,4-tetrahydro-3-quinazolinecarboxylate,
N1-[4-(4-Chlorophenyl)-1,3-thiazol-2-yl]-2-(2,4-dioxo-1,2,3,4-tetrahydro-5-quinazolinyl)acetamide,
N1-[4-(4-Chlorophenyl)-5-methyl-1,3-thiazolyl]-2-(1,3-dimethyl-2,4-dioxo-1,2,3,4-tetrahydro-5-quinazolinyl)acetamide,
N1-[4-(2,4-Difluorophenyl)-1,3-thiazol-2-yl]-2-(1,3-dimethyl-2,4-dioxo-1,2,3,4-tetrahydro-5-quinazolinyl)acetamide,
N1-[4-(3,4-Difluorophenyl)-1,3-thiazol-2-yl]-2-(1,3-dimethyl-2,4-dioxo-1,2,3,4-tetrahydro-5-quinazolinyl)acetamide,
N1-[4-(2,6-Difluorophenyl)-1,3-thiazol-2-yl]-2-(1,3-dimethyl-2,4-dioxo-1,2,3,4-tetrahydro-5-quinazolinyl)acetamide,
N1-[4-(3,5-Difluorophenyl)-1,3-thiazol-2-yl]-2-(1,3-dimethyl-2,4-dioxo-1,2,3,4-tetrahydro-5-quinazolinyl)acetamide,
N1-[4-(2,3-Difluorophenyl)-1,3-thiazol-2-yl]-2-(1,3-dimethyl-2,4-dioxo-1,2,3,4-tetrahydro-5-quinazolinyl)acetamide,
N1-[4-(2-Fluoro-4-trifluoromethylphenyl)-1,3-thiazol-2-yl]-2-(1,3-dimethyl-2,4-dioxo-1,2,3,4-tetrahydro-5-quinazolinyl)acetamide,
N1-[4-(3-Fluoro-4-trifluoromethylphenyl)-1,3-thiazol-2-yl]-2-(1,3-dimethyl-2,4-dioxo-1,2,3,4-tetrahydro-5-quinazolinyl)acetamide,
N1-[4-(4-Fluoro-3-trifluoromethylphenyl)-1,3-thiazol-2-yl]-2-(1,3-dimethyl-2,4-dioxo-1,2,3,4-tetrahydro-5-quinazolinyl)acetamide,
N1-[4-(4-Fluoro-2-trifluoromethylphenyl)-1,3-thiazol-2-yl]-2-(1,3-dimethyl-2,4-dioxo-1,2,3,4-tetrahydro-5-quinazolinyl)acetamide,
N1-[4-(2-Fluoro-5-trifluoromethylphenyl)-1,3-thiazol-2-yl]-2-(1,3-dimethyl-2,4-dioxo-1,2,3,4-tetrahydro-5-quinazolinyl)acetamide,
N1-[4-(3-Fluoro-4-trifluoromethoxyphenyl)-1,3-thiazol-2-yl]-2-(1,3-dimethyl-2,4-dioxo-1,2,3,4-tetrahydro-5-quinazolinyl)propanamide,
N1-[4-(4-Fluoro-3-trifluoromethoxyphenyl)-1,3-thiazol-2-yl]-2-(1,3-dimethyl-2,4-dioxo-1,2,3,4-tetrahydro-5-quinazolinyl)propanamide,
N1-[4-(3-Fluoro-4-methoxyphenyl)-1,3-thiazol-2-yl]-2-(1,3-dimethyl-2,4-dioxo-1,2,3,4-tetrahydro-5-quinazolinyl)propanamide,
N1-[4-(4-Difluoromethoxyl-3-fluorophenyl)-1,3-thiazol-2-yl]-2-(1,3-dimethyl-2,4-dioxo-1,2,3,4-tetrahydro-5-quinazolinyl)acetamide,
N1-[4-(2,4-Dichlorophenyl)-1,3-thiazol-2-yl]-2-(1,3-dimethyl-2,4-dioxo-1,2,3,4-tetrahydro-5-quinazolinyl)acetamide,
N1-[4-(2,5-Dichlorophenyl)-1,3-thiazol-2-yl]-2-(1,3-dimethyl-2,4-dioxo-1,2,3,4-tetrahydro-5-quinazolinyl)acetamide,
N1-[4-(3,4-Dichlorophenyl)-1,3-thiazol-2-yl]-2-(1,3-dimethyl-2,4-dioxo-1,2,3,4-tetrahydro-5-quinazolinyl)acetamide,
N1-[4-(3,5-Dichlorophenyl)-1,3-thiazol-2-yl]-2-(1,3-dimethyl-2,4-dioxo-1,2,3,4-tetrahydro-5-quinazolinyl)acetamide,
N1-[4-(3-Chloro-4-fluorophenyl)-1,3-thiazol-2-yl]-2-(1,3-dimethyl-2,4-dioxo-1,2,3,4-tetrahydro-5-quinazolinyl)acetamide,
N1-[4-(3-Chloro-2-fluorophenyl)-1,3-thiazol-2-yl]-2-(1,3-dimethyl-2,4-dioxo-1,2,3,4-tetrahydro-5-quinazolinyl)acetamide,
N1-[4-(4-Chloro-2-fluorophenyl)-1,3-thiazol-2-yl]-2-(1,3-dimethyl-2,4-dioxo-1,2,3,4-tetrahydro-5-quinazolinyl)acetamide,
N1-[4-(5-Chloro-2-fluorophenyl)-1,3-thiazol-2-yl]-2-(1,3-dimethyl-2,4-dioxo-1,2,3,4-tetrahydro-5-quinazolinyl)acetamide, N1-[4-(2-Chloro-6-fluorophenyl)-1,3-thiazol-2-yl]-2-(1,3-dimethyl-2,4-dioxo-1,2,3,4-tetrahydro-5-quinazolinyl)acetamide, N1-[4-(2-Chloro-4-fluorophenyl)-1,3-thiazol-2-yl]-2-(1,3-dimethyl-2,4-dioxo-1,2,3,4-tetrahydro-5-quinazolinyl)propanamide, N1-[4-(4-Chloro-3-trifluoromethylphenyl)-1,3-thiazol-2-yl]-2-(1,3-dimethyl-2,4-dioxo-1,2,3,4-tetrahydro-5-quinazolinyl)acetamide, N1-[4-(2-Chloro-5-trifluoromethylphenyl)-1,3-thiazol-2-yl]-2-(1,3-dimethyl-2,4-dioxo-1,2,3,4-tetrahydro-5-quinazolinyl)propanamide, N1-{4-[3-Chloro-4-(difluoromethoxy)phenyl]-1,3-thiazol-2-yl}-2-(1,3-dimethyl-2,4-dioxo-1,2,3,4-tetrahydro-5-quinazolinyl)acetamide, N1-[4-(4-Chloro-3-methylphenyl)-1,3-thiazol-2-yl]-2-(1,3-dimethyl-2,4-dioxo-1,2,3,4-tetrahydro-5-quinazolinyl)acetamide, N1-{4-[3-Fluoro-4-(2,2,2-trifluoroethoxy)phenyl]-1,3-thiazol-2-yl}-2-(1,3-dimethyl-2,4-dioxo-1,2,3,4-tetrahydro-5-quinazolinyl)acetamide, N1-[4-(4-Cyclopropylmethoxy-3-fluorophenyl)-1,3-thiazol-2-yl]-2-(1,3-dimethyl-2,4-dioxo-1,2,3,4-tetrahydro-5-quinazolinyl)acetamide, N1-[4-(3-Fluoro-4-trifluoromethylphenyl)-1,3-thiazol-2-yl]-2-(1-methyl-3-cyclopropylmethyl-2,4-dioxo-1,2,3,4-tetrahydro-5-quinazolinyl)acetamide, N1-[4-(4-(2,3,6-Trifluorophenyl)-1,3-thiazol-2-yl]-2-(1,3-dimethyl-2,4-dioxo-1,2,3,4-tetrahydro-5-quinazolinyl)acetamide, N1-[4-(2,4-Dichloro-5-fluorophenyl)-1,3-thiazol-2-yl]-2-(1,3-dimethyl-2,4-dioxo-1,2,3,4-tetrahydro-5-quinazolinyl)acetamide, N1-[4-(2,6-Dichloro-3-fluorophenyl)-1,3-thiazol-2-yl]-2-(1,3-dimethyl-2,4-dioxo-1,2,3,4-tetrahydro-5-quinazolinyl)acetamide, N1-[4-(2,3-Difluoro-4-trifluormethylphenyl)-1,3-thiazol-2-yl]-2-(1,3-dimethyl-2,4-dioxo-1,2,3,4-tetrahydro-5-quinazolinyl)acetamide, N1-{4-[3,5-Difluoro-4-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,4-Difluoro-3-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,6-Difluoro-3-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,6-Difluoro-4-trifluoromethylphenyl]-1,3-thiazol-2-yl}-2-(1,3-dimethyl-2,4-dioxo-1,2,3,4-tetrahydro-5-quinazolinyl)acetamide, N1-{-4-[2,5-Difluoro-4-trifluoromethylphenyl]-1,3-thiazol-2-yl}-2-(1,3-dimethyl-2,4-dioxo-1,2,3,4-tetrahydro-5-quinazolinyl)acetamide, N1-{4-[3,4-Difluoro-5-trifluoromethylphenyl]-1,3-thiazol-2-yl}-2-(1,3-dimethyl-2,4-dioxo-1,2,3,4-tetrahydro-5-quinazolinyl)acetamide, N1-{-4-[2,3-Difluoro-5-trifluoromethylphenyl]-1,3-thiazol-2-yl}-2-(1,3-dimethyl-2,4-dioxo-1,2,3,4-tetrahydro-5-quinazolinyl)acetamide, N1-{-4-[2,5-Difluoro-3-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,4-Difluoro-5-trifluoromethylphenyl]-1,3-thiazol-2-yl}-2-(1,3-dimethyl-2,4-dioxo-1,2,3,4-tetrahydro-5-quinazolinyl)acetamide, N1-{4-[3,6-Difluoro-2-trifluoromethylphenyl]-1,3-thiazol-2-yl}-2-(1,3-dimethyl-2,4-dioxo-1,2,3,4-tetrahydro-5-quinazolinyl)acetamide, N1-{4-[3,4-Difluoro-2-trifluoromethylphenyl]-1,3-thiazol-2-yl}-2-(1,3-dimethyl-2,4-dioxo-1,2,3,4-tetrahydro-5-quinazolinyl)acetamide, N1-{4-[3,5-Difluoro-2-trifluoromethylphenyl]-1,3-thiazol-2-yl}-2-(1,3-dimethyl-2,4-dioxo-1,2,3,4-tetrahydro-5-quinazolinyl)acetamide, N1-{4-[4,5-Difluoro-2-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,3-Difluoro-6-trifluoromethylphenyl]-1,3-thiazol-2-yl}-2-(1,3-dimethyl-2,4-dioxo-1,2,3,4-tetrahydro-5-quinazolinyl)acetamide, N1-{4-[2,4-Difluoro-6-trifluoromethylphenyl]-1,3-thiazol-2-yl}-2-(1,3-dimethyl-2,4-dioxo-1,2,3,4-tetrahydro-5-quinazolinyl)acetamide, N1-[4-(4-Difluoromethoxy-3,5-difluorophenyl)-1,3-thiazol-2-yl]-2-(1,3-dimethyl-2,4-dioxo-1,2,3,4-tetrahydro-5-quinazolinyl)propanamide, N1-{4-[3,5-Difluoro-4-(2,2,2-trifluoroethoxy)phenyl]-1,3-thiazol-2-yl}-2-(1,3-dimethyl-2,4-dioxo-1,2,3,4-tetrahydro-5-quinazolinyl)acetamide, N1-[4-(3,5-Difluoro-4-methoxyphenyl)-1,3-thiazol-2-yl]-2-(1,3-dimethyl-2,4-dioxo-1,2,3,4-tetrahydroquinazolin-5-yl)acetamide, N1-[4-(4-Cyclopropylmethoxy-3,5-difluorophenyl)-1,3-thiazol-2-yl]-2-(1,3-dimethyl-2,4-dioxo-1,2,3,4-tetrahydroquinazolin-5-yl)acetamide, N1-[4-(1H-3-Indolyl)-1,3-thiazol-2-yl]-2-(1,3-dimethyl-2,4-dioxo-1,2,3,4-tetrahydro-5-quinazolinyl)acetamide, N1-[4-(4-(1-Methyl-3-indolyl)-1,3-thiazol-2-yl]-2-(1,3-dimethyl-2,4-dioxo-1,2,3,4-tetrahydro-5-quinazolinyl)acetamide, N1-Benzo[d][1,3]thiazol-2-yl]-2-(1,3-dimethyl-2,4-dioxo-1,2,3,4-tetrahydro-5-quinazolinyl)acetamide, N1-[6-Fluorobenzo[d][1,3]thiazol-2-yl)-2-(1,3-dimethyl-2,4-dioxo-1,2,3,4-tetrahydro-5-quinazolinyl)acetamide, N1-(5,6-Dimethylbenzo[d][1,3]thiazol-2-yl)-2-(1,3-dimethyl-2,4-dioxo-1,2,3,4-tetrahydro-5-quinazolinyl)acetamide, N1-[4-(7-chloro-4,5-dihydronaphtho[1,2-d][1,3]-thiazol-2-yl]-2-(1,3-dimethyl-2,4-dioxo-1,2,3,4-tetrahydro-5-quinazolinyl)acetamide, N1-[3-(4-Chlorophenyl)-1H,5-pyrazolyl]-2-(1,3-dimethyl-2,4-dioxo-1,2,3,4-tetrahydro-5-quinazolinyl)acetamide, N1-[1-(4-Chlorophenyl)-1H,3-pyrazolyl]-2-(1,3-dimethyl-2,4-dioxo-1,2,3,4-tetrahydro-5-quinazolinyl)acetamide, N1-[1-(3-Trifluoromethylphenyl)-1H-3-pyrazolyl]-2-(1,3-dimethyl-2,4-dioxo-1,2,3,4-tetrahydro-5-quinazolinyl)acetamide, N1-[1-(4-Chloro-2-fluorophenyl)-1H-3-pyrazolyl]-2-(1,3-dimethyl-2,4-dioxo-1,2,3,4-tetrahydro-5-quinazolinyl)acetamide, N1-[5-(4-Bromophenyl)-1,3,4-thadiazol-2-yl]-2-(1,3-dimethyl-2,4-dioxo-1,2,3,4-tetrahydro-5-quinazolinyl) acetamide, or a tautomer thereof, a stereoisomer thereof, or a pharmaceutically acceptable salt thereof.

9. A compound of formula (Ia)

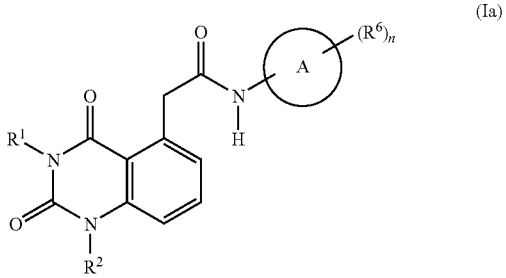

or a tautomer thereof, a stereoisomer thereof, or a pharmaceutically acceptable salt thereof,
wherein,
at each occurrence $R^1$ and $R^2$ is independently selected from hydrogen, hydroxyl, substituted or unsubstituted alkyl, substituted or unsubstituted alkenyl, substituted or unsubstituted alkynyl, substituted or unsubstituted cycloalkyl, substituted or unsubstituted cycloalkylalkyl, $(CR^xR^y)_nOR^x$, $COR^x$, $COOR^x$, $CONR^xR^y$, $SO_2NR^xR^y$, $NR^xR^y$, $NR^x(CR^xR^y)_nOR^x$, $NR^x(CR^xR^y)_nCN(CH_2)_nNR^xR^y$, $(CH_2)_nCHR^xR^y$, $(CR^xR^y)NR^xR^y$, $NR^x(CR^xR^y)_nCONR^xR^y$, $(CH_2)_nNHCOR^x$ and $(CH_2)_nNH(CH_2)_nSO_2R^x$, and $(CH_2)_nNHSO_2R^x$;
each occurrence of $R^x$ and $R^y$ is independently selected from hydrogen, hydroxyl, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, or
when directly attached to a common atom, $R^x$ and $R^y$ together with the atom to which they are attached may form an optionally substituted 3 to 7 membered saturated, unsaturated or partially saturated cyclic ring, which may optionally include one or more heteroatoms selected from O, $NR^a$ or S;
each occurrence of $R^a$ is independently hydrogen or substituted or unsubstituted alkyl; ring A is selected from phenyl, pyridinyl, pyrazolyl, thiazolyl and thiadiazolyl;
each occurrence of $R^6$ is independently hydrogen, cyano, nitro, $NR^xR^y$, halogen, hydroxyl, haloalkyl, haloalkoxy, cycloalkylalkoxy, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl,
$R^x$ and $R^y$ are independently selected from hydrogen, hydroxyl, halogen, substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, and substituted or unsubstituted heteroarylalkyl; and
each occurrence of 'n' is selected from 0 to 5.

10. A compound according to claim 9, wherein ring A is thiazole.
11. A compound according to claim 9, wherein $R^1$ and $R^2$ are independently selected from hydrogen, alkyl and cycloalkylalkyl.
12. A compound according to claim 11, wherein $R^1$ and $R^2$ are selected from methyl, ethyl, propyl and butyl.
13. A compound according to claim 9, wherein $R^6$ is substituted or unsubstituted phenyl.
14. A compound of Formula (Ib)

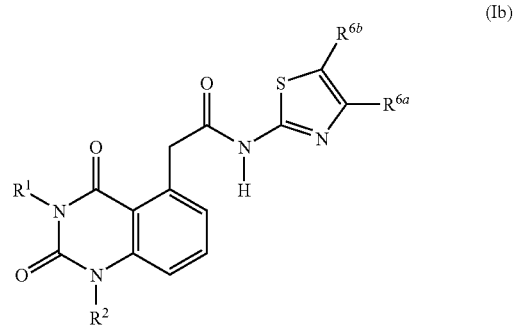

or a tautomer thereof, stereoisomer thereof, or pharmaceutically acceptable salt thereof,
wherein,
at each occurrence $R^1$ and $R^2$ is independently selected from hydrogen, hydroxyl, substituted or unsubstituted alkyl, substituted or unsubstituted alkenyl, substituted or unsubstituted alkynyl, substituted or unsubstituted cycloalkyl, substituted or unsubstituted cycloalkylalkyl, $(CR^xR^y)_nOR^x$, $COR^x$, $COOR^x$, $CONR^xR^y$, $SO_2NR^xR^y$, $NR^xR^y$, $NR^x(CR^xR^y)_nOR^x$, $NR^x(CR^xR^y)_nCN(CH_2)_nNR^xR^y$, $(CH_2)_nCHR^xR^y$, $(CR^xR^y)NR^xR^y$, $NR^x(CR^xR^y)_nCONR^xR^y$, $(CH_2)_nNHCOR^x$ and $(CH_2)_nNH(CH_2)_nSO_2R^x$, and $(CH_2)_nNHSO_2R^x$;
each occurrence of 'n' is selected from 0 to 5;
$R^{6a}$ and $R^{6b}$ are independently selected from hydrogen, cyano, nitro, $-NR^xR^y$, halogen, hydroxyl, haloalkyl, haloalkoxy, cycloalkylalkoxy, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, $-C(O)OR^x$, $-OR^x$, $-C(O)NR^xR^y$, $-C(O)R^x$, $-SO_2R^x$, $-SO_2-NR^xR^y$;
$R^{6a}$ and $R^{6b}$ together with the carbon to which they are attached may form an optionally substituted 4 to 14 membered saturated, unsaturated or partially saturated ring systems, which may optionally include one or more heteroatoms selected from O, N or S;
$R^x$ and $R^y$ are independently selected from hydrogen, hydroxyl, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heteroarylalkyl, substituted or unsubstituted heterocyclic ring and substituted or unsubstituted heterocyclylalkyl, or when directly attached to a common atom, $R^x$ and $R^y$ together with the atom to which they are attached may form an optionally substituted 3 to 7 membered saturated, unsaturated or partially saturated cyclic ring, which may optionally include one or more heteroatoms selected from O, $NR^a$ or S;

each occurrence of $R^a$ is hydrogen or substituted or unsubstituted alkyl.

15. A compound according to claim 14, wherein $R^1$ and $R^2$ are independently selected from hydrogen, alkyl and cycloalkylalkyl.

16. A compound according to claim 15, wherein $R^1$ and $R^2$ are selected from methyl, ethyl, propyl and butyl.

17. A compound according to claim 14, wherein $R^{6a}$ is substituted or unsubstituted phenyl.

18. A compound according to claim 14, wherein $R^{6a}$ and $R^{6b}$ are independently or taken together to form substituted or unsubstituted cyclohexyl, benzothiazole or naphthothiazole.

19. A compound according to claim 14, wherein $R^{6b}$ is hydrogen or methyl.

20. A pharmaceutical composition comprising one or more compounds of claim 1, and one or more pharmaceutically acceptable excipients, carriers, diluents or mixture thereof.

21. N1-{4-[2,4-Difluoro-3-trifluoromethylphenyl]-1,3-thiazol-2-yl}-2-(1,3-dimethyl-2,4-dioxo-1,2,3,4-tetrahydro-5-quinazolinyl)acetamide.

22. N1-{4-[2,4-Difluoro-3-trifluoromethylphenyl]-1,3-thiazol-2-yl}-2-(1,3-dimethyl-2,4-dioxo-1,2,3,4-tetrahydro-5-quinazolinyl)acetamide or a pharmaceutically acceptable salt thereof.

23. A pharmaceutical composition comprising N1-{4-[2,4-Difluoro-3-trifluoromethyl-phenyl]-1,3-thiazol-2-yl}-2-(1,3-dimethyl-2,4-dioxo-1,2,3,4-tetrahydro-5-quinazolinyl)acetamide or a pharmaceutically acceptable salt thereof, and one or more pharmaceutically acceptable excipients, carriers, diluents or mixture thereof.

* * * * *